US006465627B2

(12) United States Patent
McCabe et al.

(10) Patent No.: US 6,465,627 B2
(45) Date of Patent: *Oct. 15, 2002

(54) DAX-1 PROTEIN, METHODS FOR PRODUCTION AND USE THEREOF

(75) Inventors: Edward R. B. McCabe, Pacific Palisades, CA (US); Weiwen Guo, Los Angeles, CA (US); Thomas P. Burris, Woodland Hills, CA (US); Eric Vilain, Los Angeles, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/687,691

(22) Filed: Jul. 26, 1996

(65) Prior Publication Data

US 2002/0068815 A1 Jun. 6, 2002

Related U.S. Application Data

(60) Provisional application No. 60/001,713, filed on Jul. 28, 1995.

(51) Int. Cl.[7] .................................................. C12N 15/11
(52) U.S. Cl. .................................... 536/23.1; 536/24.1
(58) Field of Search ........................... 435/69.1, 320.1, 435/172.3, 325, 6; 536/23.1, 23.5, 24.1; 436/15; 514/44

(56) References Cited

U.S. PATENT DOCUMENTS 5,310,662 A  5/1994  Evans et al. ................ 435/64.1

OTHER PUBLICATIONS

Stanesh, Dictionary of Biochemistry and Molecular Biology, 2nd Edition, 1989, p. 490.*
Guo et al, Biochemical and Molecular Medicine 56: 8 (1995).*
Arn, P. et al. (1994) SRYX, A sex reversing locus in Xp21.2 to p22.11, Hum. Genet. 93:389–393 (Exhibit 2).
Baniahmad, A. et al. (Jun. 1994) The nuclear hormone receptor superfamily in: M.–J. Tsai and B.W. O'Malley, eds., Mechanism of Steroid Hormone Regulation of Gene Transcription, Austin: R.G. Landis, 1–24 (Exhibit 3).
Bardoni, B. et al. (1994) A dosage sensitive locus at chromosome Xp21 is involved in male to female sex reversal, Nat. Genet. 7:497–501 (Exhibit 4).
Brown, T. R. et al. (1990) Mol. Endocrinol. 4:1759–1772 (Exhibit 5).
Evans, R. M. (1988) The steroid and thyroid hormone receptor superfamily, Science 240:889–895 (Exhibit 6).

Gazder, A. F. et al. (1990) Establishment and characterization of a human adrenocortical carcinoma cell line that expresses multiple pathways of steroid biosynthesis, Cancer Res. 50:5488–5496 (Exhibit 7).
Golden, M. P. et al. (1977) Congenital adrenal hypoplasia and hypogonadotropic hypogonadism, Am. J. Dis. Child. 131:1117–1118 (Exhibit 8).
Goonewardena, P. et al. (1989) Molecular Xp deletion in a male: suggestion of a locus for hypogonadotropic hypogonadism distal to the glycerol kinase and adrenal hypoplasia loci, Clin. Genet. 35:5–12 (Exhibit 9).
Guo, W. et al. (1993) Genomic scanning for expressed sequences in Xp21 identifies the glycerol kinase gene, Nature Genet. 4:367–372 (Exhibit 10).
Guo, W. et al.
Hay, I.D. et al. (1981) Familial cytomegalic adrenocortical hypoplasia: an X–linked syndrome of pubertal failure, Arch Dis. Child. 56:715–721 (Exhibit 12).
Kelch, R. P. et al. (1984) Congenital adrenal hypoplasia, Pediatr. Adolesc. Endocrinol. 13:156–161 (Exhibit 13).
Kletter, G. B. et al. (1991) Congenital adrenal hypoplasia and isolated gonadotropin deficiency, Trends Endoc. Metab. 2:123–128 (Exhibit 14).
Laudet, V. et al. (1992) Evolution of the nuclear receptor gene superfamily, EMBO J. 11:1003–1013 (Exhibit 15).
Lubahn, D. B. et al. (1989) Proc. Natl. Acad. Sci. USA 86:9534–9538 (Exhibit 16).
Luo, X. et al. (1994) A cell–specific nuclear receptor is essential for adrenal and gonadal development and sexual differentiation, Cell 77:481–490 (Exhibit 17).
Marcelli, M. et al. (1990A) J. Clin. Invest. 85:1522–1528 (Exhibit 18).
Marcelli, M. et al. (1990B) Mol. Endocrinol. 4:1105–1116 (Exhibit 19).
Marcelli, M. et al. (1991) J. Clin. Invest. 87:1123–1126 (Exhibit 20).
McCabe, E.R.B. (1995) Disorders of glycerol metabolism. In: Scriver CR, Beaudet AL, Sly WS, Valle D, eds. The Metabolic Basis of Inherited Disease, 7th ed., New York, McGraw–Hill, 1631–1652 (Exhibit 21).
McPhaul, M. J. et al. (1991) FASEB J. 5:2910–2915 (Exhibit 22).
McPhaul, M. J. et al. (1994) In: M. Parker, ed. Steroid Hormone Action, New York IRL Press, New York 186–208 (Exhibit 23).

(List continued on next page.)

Primary Examiner—James Martinell
(74) Attorney, Agent, or Firm—Mandel & Adriano

(57) ABSTRACT

The invention provides a DAX-1 protein molecule having the amino acid sequence beginning with methionine at position 1 and ending with isoleucine at position 470 as shown in FIG. 12. The invention further provides the genomic nucleic acid sequence for DAX-1, including intron, exons and a promoter region. Additionally, the invention provides methods for using and making the DAX-1 protein and DAX-1 nucleic acid molecules.

3 Claims, 38 Drawing Sheets

OTHER PUBLICATIONS

Migeon, C.J., Donohoue P. (1994) in: M.S. Kappy et al., eds. Wilkins—The Diagnosis and Treatment of Endocrine Disorders in Childhood and Adolescence, 4th ed.,Springfield: Thomas 717–856 (Exhibit 24).

Mullen, C.A. (1994) Pharmac. Ther. 63:199–207 (Exhibit 25).

Partsch, C–J, Sippell, W. G. (1989) Hypothalamic hypogonadism in congenital adrenal hypoplasia, Horm. Metabol. Res. 21:623–625 (Exhibit 26).

Rosenfeld, M. et al. (1991) Adenovirus–mediated transfer of a recombinant $\alpha_1$–antitrypsin gene to the lung epithelium in vivo, Science 252:431 (Exhibit 27).

Schena, M. and Yamamoto, K. R. (1988) Mammalian glucocorticoid receptor derivatives enhance transcription in yeast, Science 241:965–967 (Exhibit 28).

Seltzer, W.K. et al. (1985) Adrenal dysfunction in glycerol kinase deficiency, Biochem. Med. 33:189–199 (Exhibit 29).

Walker, A. P. et al. (1993) Isolation of the human Xp21 glycerol kinase gene by positional cloning, Hum. Mol. Genet. 2:107–114 (Exhibit 30).

Wang, L. H. et al. (1989) COUP transcription factor is a member of the steroid receptor superfamily, Nature 340:163–166 (Exhibit 31).

Worley, K.C. et al. (1992) Identification of the three new markers in Xp21 between DXS28 (C7) and DMD, Genomics 13:957–961 (Exhibit 32).

Worley, K.C. et al. (1993) Yeast artificial chromosome cloning in the glycerol kinase and adrenal hypoplasia congenita region of Xp21, Genomics 16:407–416 (Exhibit 33).

Yates, J.R.W. et al. (1987) A deletion of Xp21 maps congenital adrenal hypoplasia distal to glycerol kinase deficiency, Cytogenet. Cell Genet. 46:723 (Exhibit 34).

Zanaria, E. et al. (1994) An unusual member of the nuclear hormone receptor superfamily responsible for X–linked adrenal hypoplasia congenita, Nature 372:635–641 (Exhibit 35).

Guo et al., "Diagnosis of X–linked Adrenal Hypoplasia Congenita By Mutation Analysis off the DAX1 Gene", Journal of the American Medical Association, vol. 274, No. 04, Jul. 26, 1995; pp. 324–330.

Muscatelli et al., "Mutations in the DAX–1 Gene Give Rise to Both X–linked Adrenal Hypoplasia Congenita and Hypogonadotropic Hypogonadism", Nature, vol. 372, Dec. 15, 1994, pp. 672–676.

* cited by examiner

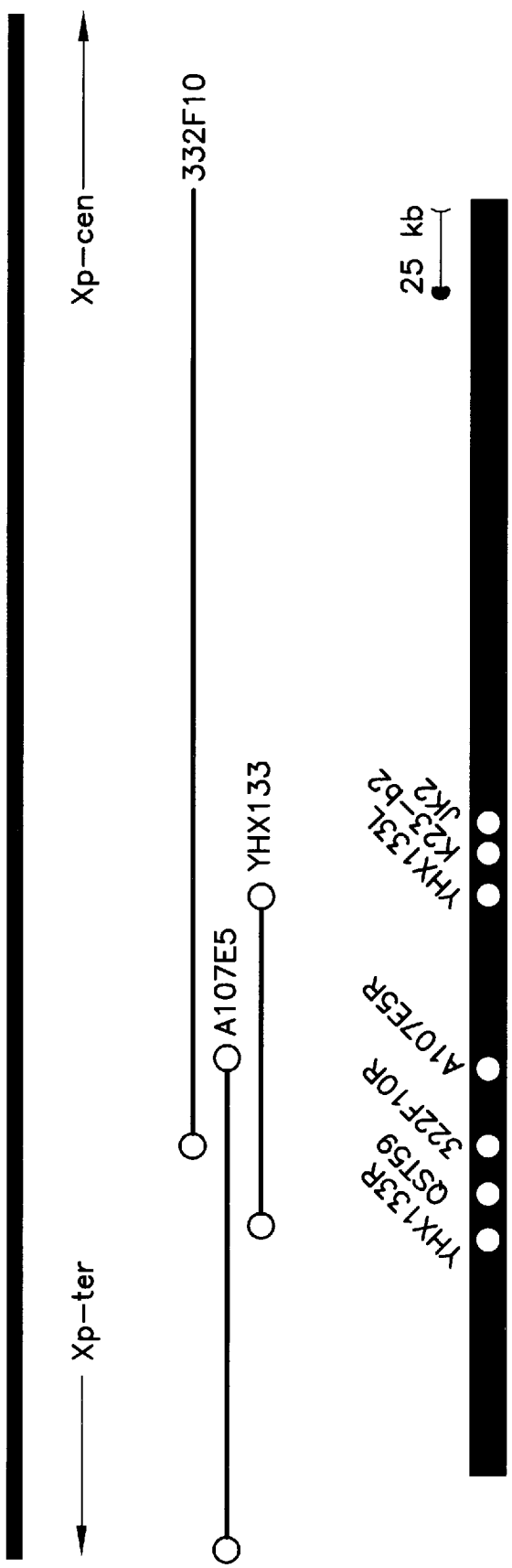
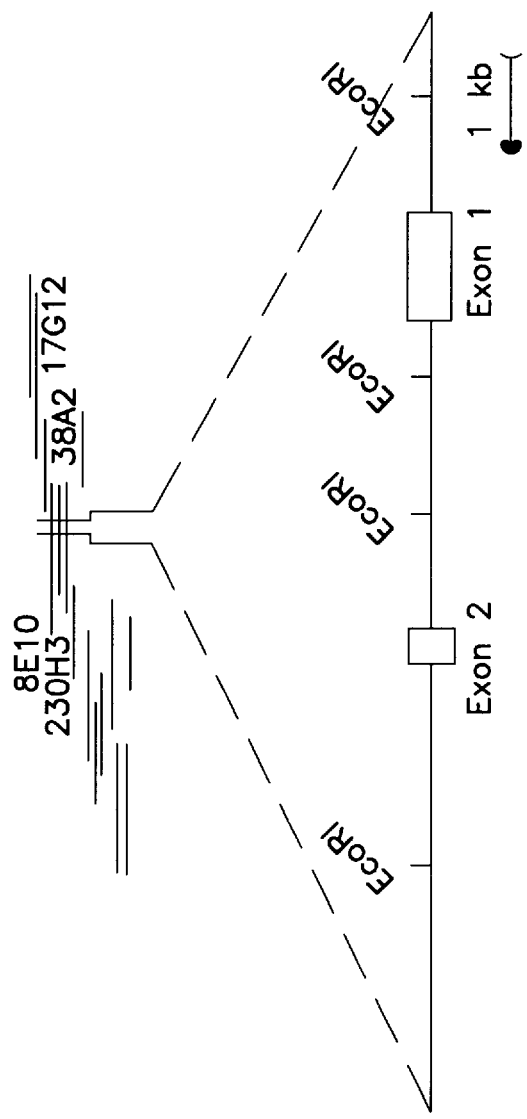
FIG. 1

FIG. 2B

```
         ...E    L    N    S    T    L    F    L    L    R    F...
Normal 1282 GAACTTAATAGTACCCTTTCCTGCTGAGATTC 1314
P1 and P2 1282 GAACTTAATATACCCTTTCCTGCTGAGATTC 1313
         ...E    L    N    I    P    F    S    C    *...
```

```
GAATTCCAGGTCCTGGAGAAGACGAAAAAGAGAAAGAGAAGGAGAAGGAGAGTGAG    -1520
AGAGGGAGGGAGGGAAGGAAGGAAGGAAGGAAGGAAGGAAGGAAGGAAAGGAA       -1460
GGAAGGAAGGAAGGAAGGAAGGAAGGAAGGAGGGAGGGAAGGAAGGAAGGA         -1400
AGGAAAAGAAACAGCAAAAAAAGAAAAGAGGGAGGATGGGAGGGAGGGAAAAGTAAAAT -1340
GATTCTGTATCAGCTGTGAAGACTAATGGATCCAGGCTTCCTGATGCTTCTATTTTATCATTATTCACTT -1280
TGGCAAGTGAAGACTAATGGATCCAGGCTTCCTGATGCTTCTATTTTATCATTATTCACTT -1280
AGGAAGGGTGGGAAAAGAACAGAAAAACCAAATATCACATGTTCTCACTTGGGAGCTAAA -1220
TCAAAATTTCTCACTGCGGCCATGAAAACCAAATATCACATGTTCTCACTTGGGAGCTAAA -1160
AAGTAATGCAGGAACAGAACAACCAAATATCACATGTTCTCACTTGGGAGCTAAA     -1100
GAGGGTGGGAAGAGGGAGAATGAGAAAAATACCTATTGGATACTACCTGGTGA       -1040
TGAAATAATCTGTACACCAAACCCCACGACAAGCAATTCACTTATATAACAAACCCGCA -980
CATGTACTCCTGAACCTAAATATTATCCCCTCGTAATTATTATTCCTAAGTTTTAGGCACTTTT -920
TCTCACTGTAACAATATTATCCCCTCGTAATTATTATTCCTAAGTTTTAGGCACTTTT -860
ACATCCTGCTCGCTGCCCCCAGCTCTCTTAACACAGCATCCAGGACATAGTGGGCGCTTA -800
TAAATACTGATGGCATTAAACTGAGCGCTTATGATAGCATATTTAGAGGAGTGCTTCACA -740
AACGTCTAGGTGCATGTGACTCCCTGGGACACCGATAAATGGAGATTCAGAGTTAGAA -680
AGTCTGGGGGCCTGAGATTGGACATTTCCACCGAGCCCCATGATGCTTGTCTAT      -620
GTTCTGTATTTCACAAGGTCTCAGAAATGAAGTTTACAAAGAGCATAGGAAGTAGATGTTTCCT -560
CACACAAACTGTGATAATTTAATGAAAGTTTACAAAGAGCATAGGAAGTAGATGTTTCCT -500
CTTTTCCCCTGCCCCTCCCAATAAAGGGAACAAATTAGATGCGAGGGTTCAATGGAAAGAG -440
```

FIG. 7B

TETRA-NUCLEOTIDE REPEATS

```
TTGCAACAGGAGCATCCAGGGGCTCGCTCTCCTCCGGTCTTCCTGAGACAGGGAAAGGGTAA  -260
                                          →Published in Zanaria
TGAGAGGAAGGAGAAAGTGTCCAGAGCTCCCACGCTGTGTTCTTCCATTTCCAGCTT       -200
                        SF-1
TTAAAGAGCACCCGGCCCCTTGAACCACCAGAGTCATGGCGAACACACGGAGCGCAGA      -140
               GC
CCGGCGCCCCCGCACACAGGGCCGGCCTCGCGGCGCTCCTTGCCCAGACCCTGCAGGGGGCGAC -80
CGCGCTGGCTGCGCGCTAGTATAAATAGGTCCAGGAGGCAGCCACTGGGCAGAACTGG      -20
GCTACCGGGGCGCCGCCATGGCGGGCCAGAACCACCAGTGGCAGGCAGCATCCTCTA        41
                 M  A  G  Q  N  H  Q  W  Q  G  S  I  L  Y
CAACATGCTTATGAGCGCGAAGCAAACGCGCGCGGCTCCTGAGGCTCCAGAGACGCGGCT    101
 N  M  L  M  S  A  K  Q  T  R  A  A  P  E  A  P  E  T  R  L
GGTTGGATCAGTGTGTGGGCTGTCGTGGTGCGATGAGCCGGGCGATGAGCCGGGCAGAGAGGGCT 161
 V  D  Q  C  W  G  C  S  G  D  E  P  G  V  G  R  E  G  L
GCTGGGGCGGCCGGAACGTGGCGCTCCTGTACCGCTGCTGTTTGCGTAAAGACCAC        219
 L  G  G  R  N  V  A  L  L  Y  R  C  C  F  C  G  K  D  H
```

FIG. 7B (CONT'D)

Region II

```
              E  A  A  S  A  G  L  L  K  T  L  R  F  V  K  Y  L  P  C  F  Q  V  L  P  L  D  Q  Q  L  V  L  V  R  N  C  W  A  S  L  L  M  L
DAX-1         E  A  A  S  A  G  L  L  K  T  L  R  F  V  K  Y  L  P  C  F  Q  V  L  P  L  D  Q  Q  L  V  L  V  R  N  C  W  A  S  L  L  M  L   297
hTR2-11       -  S  -  -  R  L  -  -  F  L  S  M  H  W  A  L  S  -  -  S  -  -  A  -  G  Q  E  N  S  -  S  -  -  K  A  Y  -  N  E  -  F  T  -   436
hCOUP-TFI     -  L  -  -  A  R  L  -  -  F  S  A  V  E  W  A  R  N  -  -  -  F  -  P  D  -  Q  -  T  D  -  V  S  -  L  -  L  T  -  S  E  -  F  V  -   262
hRAR          -  L  S  T  K  C  L  -  -  -  V  E  F  A  -  Q  -  -  G  -  T  T  -  T  L  A  D  -  -  T  -  L  K  A  A  C  L  D  -  -  -  -   271
hRXR          Q  -  -  D  K  Q  -  -  F  T  L  V  E  W  A  -  R  -  -  -  H  -  S  E  -  -  D  -  V  -  -  A  G  -  N  E  -  -  -  A  -  -   313
hTR           K  -  -  T  P  A  -  T  R  V  V  D  -  A  -  K  -  -  -  M  -  C  E  -  -  D  -  L  -  L  K  G  -  C  M  E  -  M  S  -  -  -   310
hERR2         D  L  -  -  D  R  E  -  V  F  L  -  S  -  -  W  A  -  H  -  -  -  G  -  S  N  -  -  T  L  G  D  -  M  S  -  -  Q  S  A  -  M  E  -  -  -  -   286
mSF1          R  M  -  D  Q  T  F  -  S  L  -  V  D  W  A  R  R  C  M  V  -  -  K  E  -  -  E  V  A  D  -  M  T  -  M  T  -  -  L  Q  -  -  S  E  -  -  -   309
rHNF4         -  S  M  K  E  Q  -  -  -  V  L  V  E  W  A  -  -  -  -  -  L  -  -  -  -  -  D  -  V  A  -  L  -  A  H  A  G  E  H  -  L  -   221
mGCNF         R  L  -  D  E  L  -  F  R  Q  -  A  W  L  -  -  K  -  -  -  F  -  C  E  -  S  -  K  D  Y  T  C  -  L  S  S  T  -  Q  E  -  -  -   345
hVDR          D  L  V  -  Y  S  L  Q  -  V  L  V  R  Q  -  A  -  M  -  -  -  G  -  R  D  -  T  S  E  D  -  -  -  -  K  S  S  A  L  E  V  -  -   273
hMR           R  L  -  G  K  Q  M  I  Q  V  V  K  W  A  K  -  V  -  -  G  -  K  N  -  -  E  D  -  -  -  T  -  Q  Y  S  -  M  C  -  S  S  F   812
hGR           M  L  G  G  R  Q  V  I  A  A  V  K  W  A  K  A  -  -  G  -  R  N  -  -  D  -  -  M  T  -  L  Q  Y  S  -  M  F  -  M  A  F   606
hPR           Q  L  G  E  R  Q  -  -  S  V  V  K  W  S  -  S  -  -  -  G  -  R  N  -  -  H  -  -  T  -  L  Q  Y  S  -  M  -  M  V  F   761
hAR           -  L  G  E  R  Q  -  I  V  H  V  V  K  W  A  K  A  -  -  G  -  R  N  -  -  H  -  V  -  D  -  M  A  V  -  Q  Y  S  -  M  G  -  M  V  F   747
hER           N  L  -  D  R  E  -  V  H  M  I  N  W  A  -  R  V  -  G  -  V  D  -  T  -  H  D  -  V  H  -  L  E  C  A  -  L  E  -  -  -  -   389
```

FIG. 8B

Region III

```
DAX-1     C W S L N I   S T K E Y A Y L K G T V L F N P D   390
hTR2-11   M V K - C - D G Y - - - - A I - - - - S - -         511
hCOUP-TFI L K A - H V D S A - - - A I - - - T S - -           331
hRAR      L L P - E M D D A - T G L - S A I C - C G - -       338
hRXR      M R D M Q M D K T - L G C - R A I C - - - -         381
hTR       L S - F - L D D T - V - L - Q A V L - M S S - -     377
hERR2     Y K K - K V E K E - F V M - - A L A - S - -         353
mSF1      L H A - Q L D R Q - F V C - - F L I - S L - -       381
rHNF4     F Q E - Q - D D N - - - A I - F - D - -             289
mGCNF     F H Q - K V - N E - - - C M - A I N F L - Q - -     416
hVDR      L K K - L H E E - H V L - M A I C I V S I - -       342
hMR       F V R - Q L T F E - T - M - V L L - L S T I -       882
hGR       L H R - Q V - Y E - L C M - T L L - L S S V -       676
hPR       F V K - Q V - Q E - F L C M - V L L - T -           831
hAR       F G W - Q - T P Q - F L C M - A L L - - S I -       816
hER       F R M M - L Q G E - F V C - - S I - - L - S -       457
```

```
            GAGCTCCCACGCTGCTGTTCTTCCATTTCCAGCTTTTAAAGAGCACCCGCCCCT   54

TCGAACCACCGAGGTCATGGGCGAACACACCGGAGCGCAGACCGCGCCCCCCCGCACACA   114

CCGCCCGCCTCCGCGCCCTTGCCCAGACCGAGGCGGCCGACGCGCCTGCGTGCGCGCTAG   174

──────1AF─────▶
GTATAAATAGGTCCCAGGAGGCAGCCACTGGGCAGAACTGGGCTACGGGCGCCGCGGGCC   234

ATGGCGGGCGAGAACCACCAGTGGCAGGGCAGCATCCTCTACAACATGCTTATGAGCGCG   294
 M  A  G  E  N  H  Q  W  Q  G  S  I  L  Y  N  M  L  M  S  A    20

AAGCAAACGCGCGCGGCTCCTGAGGCTCCAGAGACGCGGCTGGTGGATCAGTGTTGGGGC   354
 K  Q  T  R  A  A  P  E  A  P  E  T  R  L  V  D  Q  C  W  G    40

TGTTCGTGCGGCGATGAGCCCGGGGTGGGCAGAGAGGGGCTGCTGGGCGGGCGGAACGTG   414
 C  S  C  G  D  E  P  G  V  G  R  E  G  L  L  G  G  R  N  V    60

GCGCTCCTGTACCGCTGCTGCTTTTGCGGTAAAGACCACCCACGGCAGGGCAGCATCCTC   474
 A  L  L  Y  R  C  C  F  C  G  K  D  H  P  R  Q  G  S  I  L    80

──────1AaF─────▶
TACAGCATGCTGACGAGCGCAAAGCAAACGTACGCGGCACCGAAGGCGCCCGAGGCGACG   534
 Y  S  M  L  T  S  A  K  Q  T  Y  A  A  P  K  A  P  E  A  T   100

CTGGGTCCGTGCTGGGGCTGTTCGTGCGGCTCTGATCCCGGGGTGGGCAGAGCGGGGCTT   594
 L  G  P  C  W  G  C  S  C  G  S  D  P  G  V  G  R  A  G  L   120

CCGGGTGGGCGGCCCGTGGCACTCCTGTACCGCTGCTGCTTTTGTGGTGAAGACCACCCG   654
 P  G  G  R  P  V  A  L  L  Y  R  C  C  F  C  G  E  D  H  P   140

CGGCAGGGCAGCATCCTCTACAGCTTGCTCACTAGCTCAAAGCAAACGCACGTGGCTCCG   714
 R  Q  G  S  I  L  Y  S  L  L  T  S  S  K  Q  T  H  V  A  P   160
```

FIG. 12B

```
GCAGCGCCCGAGGCACGGCCAGGGGGCGCGTGGTGGGACCGCTCCTACTTCGCGCAGAGG    774
 A   A   P   E   A   R   P   G   G   A   W   W   D   R   S   Y   F   A   Q   R    180

CCAGGGGGTAAAGAGGCGCTACCAGGCGGGCGGGCCACGGCGCTTCTGTACCGCTGCTGC    834
 P   G   G   K   E   A   L   P   G   G   R   A   T   L   L   Y   R   C   C        200

◄——— 1AaR ———
TTTTGCGGTGAAGACCACCCGCAGCAGGGCAGCACCCTCTACTGCGTGCCCACGAGCACA    894
 F   C   G   E   D   H   P   Q   Q   G   S   T   L   Y   C   V   P   T   S   T    220

——— 2875 ——►
AATCAAGCGCAGGCGGCTCCGGAGGAGCGGCCGAGGGCCCCCTGGTGGGACACCTCCTCT    954
 N   Q   A   Q   A   A   P   E   E   R   P   R   A   P   W   W   D   T   S   S    240

GGTGCGCTGCGGCCGGTGGCGCTCAAGAGTCCACAGGTGGTCTGCGAGGCAGCCTCAGCG   1014
 G   A   L   R   P   V   A   L   K   S   P   Q   V   V   C   E   A   A   S   A    260

◄——— 2874 ———
GGCCTGTTGAAGACGCTGCGCTTCGTCAAGTACTTGCCCTGCTTCCAGGTGCTGCCCCTG   1074
 G   L   L   K   T   L   R   F   V   K   Y   L   P   C   F   Q   V   L   P   L    280

GACCAGCAGCTGGTGCTGGTGCGCAACTGCTGGGCGTCCCTGCTCATGCTTGAGCTGGCC   1134
 D   Q   Q   L   V   L   V   R   N   C   W   A   S   L   L   M   L   E   L   A    300

◄——— 1AR ———
CAGGACCGCTTGCAGTTCGAGACTGTGGAAGTCTCGGAGCCCAGCATGCTGCAGAAGATC   1194
 Q   D   R   L   Q   F   E   T   V   E   V   S   E   P   S   M   L   Q   K   I    320

CTCACCACCAGGCGGCGGGAGACCGGGGGCAACGAGCCACTGCCCGTGCCCACGCTGCAG   1254
 L   T   T   R   R   R   E   T   G   G   N   E   P   L   P   V   P   T   L   Q    340

CACCATTTGGCACCGCCGGCGGAGGCCAGGAAGGTGCCCTCCGCCTCCCAGGTCCAAGCC   1314
 H   H   L   A   P   P   A   E   A   R   K   V   P   S   A   S   Q   V   Q   A    360

ATCAAGTGCTTTCTTTCCAAATGCTGGAGTCTGAACATCAGTACCAAGGAGTACGCCTAC   1374
 I   K   C   F   L   S   K   C   W   S   L   N   I   S   T   K   E   Y   A   Y    380
```

FIG. 12C

```
                          CCCGGgtaagggtac......ctccctccagACGTG
CTCAAGGGGACCGTGCTCTTTAACCCGGACGTGCCGGGCCTGCAGTGCGTGAAGTACATT 1434
L   K   G   T   V   L   F   N   P   D   V   P   G   L   Q   C   V   K   Y   I    400

CAGGGACTCCAGTGGGGAACTCAGCAAATACTCAGTGAACACACCAGGATGACGCACCAA 1494
Q   G   L   Q   W   G   T   Q   Q   I   L   S   E   H   T   R   M   T   H   Q    420

GGGCCCCATGACAGATTCATCGAACTTAATAGTACCCTTTTCCTGCTGAGATTCATCAAT 1554
G   P   H   D   R   F   I   E   L   N   S   T   L   F   L   L   R   F   I   N    440

GCCAATGTCATTGCTGAACTGTTCTTCAGGCCCATCATCGGCACAGTCAGCATGGATGAT 1614
A   N   V   I   A   E   L   F   F   R   P   I   I   G   T   V   S   M   D   D    460

ATGATGCTGGAAATGCTCTGTACAAAGATATAAAGTCATGTGGGCCACACAAGTGCAGTA 1674
M   M   L   E   M   L   C   T   K   I   *                                        470

GTGCAGTTCACCATGAGGGAAGAATAAAGAGCTGTGGGCAAAAGAGTGTAAAATATTTTA 1734
                            ▼
AAATAAACTTTCTTAATATTTTTACATGCAGAGTATTTTGATCTTCAATTAAAGAAATAA 1794

TTTTATTCCCAGCACAGTCACAAATTTCTCTGTTCCATAGTTAAAGAAGACATTTGCCAA 1854

CAGGTAGCATAGCTCTGTACATCTTTTAAAAAAAAAATCGCAGGGTACTAGTATAATAAG 1914

CTATTTTCACAAGCGCAGCAATTTCATGGAACCTGCTCAAATCAAATTTGTACATATTGT 1974

TATAATAAATTTTAAGGTCTTAACTATTAACTTGATTGAAAAAGCTT                  2022
```

FIG. 20A

Region II

| | | | | | | | | | | | | | | | | | | | | | | | | | | |
|---|---|---|---|---|---|---|---|---|---|---|---|---|---|---|---|---|---|---|---|---|---|---|---|---|---|---|
| hDAX-1 | E | A | A | S | A | G | L | L | K | T | L | R | F | V | K | Y | L | P | C | F | Q | V | L | P | L | D | Q | Q | L | V | L | V | R | N | C | W | A | S | L | L | M | L | 297 |
| rHNF4 | - | S | M | K | E | Q | - | - | V | L | V | E | W | A | - | - | I | - | A | - | C | E | - | L | - | D | - | V | A | - | - | I | - | A | H | A | G | E | H | - | I | A | 221 |
| hRXR | Q | - | - | D | K | Q | - | - | F | T | L | V | E | W | A | - | R | H | - | S | E | - | - | H | - | D | - | V | I | - | - | L | - | A | G | N | E | - | - | F | T | 313 |
| hTR2-11 | - | S | - | - | R | L | - | - | F | L | S | M | H | W | A | L | S | I | - | - | S | - | - | - | A | - | D | - | N | S | I | S | - | K | A | Y | N | E | - | - | F | V | 436 |
| hCOUP-TFI | - | L | - | A | R | L | - | - | F | S | A | V | E | W | A | R | N | I | - | - | F | - | P | D | - | D | - | V | S | - | - | L | - | L | T | S | E | - | M | - | H | I | 262 |
| hRAR | - | L | S | T | K | C | I | I | - | - | V | E | F | A | - | - | Q | - | - | G | - | T | T | - | T | H | - | A | D | - | - | H | I | T | K A A C L D I H - - - - 271 |
| hTR | K | I | T | P | A | - | T | R | V | V | D | - | A | - | K | - | - | M | - | C | E | - | - | M | - | D | - | H | I | - | - | L | K G - C M E H M H - - - - 310 |
| hERR2 | D | L | - | D | R | E | - | - | V | F | L | I | S | W | A | - | H | H | - | G | - | S | N | - | T | L | G | D | - | - | M | S | - | L Q S A - - M E H M S - - - 286 |
| mSF1 | R | M | - | D | Q | T | F | I | S | I | V | D | W | A | R | R C M V - - K E - E V A D - - M T - L Q Q S - - S E - - Q E - - I - - - 309 |
| mGCNF | R | L | - | D | E | L | - | - | F | R | Q | I | A | W | I | - | K | - | - | F | - | C | E | - | - | S | I | K | D | - | - | H | - | L | S | S | A | I | E | V | I | - | 345 |
| hVDR | D | L | V | - | Y | S | I | Q | - | V | I | G | - | A | - | - | M | - | G | - | R | D | - | T | S | E | D | - | E | D | - | - | I | T | - | I | Q | Y | S | - | M | C | 273 |
| hMR | R | L | - | G | K | Q | M | I | Q | V | V | K | W | A | - | - | V | - | - | G | - | K | N | - | - | E | D | - | - | D | - | - | M | T | - | I | Q | Y | S | - | M F - - - 812 |
| hGR | M | L | G | G | R | Q | V | I | A | A | V | K | W | A | - | - | A | I | - | - | G | - | R | N | - | - | H | - | - | D | - | - | I | T | - | L | I | Q | Y | S | - | M | 606 |
| hPR | Q | L | G | E | R | Q | - | - | S | V | V | K | W | S | - | - | S | - | - | G | - | R | N | - | - | H | - | - | D | - | - | M | T | - | H | I | Q | Y S - M G - - - 761 |
| hAR | - | L | G | E | R | Q | - | - | V | H | V | V | K | W | A | - | - | A | - | - | G | - | R | N | - | - | H | V | - | - | D | - | - | M | A | V | I | Q | Y S - M V F - - - 747 |
| hER | N | L | - | D | R | E | - | - | V | H | M | I | N | W | A | - | R | V | - | - | G | - | V | D | - | T | - | H | D | - | V | H | - | L | E | C | A | - | L | E | I | - | H | 389 |

FIG. 20B

Region III

| | | | | | | | | | | | | | | | | | | | | | | | | |
|---|---|---|---|---|---|---|---|---|---|---|---|---|---|---|---|---|---|---|---|---|---|---|---|---|
| hDAX-1    | C | W | S | L | N | I | S | T | K | E | Y | A | Y | L | K | G | T | V | L | F | N | P | D | 390 |
| rHNF4     | F | Q | E | – | Q | – | D | D | N | – | – | – | – | – | – | A | I | F | – | – | – | – | – | 289 |
| hRXR      | M | R | D | M | Q | M | D | K | T | – | L | G | – | – | – | R | A | I | – | – | S | – | – | 381 |
| hTR2-11   | M | V | K | – | C | – | D | G | Y | – | – | – | – | – | – | A | I | – | – | – | S | – | – | 511 |
| hCOUP-TFI | L | K | A | – | H | V | D | S | A | – | S | C | – | – | – | A | I | C | – | – | T | S | – | 331 |
| hRAR      | L | L | P | – | E | M | D | D | A | – | T | G | L | – | – | S | A | I | C | – | I | C | G | 338 |
| hRXR      | M | R | D | M | Q | M | D | K | T | – | L | G | – | – | – | R | A | I | – | – | – | – | – | 381 |
| hTR       | L | S | – | F | – | L | D | D | T | – | V | – | L | – | Q | A | V | L | – | M | – | S | S | 377 |
| hERR2     | Y | K | K | – | K | V | E | K | E | – | F | V | M | – | – | A | L | A | – | M | A | – | S | 353 |
| mSF1      | L | H | A | – | Q | L | D | R | Q | – | F | V | C | – | – | F | L | I | – | I | – | S | L | 381 |
| hVDR      | L | K | K | – | L | H | E | E | – | H | V | L | – | – | M | A | I | C | I | V | S | – | – | 342 |
| hMR       | F | V | R | – | Q | L | T | F | E | – | T | H | I | M | V | L | L | – | L | L | S | T | I | H | 882 |
| hGR       | L | H | R | – | Q | V | – | Y | E | – | L | L | C | M | – | T | L | L | – | L | L | S | S | V | 676 |
| hPR       | F | V | K | – | Q | V | – | Q | E | – | L | L | C | M | – | V | L | L | – | L | – | T | I | H | 831 |
| hAR       | F | G | W | – | Q | – | T | P | Q | – | F | L | C | M | – | A | L | L | – | L | – | S | I | I | 816 |
| hER       | F | R | M | M | – | L | Q | G | E | – | F | V | C | – | – | S | I | I | – | L | – | S | – | – | 457 |

FIG. 21

| | | | | | | | | | | | | | | | | | | | | | |
|---|---|---|---|---|---|---|---|---|---|---|---|---|---|---|---|---|---|---|---|---|---|
| DAX-1 | L | L | G | T | V | S | M | D | D | M | L | L | E | M | L | C | T | K | I | * | 470 |
| TRβ   | E | C | P | T | E | L | L | P | P | L | L | L | E | V | F | E | D | * |   |   | 456 |
| RARα  | M | E | L | G | P | S | M | P | P | M | L | Q | E | M | L | E | N | S | E | G | 419 |
| RXRα  | L | L | G | T | P | E | L | P | P | L | L | L | E | M | L | E | A | P | H | Q | 460 |
| PR    | R | A | L | S | V | V | F | E | D | F | M | S | E | M | L | A | A | Q | L | P | 918 |
| ER    | C | K | T | M | S | I | L | Y | P | L | L | M | E | V | L | Q | H | R | L | P | 549 |
| GR    | K | T | V | V | S | S | F | P | D | M | L | L | E | M | L | T | N | Q | I | P | 762 |
| AR    | H | M | H | V | D | K | F | P | P | M | M | A | E | M | L | S | A | Q | V | P | 903 |
| MR    | S | H | A | L | K | V | F | A | P | L | L | V | E | L | L | D | S | D | Q | L | 969 |

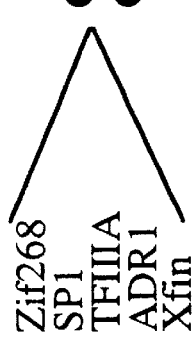

FIG. 22A

```
1   MAGQNHQWQGSILYNMLMSAKQTRAAPEAPETRLVDQCWGCSSGDEPGVGREGLLGGRNVALLYRCC
68  FC--KD-PR----S--T----Y---K---AT-.GP----SD----A--P--P--L
134 FC--D-PR----SL-T-S---HV--A--PGGAW-DR-YFAQRPG-K-A-P--AT--
201 FC--D-PQ---T--CVPT-TN-...QA---E-PRAPW-DT-S-ALRP-...A-KSP
```

FIG. 22B

DAX1    $CXXCXC..X_{22}..CXXC$

Zif268  
SP1     $CXXC..X_{12}..H.X_3.H$
TFIIIA  
ADR1    $C.X_4.C..X_{12}..H.X_3.H$
Xfin GAL4            $CXXC..X_6..C.X_6..CXXC..X_6..C$
GATA1           $CXXC..X_{17}..CXXC$
dsx             $CXXCXXH..X_8..HXXH.X_4.CXCXXC$
RING1           $CXXC..X_{12}..CXHXXCXXC..X_{11}..CXXC$
LIM             $CXXC..X_{16-23}..HXXCXXCXXC..X_{16-21}..C$
CRP             $CXXC..X_{17}..HXXCXXCXXC..X_{17}..CXXC$
Steroid         $CXXC..X_7..H.X_5..CXXC..X_{15}..C.X_5..C.X_9..CXXC..X_4..C$
Receptors

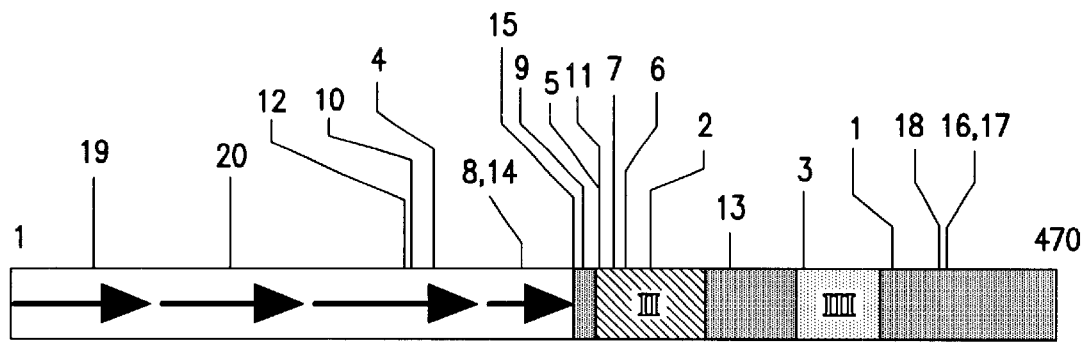

| Family | Patient | Mutation | Reference |
|---|---|---|---|
| 1. | M.A. | FRAMESHIFT (complex deletion/insertion) | Muscatelli et al., 1994 |
| 2. | M.T. C.B. | Q283X | Muscatelli et al., 1994 |
| 3. | A.O. L.S. | W369X | Muscatelli et al., 1994 |
| 4. | L.B. L.M. | FRAMESHIFT (549insT) | Muscatelli et al., 1994 |
| 5. | B.R. | L263X | Muscatelli et al., 1994 |
| 6. | 2115 | dV269 | Muscatelli et al., 1994 |
| 7. | 2687 2688 | R267P | Muscatelli et al., 1994 |
| 8. | 2065 | W235X | Muscatelli et al., 1994 |
| 9. | 2791 | FRAMESHIFT (784delAA) | Muscatelli et al., 1994 |
| 10. | 3743 3744 | W172X | Muscatelli et al., 1994 |
| 11. | 3741 | FRAMESHIFT (796insCAGG) | Muscatelli et al., 1994 |
| 12. | 2094 | FRAMESHIFT (507CG-T) | Muscatelli et al., 1994 |
| 13. | M.I.N. M.E.N. | FRAMESHIFT (983delCACCTGTGGAC) | Zanaria et al, 1994 |
| 14. | B.F. | W235X | Zanaria et al., 1994 |
| 15. | 2957 | FRAMESHIFT (779insACCC) | Zanaria et al., 1994 |
| 16. | R.E. | FRAMESHIFT (1292delT) | Guo et al., 1995 |
| 17. | T.P. | FRAMESHIFT (1292delT) | Guo et al., 1995 |
| 18. | D.P. | FRAMESHIFT (1265insCC) | Guo et al., submitted |
| 19. | J.L.B. | FRAMESHIFT (153delGA) | Guo et al., submitted |
| 20. | P.S. R.H. | Y91X | Guo et al., submitted |

FIG. 23

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 1798 base pairs
      (B) TYPE: nucleic acid
      (C) STRANDEDNESS: double
      (D) TOPOLOGY: linear (ii) MOLECULE TYPE: cDNA (ix) FEATURE:
    (A) NAME/KEY: Coding Sequence
    (B) LOCATION: 1580...1798
    (D) OTHER INFORMATION:

(xi) SEQUENCE DESCRIPTION: SEQ ID NO: 1:

```
GAATTCCAGG TCCTGGAGAA GACGAAAAAG AGAAAGAAAG AGAGAGAGAG AAGGAGTGA   60

AGAGGGAGGG AGGGAGGGAG GGAGGGAGGA AGGAAGGAAG GAAGGAAGGA AGGAAAGG   120

GGAAGGAAGG AAGGAAGGAA GGAAAGGAAG GAAGGAAGGA AGGAAGGAAG GAAGGAAG   180

AGGAAAAGAA ACAGCAAAAA AGAAAGAGG GAGGATGGGA GGGAGGGAAA AAGTAAAA    240

GATTCTGTAT CAGCTGGTAT ATACCAACAC CCTTCCCTGC CCCATGTCTT CACAGCTG   300

TGGCAAGTGA AGACTAATGG ATCCAGGCTT CCTGATGCTT CTATTTATCA TTATTCAC   360

AGGAAGGGTG GGAAAAGAAA TACTAATTAC ACACTTACCA ATGGAATACT TTTACAAG   420

TCAAAATTTC TCACTGCGGC CATGAAAAAG AATGAGAGCT GGCGGCCATC ATGCTTAG   480

AAGTAATGCA GGAACAGAAA ACCAAATATC ACATGTTCTC ACTTGGAAGT GGGAGCTA   540

TAAAGAGATC ACCTGGACAC TAGGAGGGGA ACAACAGACA CTGGAACCTC CTTGAAGG   600

GAGGGTGGGA AGAGGGAGAG AATGAGAAAA AATACCTATT GGATACTATT ACCTGGGT   660

TGAAATAATC TGTACACCAA ACCCCCACGA CAAGCAATTC ACTTATATAA CAAACCCG   720

CATGTACTCC TGAACCTAAA AGTTAAAAGA AAAAAAAATA TATACTAAAA TGAAAACA   780

TCTCACTGTA ACAATATTAT CCCCTCGTAA TTATTATATT CCTAAGTTTA GGCACTTT   840

CATCCTGCTC GCTGCCCCCA GCTCTCTTAA CACAGCATCC AGGACATAGT GGGCGCTT   900

AAATACTGAT GGCATTAAAC TGAGCGCTTA TGATAGCATA TTTAGAGGAG TGCTTCAC   960

ACGTCTAGGT GCATGTGACT CCCTGGGGAC ACCGATAAAA TGGAGATTCA GAGTTAG   1020

GTCTGGGGGG GGCCTGAGAT TTGGACATTT CCACCGAGCC CCATATGAT GCTTGTC   1080

GTTCTGTATT TCACAAGGTC TCAGAAAATG AGACCTCCCT ATCCATATAC AAATATA   1140

CACACAAACT GTGATAATTT AATGAAAGTT TACAAAGAGC ATAGGAAGTA GATGTTT   1200

CTTTTCCCCT GCCCTCCCAA TAAAGGGAAC AAATTAGATG CGAGGGTTCA ATGGAAA   1260

TTGCAACAGC ATCCAGGCGC TCGCTCTCCT CCGGTCTTCC TGAGACAGGG AAAGGGG   1320

TGAGAGGAAG GAGGAAAGTG TCCAGGAGCT CCCACGCTGC TGTTCTTCCA TTTCCAG   1380

TTAAAGAGCA CCCGCCCCTT CGAACCACCG AGGTCATGGG CGAACACACC GGAGCGC   1440

CCGCGCCCCC CCGCACACAC CGCCCGCCTC CGCGCCCTTG CCCAGACCGA GGCGGCC   1500

GCGCCTGCGT GCGCGCTAGG TATAAATAGG TCCCAGGAGG CAGCCACTGG GCAGAAC   1560

GCTACGGGCG CCGCGGGCC ATG GCG GGC CAG AAC CAC CAG TGG CAG GGC A   1612
                      Met Ala Gly Gln Asn His Gln Trp Gln Gly Ser
                       1               5                    10

ATC CTC TAC AAC ATG CTT ATG AGC GCG AAG CAA ACG CGC GCG GCT CC   1660
Ile Leu Tyr Asn Met Leu Met Ser Ala Lys Gln Thr Arg Ala Ala Pro
                15                  20                  25

GAG GCT CCA GAG ACG CGG CTG GTG GAT CAG TGT TGG GGC TGT TCG TG   1708
Glu Ala Pro Glu Thr Arg Leu Val Asp Gln Cys Trp Gly Cys Ser Cys
        30                  35                  40

GGC GAT GAG CCC GGG GTG GGC AGA GAG GGG CTG CTG GGC GGG CGG AA   1756
Gly Asp Glu Pro Gly Val Gly Arg Glu Gly Leu Leu Gly Gly Arg Asn
    45                  50                  55
```

```
        GTG GCG CTC CTG TAC CGC TGC TGC TTT TGC GGT AAA GAC CAC           1798
        Val Ala Leu Leu Tyr Arg Cys Cys Phe Cys Gly Lys Asp His
        60                  65                  70

(2) INFORMATION FOR SEQ ID NO: 2:

(i) SEQUENCE CHARACTERISTICS:
        (A) LENGTH: 73 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 2:

Met Ala Gly Gln Asn His Gln Trp Gln Gly Ser Ile Leu Tyr Asn Met
   1               5                  10                  15

Leu Met Ser Ala Lys Gln Thr Arg Ala Ala Pro Glu Ala Pro Glu Thr
                   20                  25                  30

Arg Leu Val Asp Gln Cys Trp Gly Cys Ser Cys Gly Asp Glu Pro Gly
                   35                  40                  45

Val Gly Arg Glu Gly Leu Leu Gly Gly Arg Asn Val Ala Leu Leu Tyr
                   50                  55                  60

Arg Cys Cys Phe Cys Gly Lys Asp His
                   65                  70

(2) INFORMATION FOR SEQ ID NO: 3:

(i) SEQUENCE CHARACTERISTICS:
        (A) LENGTH: 2022 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 235...1644
        (D) OTHER INFORMATION:

(xi) SEQUENCE DESCRIPTION: SEQ ID NO: 3:

GAGCTCCCAC GCTGCTGTTC TTCCATTTCC AGCTTTTAAA GAGCACCCGC CCCTTCGAA60

CACCGAGGTC ATGGGCGAAC ACACCGGAGC GCAGACCGCG CCCCCCCGCA CACACCGC120

GCCTCCGCGC CCTTGCCCAG ACCGAGGCGG CCGACGCGCC TGCGTGCGCG CTAGGTAT180

ATAGGTCCCA GGAGGCAGCC ACTGGGCAGA ACTGGGCTAC GGGCGCCGCG GGCC ATG237
                                                                Met
                                                                1

GCG GGC GAG AAC CAC CAG TGG CAG GGC AGC ATC CTC TAC AAC ATG CTT285
        Ala Gly Glu Asn His Gln Trp Gln Gly Ser Ile Leu Tyr Asn Met Leu
                        5                  10                  15

ATG AGC GCG AAG CAA ACG CGC GCG GCT CCT GAG GCT CCA GAG ACG CGG333
        Met Ser Ala Lys Gln Thr Arg Ala Ala Pro Glu Ala Pro Glu Thr Arg
                        20                  25                  30

CTG GTG GAT CAG TGT TGG GGC TGT TCG TGC GGC GAT GAG CCC GGG GTG381
        Leu Val Asp Gln Cys Trp Gly Cys Ser Cys Gly Asp Glu Pro Gly Val
                        35                  40                  45

GGC AGA GAG GGG CTG CTG GGC GGG CGG AAC GTG GCG CTC CTG TAC CGC429
        Gly Arg Glu Gly Leu Leu Gly Gly Arg Asn Val Ala Leu Leu Tyr Arg
        50                  55                  60                  65
```

```
TGC TGC TTT TGC GGT AAA GAC CAC CCA CGG CAG GGC AGC ATC CTC TAC  477
Cys Cys Phe Cys Gly Lys Asp His Pro Arg Gln Gly Ser Ile Leu Tyr
                 70                  75                  80

AGC ATG CTG ACG AGC GCA AAG CAA ACG TAC GCG GCA CCG AAG GCG CCC  525
Ser Met Leu Thr Ser Ala Lys Gln Thr Tyr Ala Ala Pro Lys Ala Pro
                 85                  90                  95

GAG GCG ACG CTG GGT CCG TGC TGG GGC TGT TCG TGC GGC TCT GAT CCC  573
Glu Ala Thr Leu Gly Pro Cys Trp Gly Cys Ser Cys Gly Ser Asp Pro
                100                 105                 110

GGG GTG GGC AGA GCG GGG CTT CCG GGT GGG CGG CCC GTG GCA CTC CTG  621
Gly Val Gly Arg Ala Gly Leu Pro Gly Gly Arg Pro Val Ala Leu Leu
                115                 120                 125

TAC CGC TGC TGC TTT TGT GGT GAA GAC CAC CCG CGG CAG GGC AGC ATC  669
Tyr Arg Cys Cys Phe Cys Gly Glu Asp His Pro Arg Gln Gly Ser Ile
130                 135                 140                 145

CTC TAC AGC TTG CTC ACT AGC TCA AAG CAA ACG CAC GTG GCT CCG GCA  717
Leu Tyr Ser Leu Leu Thr Ser Ser Lys Gln Thr His Val Ala Pro Ala
                150                 155                 160

GCG CCC GAG GCA CGG CCA GGG GGC GCG TGG TGG GAC CGC TCC TAC TTC  765
Ala Pro Glu Ala Arg Pro Gly Gly Ala Trp Trp Asp Arg Ser Tyr Phe
                165                 170                 175

GCG CAG AGG CCA GGG GGT AAA GAG GCG CTA CCA GGC GGG CGG GCC ACG  813
Ala Gln Arg Pro Gly Gly Lys Glu Ala Leu Pro Gly Gly Arg Ala Thr
                180                 185                 190

GCG CTT CTG TAC CGC TGC TGC TTT TGC GGT GAA GAC CAC CCG CAG CAG  861
Ala Leu Leu Tyr Arg Cys Cys Phe Cys Gly Glu Asp His Pro Gln Gln
195                 200                 205

GGC AGC ACC CTC TAC TGC GTG CCC ACG AGC ACA AAT CAA GCG CAG GCG  909
Gly Ser Thr Leu Tyr Cys Val Pro Thr Ser Thr Asn Gln Ala Gln Ala
210                 215                 220                 225

GCT CCG GAG GAG CGG CCG AGG GCC CCC TGG TGG GAC ACC TCC TCT GGT  957
Ala Pro Glu Glu Arg Pro Arg Ala Pro Trp Trp Asp Thr Ser Ser Gly
                230                 235                 240

GCG CTG CGG CCG GTG GCG CTC AAG AGT CCA CAG GTG GTC TGC GAG GC  1005
Ala Leu Arg Pro Val Ala Leu Lys Ser Pro Gln Val Val Cys Glu Ala
                245                 250                 255

GCC TCA GCG GGC CTG TTG AAG ACG CTG CGC TTC GTC AAG TAC TTG CC  1053
Ala Ser Ala Gly Leu Leu Lys Thr Leu Arg Phe Val Lys Tyr Leu Pro
                260                 265                 270

TGC TTC CAG GTG CTG CCC CTG GAC CAG CAG CTG GTG CTG GTG CGC AA  1101
Cys Phe Gln Val Leu Pro Leu Asp Gln Gln Leu Val Leu Val Arg Asn
                275                 280                 285

TGC TGG GCG TCC CTG CTC ATG CTT GAG CTG GCC CAG GAC CGC TTG CA  1149
Cys Trp Ala Ser Leu Leu Met Leu Glu Leu Ala Gln Asp Arg Leu Gln
290                 295                 300                 305

TTC GAG ACT GTG GAA GTC TCG GAG CCC AGC ATG CTG CAG AAG ATC CT  1197
Phe Glu Thr Val Glu Val Ser Glu Pro Ser Met Leu Gln Lys Ile Leu
                310                 315                 320

ACC ACC AGG CGG CGG GAG ACC GGG GGC AAC GAG CCA CTG CCC GTG CC  1245
Thr Thr Arg Arg Arg Glu Thr Gly Gly Asn Glu Pro Leu Pro Val Pro
                325                 330                 335

ACG CTG CAG CAC CAT TTG GCA CCG CCG GCG GAG GCC AGG AAG GTG CC  1293
Thr Leu Gln His His Leu Ala Pro Pro Ala Glu Ala Arg Lys Val Pro
                340                 345                 350

TCC GCC TCC CAG GTC CAA GCC ATC AAG TGC TTT CTT TCC AAA TGC TG  1341
Ser Ala Ser Gln Val Gln Ala Ile Lys Cys Phe Leu Ser Lys Cys Trp
355                 360                 365

AGT CTG AAC ATC AGT ACC AAG GAG TAC GCC TAC CTC AAG GGG ACC GT  1389
Ser Leu Asn Ile Ser Thr Lys Glu Tyr Ala Tyr Leu Lys Gly Thr Val
```

```
                370               375               380               385
CTC TTT AAC CCG GAC GTG CCG GGC CTG CAG TGC GTG AAG TAC ATT CA 1437
Leu Phe Asn Pro Asp Val Pro Gly Leu Gln Cys Val Lys Tyr Ile Gln
                    390               395               400

GGA CTC CAG TGG GGA ACT CAG CAA ATA CTC AGT GAA CAC ACC AGG AT 1485
Gly Leu Gln Trp Gly Thr Gln Gln Ile Leu Ser Glu His Thr Arg Met
            405               410               415

ACG CAC CAA GGG CCC CAT GAC AGA TTC ATC GAA CTT AAT AGT ACC CT 1533
Thr His Gln Gly Pro His Asp Arg Phe Ile Glu Leu Asn Ser Thr Leu
        420               425               430

TTC CTG CTG AGA TTC ATC AAT GCC AAT GTC ATT GCT GAA CTG TTC TT 1581
Phe Leu Leu Arg Phe Ile Asn Ala Asn Val Ile Ala Glu Leu Phe Phe
    435               440               445

AGG CCC ATC ATC GGC ACA GTC AGC ATG GAT GAT ATG ATG CTG GAA AR 1629
Arg Pro Ile Ile Gly Thr Val Ser Met Asp Asp Met Met Leu Glu Xaa
450               455               460               465

CTC TGT ACA AAG ATA TAAAGTCATG TGGGCCACAC AAGTGCAGTA GTGCAGTTC 1685
Leu Cys Thr Lys Ile
                470

CATGAGGGAA GAATAAAGAG CTGTGGGCAA AGAGTGTAA AATATTTTAA AATAAAC 1745

CTTAATATTT TTACATGCAG AGTATTTTGA TCTTCAATTA AAGAAATAAT TTTATTC 1805

GCACAGTCAC AAATTTCTCT GTTCCATAGT TAAAGAAGAC ATTTGCCAAC AGGTAGC 1865

GCTCTGTACA TCTTTTAAAA AAAAAATCGC AGGGTACTAG TATAATAAGC TATTTTC 1925

AGCGCAGCAA TTTCATGGAA CCTGCTCAAA TCAAATTTGT ACATATTGTT ATAATAA 1985

TTAAGGTCTT AACTATTAAC TTGATTGAAA AAAGCTT                    2022

(2) INFORMATION FOR SEQ ID NO: 4:

(i) SEQUENCE CHARACTERISTICS:
        (A) LENGTH: 470 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 4:

Met Ala Gly Glu Asn His Gln Trp Gln Gly Ser Ile Leu Tyr Asn Met
    1               5                   10                  15

Leu Met Ser Ala Lys Gln Thr Arg Ala Ala Pro Glu Ala Pro Glu Thr
                20                  25                  30

Arg Leu Val Asp Gln Cys Trp Gly Cys Ser Cys Gly Asp Glu Pro Gly
            35                  40                  45

Val Gly Arg Glu Gly Leu Leu Gly Gly Arg Asn Val Ala Leu Leu Tyr
        50                  55                  60

Arg Cys Cys Phe Cys Gly Lys Asp His Pro Arg Gln Gly Ser Ile Leu
    65                  70                  75                  80

Tyr Ser Met Leu Thr Ser Ala Lys Gln Thr Tyr Ala Ala Pro Lys Ala
                    85                  90                  95

Pro Glu Ala Thr Leu Gly Pro Cys Trp Gly Cys Ser Cys Gly Ser Asp
                100                 105                 110

Pro Gly Val Gly Arg Ala Gly Leu Pro Gly Gly Arg Pro Val Ala Leu
                115                 120                 125

Leu Tyr Arg Cys Cys Phe Cys Gly Glu Asp His Pro Arg Gln Gly Ser
        130                 135                 140
```

```
Ile Leu Tyr Ser Leu Leu Thr Ser Ser Lys Gln Thr His Val Ala Pro
145                 150                 155                 160

Ala Ala Pro Glu Ala Arg Pro Gly Gly Ala Trp Trp Asp Arg Ser Tyr
            165                 170                 175

Phe Ala Gln Arg Pro Gly Gly Lys Glu Ala Leu Pro Gly Gly Arg Ala
            180                 185                 190

Thr Ala Leu Leu Tyr Arg Cys Cys Phe Cys Gly Glu Asp His Pro Gln
            195                 200                 205

Gln Gly Ser Thr Leu Tyr Cys Val Pro Thr Ser Thr Asn Gln Ala Gln
            210                 215                 220

Ala Ala Pro Glu Glu Arg Pro Arg Ala Pro Trp Trp Asp Thr Ser Ser
225                 230                 235                 240

Gly Ala Leu Arg Pro Val Ala Leu Lys Ser Pro Gln Val Val Cys Glu
            245                 250                 255

Ala Ala Ser Ala Gly Leu Leu Lys Thr Leu Arg Phe Val Lys Tyr Leu
            260                 265                 270

Pro Cys Phe Gln Val Leu Pro Leu Asp Gln Gln Leu Val Leu Val Arg
            275                 280                 285

Asn Cys Trp Ala Ser Leu Leu Met Leu Glu Leu Ala Gln Asp Arg Leu
            290                 295                 300

Gln Phe Glu Thr Val Glu Val Ser Glu Pro Ser Met Leu Gln Lys Ile
305                 310                 315                 320

Leu Thr Thr Arg Arg Arg Glu Thr Gly Gly Asn Glu Pro Leu Pro Val
            325                 330                 335

Pro Thr Leu Gln His His Leu Ala Pro Pro Ala Glu Ala Arg Lys Val
            340                 345                 350

Pro Ser Ala Ser Gln Val Gln Ala Ile Lys Cys Phe Leu Ser Lys Cys
            355                 360                 365

Trp Ser Leu Asn Ile Ser Thr Lys Glu Tyr Ala Tyr Leu Lys Gly Thr
            370                 375                 380

Val Leu Phe Asn Pro Asp Val Pro Gly Leu Gln Cys Val Lys Tyr Ile
385                 390                 395                 400

Gln Gly Leu Gln Trp Gly Thr Gln Gln Ile Leu Ser Glu His Thr Arg
            405                 410                 415

Met Thr His Gln Gly Pro His Asp Arg Phe Ile Glu Leu Asn Ser Thr
            420                 425                 430

Leu Phe Leu Leu Arg Phe Ile Asn Ala Asn Val Ile Ala Glu Leu Phe
            435                 440                 445

Phe Arg Pro Ile Ile Gly Thr Val Ser Met Asp Asp Met Met Leu Glu
450                 455                 460

Xaa Leu Cys Thr Lys Ile
465             470

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: primer 3107

(xi) SEQUENCE DESCRIPTION: SEQ ID NO: 5:

GCTAGCAAAGGACTCTGTGGTG                                        22
```

DAX-1 PROTEIN, METHODS FOR PRODUCTION AND USE THEREOF

This application is based on a provisional application, U.S. Serial No. 60/001,713, filed Jul. 28, 1995.

This invention was made with support under Grant Numbers RO1 HD22563, P30 HD24064, P30 HD27823, and P50 HG00210 from the National Institute of Health, U.S. Department of Health and Human Resources and ACS PF-4074. Accordingly, the U.S. Government may have certain rights in the invention.

Throughout this application, various publications are referenced within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Presently, there are no commercially effective tests to provide a rapid diagnostic approach to individuals with adrenocortical disorders of metabolism and development such as the X-linked cytomegalic form of adrenal hypoplasia congenita (AHC) and hypogonadotropic hypogonadism (HH) due to mutations in DAX-1, a new member of the nuclear hormone receptor gene superfamily. Left untreated, the results of these disorders include failure to achieve pubertal growth, sexual maturity, and eventually death.

AHC is an inherited disorder of adrenal gland development. The disorder results in adrenal insufficiency early in infancy, with low serum concentration of glucocorticoids, mineralocorticoids and androgens, and failure to respond to ACTH stimulation. AHC is a rare disorder with an overall estimated frequency of 1:12,500 live births.

Clinical signs and symptoms of infants with adrenal hypoplasia include poor feeding, failure to gain weight, hyperpigmentation, vomiting, diarrhea, vascular collapse, and sudden death. Dehydration, hyponatremia, hyperkalemia, acidosis, and hypoglycemia are common biochemical findings characteristic of combined glucocorticoid and mineralocorticoid deficiency.

HH is commonly associated with the X-linked form of the disease, and is generally noted at the expected time of puberty. It is not clear if this form of HH is of pituitary or hypothalamic origin. HH often is noted in boys with X-linked AHC at the expected time of pubertal maturation. Furthermore, abnormalities of the genitourinary system appear to occur with increased frequency in boys with AHC, and these include: cryptorchidism, hypospadias, small external genitalia, ureteral reflux, and urethral stenosis.

It would be of significant value to society to be able to use information to develop tests to determine the genetic imprint of AHC or HH.

There is a need for laboratory tests that identify those having the propensity to develop AHC and HH. There is currently a need to develop (1) methods to identify patients who need treatment along with the appropriate type of treatment, (2) apparatus, and (3) systems to determine the characteristics of AHC and HH.

Members of the nuclear hormone receptor superfamily are ligand dependent transcription factors which modulate a large number of essential cellular processes. Members of the superfamily regulate a myriad of pathways in higher organisms ranging from development and morphogenesis to reproduction, behavior and homeostasis. The superfamily consists of receptors for steroid hormones (e.g. corticosteroids, estrogens, progestins, and androgens), steroid derivatives (dihydroxy vitamin D3) and non-steroids (thyroid hormone and retinoids). In addition, there are members of this superfamily for which a ligand has not yet been identified, the so-called "orphan receptors," or members which have lost ligand binding function (e.g., thyroid hormone receptor $\alpha 2$; TR$\alpha 2$).

Nuclear hormone receptors are localized within a cell and, in contrast to receptors for peptide hormones, are not cell-membrane associated. They mediate their function in the cell nucleus by directly influencing gene expression. The nuclear hormone receptors have high affinity for their ligand which is in the range of 10-9 to 10-11 M. It is believed that the lipophilic hormone passes through the cell membrane without the help of specialized membrane bound accessory proteins and binds to the receptor within the cell. Hormone binding has a drastic effect in transforming the receptor by changing its conformation and thereby altering its function and activity.

Hormones which act by way of nuclear hormone receptors affect numerous tissues and pathways. One such group of hormones is the corticosteroids, which can be divided into glucocorticoids (cortisol and corticosterone) and mineralocorticoids (aldosterone). They are synthesized in the adrenal cortex using cholesterol as a precursor. Also synthesized in the adrenal cortex are androgens, which affect growth, development of skeletal muscle and behavior.

SUMMARY OF THE INVENTION

The invention provides DAX-1 protein molecules. DAX-1 protein is a novel member of the nuclear hormone receptor superfamily and may bind a retinoic acid or other response element. DAX-1 is expressed in steroidogenic cells in mammals including the adrenal gland, ovaries, testes, hypothalamus and pituitary gland.

In one embodiment, the DAX-1 protein has the amino acid sequence beginning with methionine at position 1 and ending with isoleucine at position 470 as shown in FIG. 12.

Additionally, a DAX-1 protein molecule expressed by species other than the human species is encompassed within this invention. It will share substantial homology with the DAX-1 protein having the amino acid sequence beginning with methionine at position 1 and ending with isoleucine at position 470 as shown in FIG. 12. The data herein support the existence of the DAX-1 protein expressed by various species, e.g., from mammals to yeast (FIG. 10). A homologous sequence has been found also in C. elegans.

The invention also provides nucleic acid molecules encoding the protein of the invention (FIG. 12). For example, in one embodiment the nucleic acid molecule is a DNA molecule. The genomic DNA molecule includes both the intron and exons of the sequence which encodes DAX-1. Alternatively, the nucleic acid molecule is a cDNA molecule as shown in FIG. 12.

The proteins and nucleic acid molecules of the present invention are weapons that can be used as part of an arsenal of weapons against adrenocortical disorders of metabolism and development.

The invention also provides methods of gene therapy which utilize DAX-1 nucleic acid moleules. In one embodiment, a gene encoding a DAX-1 protein is transferred into steroidogenic cells. As a first step in this method, a vector comprising DNA encoding a DAX-1 protein is introduced into a producer cell which results in the integration of the vector into the cell. Producer cells into which the vector is integrated are then selected. As a final step, the producer cell is grafted proximate to the steroidogenic cells so that the steroidogenic cells are infected with the vector produced by the producer cell and the gene encoding DAX-1 is transferred to the steroidogenic cells. In a further embodiment, the vector used in the above method comprises a portion of the promoter region of the DAX-1 DNA sequence and a transgene. In a still further embodiment, the transgene is a therapeutic transgene.

The invention further provides a method for screening drugs which bind a DAX-1 protein. This method comprises, as a first step, transfecting a cell with (i) a vector capable of expressing at least the ligand binding domain of a DAX-1 gene linked with a DNA binding domain (DBD) sequence, and (ii) a construct capable of expressing a reporter gene and having a response element to which the DBD binds, wherein the construct is part of the vector or is separate therefrom. As a second step, the transfected cell is cultured under conditions permitting binding of the expressed DBD to the response element. Next, the transfected cell is contacted with a drug to be screened. The presence of a protein encoded by the reporter gene is then detected, the presence of the protein being indicative of the binding of the drug to DAX-1 protein.

BRIEF DESCRIPTION OF THE FIGURES

FIG. 1 shows the position of the DAX-1 gene in Xp21.

FIG. 2b shows the sequence of the DAX-1 DNA (SEQ ID NO.: 3) from the same two patients.

FIG. 4 shows the results of a prenatal diagnosis by FISH performed with the DAX-1 cosmid.

FIG. 7b shows the nucleotide sequence (SEQ ID NO.: 1) of a portion of exon 1 and the 5'-flanking region.

FIGS. 8b (SEQ ID NO.: 4, positions 256–297) and 8c (SEQ ID NO.: 4, positions 368–390) show amino acid alignment of the conserved regions II and III of the same group of the nuclear hormone receptors.

FIG. 9 shows polymorphisms and mutations in the DAX-1 gene.

FIG. 12 shows the nucleotide (SEQ ID NO.: 3) and predicted amino-acid sequence (SEQ ID NO.: 4) of DAX-1.

FIG. 20 shows alignment of the amino acids within regions II (SEQ ID NO.: 4, positions 256–297) and III (SEQ ID NO.: 4, positions 368–390).

FIG. 21 shows a comparison of the AF-2 or t4 transactivation domain of DAX-1 (SEQ ID NO.: 4, positions 452–470) to other nuclear hormone receptors.

FIG. 22a shows alignment of the 3.5 repeats within the amino-terminus of DAX-1 (SEQ ID NO.: 4).

FIG. 22b shows a comparison of the putative DAX-1 zinc finger to zinc fingers found in other double stranded DNA binding proteins.

FIG. 23 is a schematic of the DAX-1 protein illustrating the approximate location of various types of mutations causing AHC. Below the schematic is a Table containing all of the known mutations in the DAX-1 gene.

DETAILED DESCRIPTION OF THE INVENTION

Figure 2A:
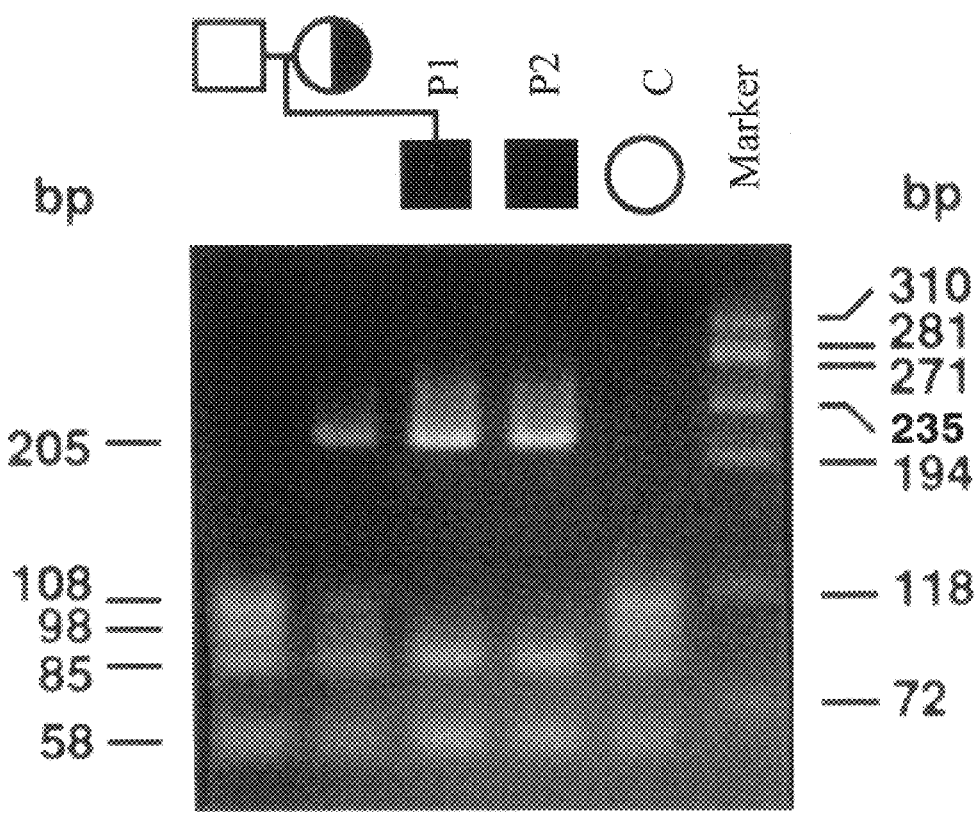
FIG. 2a shows the restriction pattern for two patients from apparently independent pedigrees following amplification of a portion of the DAX-1 cDNA, followed by digestion with RsaI.

All scientific and technical terms used in this application have meanings commonly used in the art unless otherwise specified. As used in this application, the following words or phrases have the meanings specified.

As used herein "therapeutic gene" means DNA encoding an amino acid sequence corresponding to a functional protein or peptide capable of exerting a therapeutic effect on diseased or damaged cells or having a regulatory effect on the expression of a function in diseased or damaged cells.

As used herein, "soluble" means unbound or circulating DAX-1 molecule such as a portion of DAX-1 fused genetically or chemically to a biologically or chemically active molecule which induces solubility, e.g., DAX-1 with an Ig tail.

As used herein "nucleic acid molecule" includes both DNA and RNA and, unless otherwise specified, includes both double-stranded, single-stranded nucleic acids, and nucleosides thereof. Also included are hybrids such as DNA-RNA hybrids, DNA-RNA-protein hybrids, RNA-protein hybrids and DNA-protein hybrids. Reference to a nucleic acid sequence can also include modified bases as long as the modification does not significantly interfere either with binding of a ligand such as a protein by the nucleic acid or Watson-Crick base pairing.

As used herein "enhancer element" is a DNA sequence that increases the activity of gene expression promoters for transcription. The enhancer element can be functional upstream, downstream, and in promoters without significant loss of activity.

As used herein "DAX-1" stands for dosage sensitive sex reversal locus, adrenal hypoplasia congenita on chromosome X, gene number 1.

As used herein "operatively linked" means to be connected to an expression control sequence in such a way so as to enable the expression of a protein encoded by the gene sequence.

As used herein "recombinant protein" means a protein molecule that is made using genetic engineering techniques.

As used herein "recombinant DNA" means a DNA molecule that is made using genetic engineering techniques.

As used herein "hybrid" means a nucleic acid molecule containing both DNA and RNA, DNA and protein, RNA and protein or DNA and RNA and protein.

As used herein "functional" means to be able to carry out normal activities, such as to express a gene.

As used herein "screening" means to select a target drug by testing samples of drugs for their effect on expression of a selected gene.

As used herein "a drug of interest" means a drug that is to be tested for its function in activating the expression of a reporter gene.

As used herein "compatible cell" means the cell is able to be transformed by a recombinant DNA using techniques in genetic engineering.

As used herein "reporter gene" means a gene whose expression can be readily detected in an assay.

As used herein "retinoic acid response element" means a nucleic acid sequence that can be bound by a retinoic acid receptor.

As used herein "transgene" means a gene whose expression is driven by the promoter element located upstream.

As used herein "DNA binding domain (DBD) sequence" means a nucleic acid sequence that encodes a protein domain that is capable of binding a response element on a nucleic acid molecule. Suitable examples include conventional DBDs such as LexA and Gal4. Also included are the DBDs of members of the nuclear hormone receptor superfamily, such as the glucocorticoid receptor and the retinoic acid receptor. Also included are non-conventional DBDs, such as the DBD of DAX-1 or SHP (W Seol et al. (1996) Science 272:1336–1338).

As used herein "response element" is a nucleotide sequence which effects an increase or decrease in gene expression when bound by a DNA-binding protein. A response element is responsive to a DBD if the response element effects an increase or decrease in gene expression in response to the binding of the corresponding DNA-binding protein to the response element.

As used herein, "diseases of adrenocortical metabolism and development" includes adrenal hypoplasia congenita (AHC), hypogonadotropic hypogonadism (HH), adrenocortical hyperplasia, adrenal aplasia, congenital adrenal hyperplasia, adrenal leukodystrophy, Addison's disease, adrenocortical adenoma, adrenocortical carcinoma and other disorders affecting or involving the adrenal cortex.

DAX-1 Protein Molecules

The invention provides an isolated protein designated DAX-1 which binds a retinoic acid response element.

The protein can be a human protein, a monkey protein, a mouse protein, a *C. elegans* protein or a yeast protein. However, DAX-1 isolated from any species is encompassed within this disclosure.

In one embodiment of the invention, the protein has the amino acid sequence beginning with methionine at position 1 and ending with isoleucine at position 470 as shown in FIG. 12 (SEQ ID NO: 3).

In another embodiment, the protein is a recombinant protein having an amino acid sequence substantially as shown in FIG. 12 (SEQ ID NO: 3).

In a further embodiment, the protein is a heterodimeric protein comprising DAX-1 and a nuclear hormone receptor. Suitable examples of nuclear hormone receptors include, but are not limited to, SF-1, thyroid hormone receptor, androgen receptor, estrogen receptor, progesterone receptor, glucocorticoid receptor, mineralocorticoid receptor, retinoic acid receptor, retinoid X receptor and COUP. The heterodimeric protein can comprise DAX-1 and SF1, or DAX-1 with any other nuclear hormone receptor.

DAX-1 protein molecules may be embodied in many forms. Embodiments of the DAX-1 protein include a purified DAX-1 protein and a functional, soluble DAX-1 protein. The purified DAX-1 protein molecule is substantially free of other proteins or molecules which impair the binding of DAX-1 to a retinoic acid or other response element.

One example of a functional soluble DAX-1 protein has the amino acid sequence beginning with methionine at position 1 and ending with isoleucine at position 470 as shown in FIG. 12 or a fragment thereof.

As used herein, the term "soluble" means unbound or circulating DAX-1 such as a portion of DAX-1 fused (genetically or chemically) to a biologically or chemically active molecule which induces solubility, e.g., DAX-1 with an Ig tail (DAX-l/Ig). In one embodiment, the functional, soluble DAX-1 protein or fragment thereof retains its ability to bind the retinoic acid or other response element.

In accordance with the practice of this invention, DAX-1 protein molecules of the invention may have amino acid changes (e.g., substitutions or deletions of one or more amino acid residues) within the molecule depending on the species expressing the DAX-1 protein (for example, the human DAX-1 protein shares about 65% identity and 75% similarity with the mouse DAX-1 protein) and the protein molecule will retain DAX-1 activity. Amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Nucleic Acid Molecules

The invention provides a nucleic acid molecule encoding a DAX-1 protein.

In one embodiment, the nucleic acid encodes a recombinant DAX-1 protein; in another embodiment, the nucleic acid molecule has a nucleotide sequence as shown in FIG. 12 (SEQ ID NO: 2).

The invention further provides a recombinant DNA molecule comprising a nucleotide sequence encoding a DAX-1 protein operatively linked to an expression control sequence.

The invention also provides nucleic acid molecules encoding the protein of the invention (FIG. 12). For example, in one embodiment the nucleic acid molecule is a DNA molecule. The genomic DNA molecule includes both the intron and exons of the sequence which encodes DAX-1. Alternatively, the nucleic acid molecule is a cDNA molecule as shown in FIG. 12. In another embodiment, the nucleic acid molecule is a ribonucleic acid (RNA). In another embodiment, the nucleic acid molecule is a hybrid DNA/RNA, DNA/protein, RNA/protein or DNA/RNA/protein molecule.

The invention also encompasses nucleic acid molecules that hybridize to the above-mentioned nucleic acid molecules of the invention and encode a protein having DAX-1 activity. The hybridization is under conventional hybridization conditions, preferably under stringent conditions.

The invention also encompasses DNA that encode anti-sense RNAs or specific ribozymes which allow the control of the expression of the nucleic acid molecules of the invention in desired host and target cells. The anti-sense RNAs and specific ribozymes are also encompassed by the invention. In another embodiment, the invention relates to primers which allow the specific amplification of nucleic acid molecules of the invention or of any specific parts thereof.

In another embodiment, the invention relates to probes that specifically hybridize to nucleic acid molecules of the invention or to any part thereof.

Vectors

The invention further provides an expression vector comprising a recombinant DNA molecule encoding a DAX-1 protein.

The invention further provides a vector having the nucleic acid molecule discussed hereinabove and a transgene. Preferably, the expression vector comprises a DNA molecule encoding a DAX-1 protein and a transgene. The vector can comprise a portion of the DAX-1 promoter. In one embodiment, the portion of the DAX-1 promoter is the SF-1 response element located upstream of the TATA box in the 5' flanking region of the DAX-1 gene.

In accordance with the practice of the invention the vector can further comprise a suitable enhancer element. Examples of suitable enhancer elements include but are not limited to a portion of the SF-1 promoter, a portion of the CMV promoter, a portion of the MMLV promoter, a portion of the SV40 promoter, a portion of the RSV promoter, or the SF-1 response element located upstream of the TATA box in the 5' flanking region of the DAX-1 gene.

In one embodiment, the transgene is a therapeutic gene. The therapeutic gene may encode a cytokine, a tumor suppressor, a growth factor, cytotoxin, or an antisense RNA molecule.

Alternatively, the therapeutic gene may be an oncogene. The therapeutic gene may serve to provide or augment expression of a deficient product to compensate for the deficiency, or the therapeutic gene may serve to inhibit the growth of or kill diseased cells associated with adrenocortical disorders of metabolism and development, or to produce cytokines or other cytotoxic agents which directly or indirectly inhibit the growth of or kill such diseased cells.

Examples of therapeutic genes which compensate for a deficiency include a gene encoding 21-hydroxylase, which can be used to compensate for a deficiency in 21-hydroxylase by increasing the expression of this enzyme in adrenal cells. Adrenal disorders, including 21-hydroxylase deficiency, are discussed in C J Migeon, P Donohoue (1994) in: M S Kappy et al., eds. Wilkins—the diagnosis and treatment of endocrine disorders in childhood and adolescence, 4th ed. Springfield: Thomas, 717–856.

Examples of therapeutic genes include suicide genes. These are gene sequences the expression of which produces a protein or agent that inhibits tumor cell growth or induces cell death (C. A. Mullen, Pharmac. Ther. Vol. 63, pp. 199–207, 1994). Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill diseased cells associated with adreno-cortical disorders of metabolism and development or produce cytokines or other cytotoxic agents which directly or indirectly inhibit the growth of or kill such diseased cells. Examples of suicide genes include, but are not limited to, genes which can induce programmed cell death such as the reaper gene.

Suitable enzymes include thymidine kinase (TK), xanthine-guanine phosphoribosyltransferase (GPT) gene from *E. Coli* or *E. Coli* cytosine deaminase (CD), or hypoxanthine phosphoribosyl transferase (HPRT). Treatment with a therapeutic transgene encoding an enzyme can render the transfected cells sensitive to subsequent drug treatment. In one embodiment, adrenal cells are transfected with the TK gene and thereby become sensitive to ganciclovir or acyclovir. In this embodiment, transfection of diseased adrenal cells with the TK gene is followed by treatment with ganciclovir or acyclovir to destroy the transfected adrenal cells and possibly also lyse adjacent diseased cells as well.

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include Pseudomonas exotoxin A and S; diphtheria toxin (DT); *E. coli* LT toxins, Shiga toxin, Shiga-like toxins (SLT-1, -2), ricin, abrin, supporin, and gelonin.

Suitable cytokines include interferons, GM-CSF interleukins, tumor necrosis factor (TNF) (Wong G, et al., Human GM-CSF: Molecular cloning of the complementary DNA and purification of the natural and recombinant proteins. *Science* 1985; 228:810; WO9323034 (1993); Horisberger M A, et al., Cloning and sequence analyses of cDNAs for interferon- and virus-induced human Mx proteins reveal that they contain putative guanine nucleotide-binding sites: functional study of the corresponding gene promoter. *Journal of Virology, March,* 1990 64(3):1171–81; Li Y P et al., Proinflammatory cytokines tumor necrosis factor-alpha and IL-6, but not IL-1, down-regulate the osteocalcin gene promoter. *Journal of Immunology,* Feb. 1, 1992 148(3) :788–94; Pizarro T T, et al. Induction of TNF alpha and TNF beta gene expression in rat cardiac transplants during allograft rejection. *Transplantation,* 1993 August, 56(2) :399–404; Breviario F, et al., Interleukin-1-inducible genes in endothelial cells. Cloning of a new gene related to C-reactive protein and serum amyloid P component. *Journal of Biological Chemistry,* Nov. 5, 1992 267(31):22190–7; Espinoza-Delgado I, et al., Regulation of IL-2 receptor subunit genes in human monocytes. Differential effects of IL-2 and IFN-gamma. *Journal of Immunology,* Nov 1, 1992 149(9):2961–8; Algate P A, et al., Regulation of the interleukin-3 (IL-3) receptor by IL-3 in the fetal liver-derived FL5.12 cell line. *Blood,* May 1, 1994 83(9) :2459–68; Cluitmans F H, et al., IL-4 down-regulates IL-2-, IL-3-, and GM-CSF-induced cytokine gene expression in peripheral blood monocytes. *Annals of Hematology,* 1994 June, 68(6):293–8; Lagoo, A S, et al., IL-2, IL-4, and IFN-gamma gene expression versus secretion in superantigen-activated T cells. Distinct requirement for costimulatory signals through adhesion molecules. *Journal of Immunology,* Feb. 15, 1994 152(4):1641–52; Martinez O M, et al., IL-2 and IL-5 gene expression in response to alloantigen in liver allograft recipients and in vitro. *Transplantation,* 1993 May, 55(5):1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. *Clinical and Experimental Immunology,* 1994 June, 96(3):437–43; Ulich T R, et al., Endotoxin-induced cytokine gene expression in vivo. III. IL-6 mRNA and serum protein expression and the in vivo hematologic effects of IL-6. *Journal of Immunology,* Apr. 1, 1991 146(7):2316–23; Mauviel A, et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. *Journal of Immunology,* Nov. 1, 1992 149(9):2969–76).

Growth factors include Transforming Growth Factor-α (TGFα) and β (TGFβ), cytokine colony stimulating factors (Shimane M, et al., Molecular cloning and characterization of G-CSF induced gene cDNA. *Biochemical and Biophysical Research Communications,* Feb. 28, 1994 199(1):26–32; Kay A B, et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. *Journal of Experimental Medicine,* Mar. 1, 1991 173(3):775–8; de Wit H, et al., Differential regulation of M-CSF and IL-6 gene expression in monocytic cells. *British Journal of Haematology,* 1994 February, 86(2):259–64; Sprecher E, et al., Detection of IL-1 beta, TNF-alpha, and IL-6 gene transcription by the polymerase chain reaction in keratinocytes, Langerhans cells and peritoneal exudate cells during infection with herpes simplex virus-1. *Archives of Virology,* 1992, 126(1–4):253–69).

Cytokines include but are not limited to interferons, interleukins and colony stimulating factors. Colony stimulating factors include but are not limited to granulocyte colony stimulating factor, or granulocyte macrophage colony stimulating factor.

The invention provides a host vector system comprising an expression vector encoding a DAX-1 protein, transfected into a compatible cell. Preferably, the compatible cell is a bacterial cell or a eucaryotic cell. An example of a compatible eucaryotic host cell is an adrenal cell.

In accordance with the practice of the invention, the vector can be a plasmid, cosmid or phage vector encoding the cDNA molecule discussed above. Additionally, the invention provides a host-vector system comprising the plasmid, cosmid or phage vector transfected into a compatible eucaryotic host cell. Examples of compatible eucaryotic host cells include a yeast cell, a plant cell, or an animal cell. The host-vector system is useful for the production of a DAX-1 protein.

Methods

The invention provides a method of producing a DAX-1 protein. The method comprises growing a host vector system so as to produce the DAX-1 protein and recovering the DAX-1 protein so produced.

By use of the above method, it is possible for the host-vector system to synthesize the DAX-1 proteins of the invention in culture in large quantities.

The invention further provides a method of producing a DAX-1 protein in vitro. This methods comprises transcribing a vector comprising a nucleic acid molecule encoding a DAX-1 protein in the presence of transcribable RNA, thereby creating mRNA. Additionally, the method requires translating the mRNA transcribed in the above step so as to provide DAX-1 protein. As a final step, the DAX-1 protein is recovered.

Gene Therapy

The invention further provides a method for inhibiting the proliferation of diseased cells associated with the presence of a DAX-1 protein. In this method, an adrenal or other steroidogenic cell is transfected with the recombinant DNA of the invention under conditions that the DAX-1 protein is expressed. The expression of the DAX-1 protein results in the inhibition of the proliferation of diseased cells. In one embodiment, the proliferation of adrenal cells is inhibited by increased expression of DAX-1 protein.

The invention further provides a method of transferring a therapeutic gene into steroidogenic cells of the hypothalamic-pituitary-adrenal/gonadal axis. This method comprises introducing a vector comprising a DAX-1 expression control sequence operatively linked to a therapeutic gene into a producer cell which results in the integration of the vector into the producer cell. In one embodiment, the vector is integrated into the genome of the producer cell. In another embodiment, such as with the use of adenoviruses, the vector is not integrated into the genome of the producer cell. As a second step, this method requires selecting a producer cell having the vector integrated into the cell. As a final step, the producer cell so selected is grafted proximate to the steroidogenic cells, so that the steroidogenic cells are infected with the vector produced by the producer cell and the therapeutic gene is transferred to the steroidogenic cells.

This invention also involves targeting a gene-of-interest to diseased cells associated with adrenocortical disorders of metabolism and development so that the protein encoded by the gene is expressed and directly or indirectly ameliorates the diseased state. Targeting strategies are known in the art and are reviewed in A. L. Joyner, ed., Gene Targeting: A Practical Approach, Oxford University Press: New York, 1993.

After infecting a susceptible cell, the transgene driven by a specific promoter in the vector expresses the protein encoded by the gene. The use of the highly specific DAX-1 gene vector allows selective expression of the specific genes in steroidogenic cells.

The present invention relates to a process for administering modified vectors into steroidogenic cells, for example, of the adrenal gland. More particularly, the invention relates to the use of vectors carrying functional therapeutic genes to produce molecules that are capable of directly or indirectly affecting cells in the adrenal gland to repair damage sustained by the cells from defects, disease or trauma.

Preferably, for treating defects, disease or damage of cells associated with adrenocortical disorders of metabolism and development, vectors of the invention include a therapeutic gene or transgenes. The genetically modified vectors are administered into the subject to treat defects, disease such as AHC or HH by introducing a therapeutic gene product or products into the subject that enhance the production of endogenous molecules that have ameliorative effects in vivo.

The basic tasks in the present method of the invention are isolating the gene of interest, selecting the proper vector vehicle to deliver the gene of interest to the body, administering the vector having the gene of interest into the body, and achieving appropriate expression of the gene of interest. The present invention provides packaging the cloned genes, i.e. the genes of interest, in such a way that they can be injected directly into the bloodstream or into relevant organs of patients who need them. The packaging will protect the foreign DNA from elimination by the immune system and direct it to appropriate tissues or cells. Examples of packaging include, but are not limited to, producer cells, liposomes and retroviruses. Packaging cells are described in P M Patel et al. (1993) in: G Gallagher et al., eds. Tumour Immunobiology: A Practical Approach, New York:Oxford, 296–303. Liposome packaging is described in M J Stewart et al., Hum. Gene Ther. (1992) 3:267–275.

Universal donor cells can be used to deliver the gene of interest; the donor cells may be heterologous, homologous or autologous. Immune responses to the donor material can be reduced by treatment with immunosuppression agents or by shielding the donor material with immunoisolation devices, such as the packaging discussed above.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

Clinical protocols for gene therapy are known in the art, E H Oldfield, Human Gene Therapy 4:39–69 (1993). Some of the human gene therapy protocols available from the Office of Recombinant DNA Activities of the National Institutes of Health in Bethesda Maryland include: 9506-110 Berchuck and Lyerly, H., A Phase I Study of Autologous Human Interleukin-2 (IL-2) Gene Modified Tumor Cells in Patients with Refractory Metastatic Ovarian Cancer; 9511-135 Alvarez, R. and Curiel, D., A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients; 9512-137 Hortobagyi, G., Lopez-Berstein, G., and Hung M., Phase I Study of E1A Gene Therapy for Patients with Metastatic Breast or Ovarian Cancer that Overexpresses Her-2/neu; and 9603-149 Holt, J., Ovarian Cancer Gene Therapy with BRCA-1.

Vectors for use in the gene therapy methods of the present invention include, but are not limited to, viral vectors such as adenoviruses, retroviral vectors, or adeno-associated viral (AAV) vectors.

The viral vector selected should meet the following criteria: 1) the vector must be able to infect the desired cells and thus viral vectors having an appropriate host range must be selected; 2) the transferred gene should be capable of persisting and being expressed in a cell for a suitable period of time; and 3) the vector should be safe to the host.

Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other viral vectors that may be used for gene transfer into cells for correction of disorders include retroviruses such as Moloney murine leukemia virus (MMLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. *PNAS USA*, 1977 74:1590; Berkner, K. L.: Development of adenovirus vectors for expression of heterologous genes. *Biotechniques*, 1988 6:616; Ghosh-Choudhury G, et al., Human adenovirus cloning vectors based on infectious bacterial plasmids. *Gene* 1986; 50:161; Hag-Ahmand Y, et al., Development of a helper-independent human adenovirus vector and its use in the transfer of the herpes simplex virus thymidine kinase gene. *J Virol* 1986; 57:257; Rosenfeld M, et al., Adenovirus-mediated transfer of a recombinant $\alpha_1$-antitrypsin gene to the lung epithelium in vivo. *Science* 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; Identification of the component necessary for adenovirus translational control and their utilization in cDNA expression vectors. *PNAS USA,* 1985 82:689).

AAV is a small human parvovirus with a single stranded DNA genome of approximately 5 kb. This virus can be propagated as an integrated provirus in several human cell types. AAV vectors have several advantages for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. *PNAS USA,* 1990 87:8950).

Another vector for mammalian gene transfer is the bovine papilloma virus-based vector (Sarver N, et al., Bovine papilloma virus DNA: A novel eukaryotic cloning vector. *Mol Cell Biol* 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. *Proc Natl Acad Sci USA* 1982; 79:4927; Smith et al. infectious vaccinia virus recombinants that express hepatitis B virus surface antigens. *Nature,* 1983 302:490.)

Retroviruses are packages designed to insert viral genes into host cells (Guild B, et al., Development of retrovirus vectors useful for expressing genes in cultured murine embryonic cells and hematopoietic cells in vivo. *J Virol* 1988; 62:795; Hock R A, et al., Retrovirus mediated transfer and expression of drug resistance genes in human hemopoietic progenitor cells. *Nature* 1986; 320:275).

The basic retrovirus consists of two identical strands of RNA packaged in a proviral protein. The core is surrounded by a protective coat called the envelope, which is derived from the membrane of the previous host but modified with glycoproteins contributed by the virus.

The methods described below to modify vectors and administering such modified vectors into the subject are merely for purposes of illustration and are typical of those that might be used. However, other procedures may also be employed, as is understood in the art.

Drug Screening

The invention further provides a method for screening drugs which bind a DAX-1 protein. This method comprises, as a first step, transfecting a cell with (i) a vector capable of expressing at least the ligand binding domain of a DAX-1 gene linked with a DNA binding domain (DBD) sequence, and (ii) a construct capable of expressing a reporter gene and having a response element to which the DBD binds. The construct may be part of the vector or separate therefrom. As a second step, the transfected cell is cultured under conditions permitting binding of the expressed DBD to the response element. Next, the transfected cell is contacted with a drug to be screened. The presence of a protein encoded by the reporter gene is then detected, the presence of the protein being indicative of the binding of the drug to DAX-1 protein.

The ligand binding domain (LBD) of the DAX-1 gene as used in the above method includes the E region of the DAX-1 gene, which corresponds to approximately positions 260 to 470 of the nucleotide sequence shown in FIG. 12. Also included are conservative variations of the E region, such as trimming the tail of the E region as well as other modifications of the nucleic acid sequence that do not prevent the encoded protein to bind ligand.

The LBD of the DAX-1 gene may be linked with a DBD either by fusion with a homologous or heterologous DBD or by inclusion of the DAX-1 DBD in a contiguous sequence. The DAX-1 sequence used in this method may be all or a portion of the nucleotide sequence shown in FIG. 12, a nucleotide sequence encoding the amino acid sequence shown in FIG. 12, or a nucleotide sequence encoding substantially the same amino acid sequence as that shown in FIG. 12.

The DBD sequence for use in the above method may be any DBD capable of binding to a response element. Examples of DBDs include, but are not limited to, the DBDs from the yeast transcription factors such as Gal4 or LexA, or from nuclear hormone receptors such as DAX-1, SF-1, glucocorticoid receptor or retinoic acid receptor.

The response element for use in the above method may be any response element, so long as it is responsive to the DBD.

Typically, ligand-bound nuclear receptor hormones act in dimeric form to activate expression of a target gene via binding to an appropriate response element. Some members of the nuclear receptor hormone superfamily, such as SHP, are believed to reduce gene expression, possibly by dimerizing with another nuclear receptor hormone and thereby preventing the other receptor from binding the appropriate response element. Thus, in one embodiment of the above method of screening drugs, binding of a drug to a DAX-1 protein will effect an increase in expression of the reporter gene. In another embodiment, binding of a drug to a DAX-1 protein would result in a decrease in expression of the reporter gene.

Suitable reporter genes for use in the above method include, but are not limited to, luciferase, β-galactosidase, chloramphenicol acetyl transferase (CAT) and secreted alkaline phosphatase (SeAP). SeAP is secreted directly into the culture medium, making the assay for reporter gene expression faster and simpler than would be the case for other reporter gene products.

Antibodies

The invention further provides antibodies that specifically bind to a DAX-1 protein. The antibodies may be polyclonal or monoclonal. The invention also encompasses antibody fragments which specifically recognize a DAX-1 protein. As used herein, an antibody fragment is defined as at least a portion of the variable region of the immunoglobulin molecule which binds to its target, i.e. the antigen binding region. Some of the constant region of the immunoglobulin may be included.

The monoclonal antibody of the invention can be produced using well-established hybridoma techniques first introduced by Kohler and Milstein [see, Kohler and Milstein, "Continuous Cultures Of Fused Cells Secreting Antibody Of Pre-Defined Specificity", *Nature,* 256:495–97 (1975). See, also, Brown et al., "Structural Characterization Of Human Melanoma-Associated Antigen p97 with Monoclonal Antibodies", *J. Immunol.,* 127 (2):539–46 (1981)]; Brown et al., "Protein Antigens Of Normal And Malignant Human Cells Identified By Immunoprecipitation With Monoclonal Antibodies", *J. Biol. Chem.,* 255:4980–83 (1980); Yeh et al., "Cell Surface Antigens Of Human Melanoma Identified By Monoclonal Antibody", *Proc. Natl. Acad. Sci. USA,* 76(6):297–31 (1979); and Yeh et al., "A Cell-Surface Antigen Which is Present In the Ganglioside Fraction And Shared By Human Melanomas", *Int. J. Cancer,* 29:269–75 (1982)].

These techniques involve the injection of an immunogen (e.g., cells or cellular extracts carrying the antigen or purified antigen) into an animal (e.g., a mouse) so as to elicit a desired immune response (i.e., antibodies) in that animal. After a sufficient time, antibody-producing lymphocytes are obtained from the animal either from the spleen, lymph nodes or peripheral blood. Preferably, the lymphocytes are obtained from the spleen. The splenic lymphocytes are then fused with a myeloma cell line, usually in the presence of a fusing agent such as polyethylene glycol (PEG). Any of a number of myeloma cell lines may be used as a fusion partner according to standard techniques; for example, the P3-NS1/1Ag4-1, P3-x63-Ag8.653 or Sp2/O Ag14 myeloma lines. These myeloma lines are available from the American Type Culture Collection ("ATCC") in Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting conditions to obtain isolated clones. The supernatants of the hybridomas are screened for the presence of antibody of that desired specificity, e.g., by immunoassay techniques using the antigen that had been used for immunization. Positive clones can then be subcloned under limiting dilution conditions and the monoclonal antibody produced can be isolated. Hybridomas produced according to these methods can be propagated in vitro or in vivo (in ascites fluid) using techniques known in the art [see, generally, Fink et al., supra at page 123, FIGS. 6–11]. Commonly used methods for purifying monoclonal antibodies include ammonium sulfate precipitation, ion exchange chromatography, and affinity chromatography [see, e.g., Zola et al., "Techniques For The Production And Characterization Of Monoclonal Hybridoma Antibodies", in *Monoclonal Hybridoma Antibodies: Techniques And Applications*, Hurell (ed.), pp. 51–52 (CRC Press 1982)].

Diagnostic Methods

The invention provides methods of diagnosing adrenocortical disorders such as AHC and HH, which arise from mutations of the DAX-1 gene. The diagnostic methods can be performed on patient samples containing DNA, including but not limited to DNA from white blood cells, DNA from whole blood or DNA from amniocytes.

In one method, a probe specific for the DAX-1 gene can be detectably labeled and allowed to hybridize in situ with the X chromosomes in the sample. Examples of detectable labels for use in this method include fluorescent labels. Examples of probes specific for DAX-1 include cosmid 8E10. An example of fluorescent in situ hybridization (FISH) for the detection of DAX-1 mutations in patient samples is presented in the examples which follow.

In another method, portions of the nucleic acid sequence shown in FIG. 12 (SEQ ID NO: 2) and in FIG. 7B (SEQ ID NO: 1) can be used in conventional nucleic acid amplification protocols, including PCR. Amplified strands can be sequenced according to standard techniques, including the use of commercially available kits (Pharmacia), and/or digested with restriction enzymes (e.g., Rsa I). Digested fragments may then be analyzed by, for example, dot hybridization and or gel electrophoresis, and compared to digested fragments prepared from normal subjects, with alterations in level of hybridization or fragment size being indicative of an abnormality in the DAX-1 gene.

Compositions

The invention provides a pharmaceutical composition comprising a nucleic acid molecule of the invention or an expression vector encoding a DAX-1 protein or encoding a fragment thereof and, optionally, a suitable carrier.

A suitable carrier includes any material which when combined with the nucleic acid or other molecule of the invention retains the molecule's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

The invention also provides a diagnostic composition comprising a nucleic acid molecule of the invention, a probe that specifically hybridizes to a nucleic acid molecule of the invention or to any part thereof, or an antibody or fragment thereof of the invention.

Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in *Molecular Cloning: A Laboratory Manual*, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with a nuclease results in hydrolysis of any single-stranded portion.

Ligations are performed in 10–50 $\mu$l volumes under the following standard conditions and temperatures using T4 DNA ligase. Ligation protocols are standard (D. Goeddel (ed.) Gene Expression Technology: Methods in Enzymology (1991)).

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in *Gene Expression Technology*, edited by D. V. Goeddel (1991).

Many methods for inserting functional DNA transgenes into cells are known in the art. For example, non-vector methods these commercially available restriction enzymes (See, e.g. New England Biolabs Product Catalog). In general, about 1 $\mu$g of plasmid or DNA sequences is cleaved by one unit of enzyme in about 20 $\mu$l of buffer solution. Typically, an excess of restriction enzyme is used to insure complete digestion of the DNA substrate.

Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65:499–560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in an appropriate buffer (e.g., 50 mM Tris (pH 7.6) 50 mM NaCl, 6 mM $MgCl_2$, 6 mM DTT and 5–10 μM dNTPs). The Klenow fragment fills in at 5' sticky ends but chews back protruding 3' single strands, even though the four dNTPs are present. If desired, selective repair can be performed by include nonviral physical transfection of DNA into cells; for example, microinjection (DePamphilis et al., *BioTechnique* 6:662–680 (1988)); liposomal mediated transfection (Felgner et al., *Proc. Natl. Acad. Sci. USA*, 84:7413–7417 (1987), Felgner and Holm, *Focus* 11:21–25 (1989) and Felgner et al., *Proc. West. Pharmacol. Soc.* 32: 115–121 (1989)) and other methods known in the art.

Administration of Modified Vectors into Subject

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. *Science* 1982; 215:166; Stavridis J C, et al., Construction of transferrin-coated liposomes for in vivo transport of exogenous DNA to bone marrow erythroblasts in rabbits. *Exp Cell Res* 1986; 164:568–572).

A vesicle can be constructed in such a way that its membrane will fuse with the outer membrane of a target cell. The vector of the invention in vesicles can home into the adrenal cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40% of an aqueous buffer containing macromolecules. The liposomes protect the DNA from nucleases and facilitate its introduction into target cells. Transfection can also occur through electroporation.

Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the subject, is relatively non-traumatic, allows multiple administrations simultaneously in several different sites or the same site using the same viral suspension. Multiple injections may consist of a mixture of therapeutic genes.

Survival of the Modified Vectors so Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulatory elements (Banerji et al., *Cell* 27:299 (1981); Corden et al., *Science* 209:1406 (1980); and Breathnach and Chambon, *Ann. Rev. Biochem.* 50:349 (1981)).

For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)).

Moloney murine leukemia virus (MMLV) and Rous sarcoma virus (RSV) LTRs contain promoter and enhancer sequences (Jolly et al., *Nucleic Acids Res.* 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., *Nature* 314:285 (1985); Rossi and de Crombrugghe, *Proc. Natl. Acad. Sci. USA* 84:5590–5594 (1987)).

The present invention provides methods for maintaining and increasing expression of therapeutic genes using a DAX-1 adrenal cell specific promoter.

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor, *Proc. Natl. Acad. Sci. USA* 70:2702 (1973)).

For example, in the present invention, CMV enhancer sequences can be used with the DAX-1 promoter to increase therapeutic gene expression. Therapeutic gene expression may also be increased for long term stable expression after injection using cytokines to modulate promoter activity.

The methods of the invention are exemplified by preferred embodiments in which modified vectors carrying a therapeutic gene are injected systemically or into the vicinity of the adrenal gland of a subject.

In a first embodiment a protein product can be expressed comprising growing the host vector system of the invention so as to produce the protein in the host and recovering the protein so produced. This method permits the expression of genes of interest in both unicellular and multicellular organisms. For example, in an in vitro assay, adrenal cells having the vector of the invention comprising a gene of interest (e.g., the ras gene) may be used in microtiter wells as an unlimited source for the ras gene product. A sample from a subject would be added to the wells to detect the presence of antibodies directed against the ras gene. This assay can aid in the quantitative and qualitative determination of the presence of ras antibodies in the sample for the clinical assessment of whether the subject's immune system is combatting the disease associated with elevated levels of ras.

In a second embodiment AHC or HH can be treated via gene therapy, i.e., the correction of a disease phenotype in vivo through the use of the nucleic acid molecules of the invention.

In accordance with the practice of this invention, the subject of the gene therapy may be a human, equine, porcine, bovine, murine, canine, feline, or avian subject. Other warm blooded animals are also included in this invention.

Figure 13:
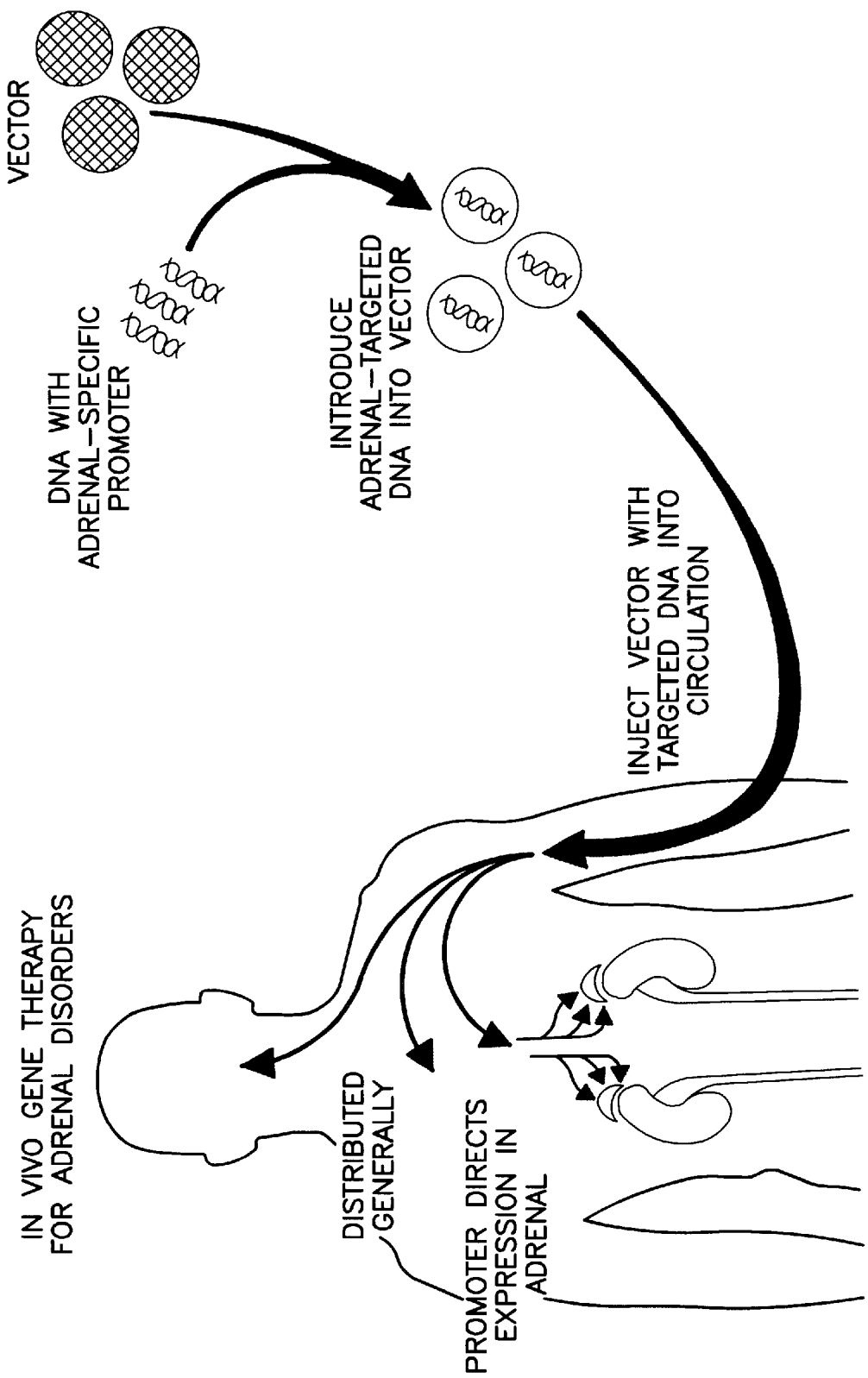
FIG. 13 shows a proposed strategy for gene therapy for disorders of adrenocortical development or metabolism.

FIG. 13 shows a strategy for gene therapy for disorders of adrenocortical development or metabolism. A promoter that would target expression to the adrenal cortex, such as the DAX-1 promoter, would be used with the coding sequence for the gene specific for the patient's disorder. The vector containing this construct would be introduced systemically, but expression would be targeted to the adrenal cortex. As indicated above, other administration means are possible.

The most effective mode of administration and dosage regimen for the molecules of the present invention depends upon the exact location of the diseased cells being treated, the s eve rity and course of the disease, the subject's age, health and response to treatment and the judgment of the treating physician. Accordingly, the dosages of the molecules should be titrated to the individual subject. The molecules may be delivered directly or indirectly via another cell, autologous cells are preferred, but homologous and heterologous cells are encompassed within the scope of the invention.

The interrelationship of dosages for animals of various sizes and species and humans based on mg/m$^2$ of surface area is described by Freireich, E. J., et al. Cancer Chemother., Rep. 50 (4): 219–244 (1966). Adjustments in the dosage regimen may be made to optimize the disease cell growth inhibiting and killing response, e.g., doses may be divided and administered on a daily basis or the dose reduced proportionally depending upon the situation (e.g., several divided doses may be administered daily or proportionally reduced depending on the specific therapeutic situation).

It would be clear that the dose of the molecules of the invention required to achieve cures may be further reduced with schedule optimization.

Advantages of the Invention

Molecular genetic screening of heritable disease syndromes is a rapidly evolving field of molecular medicine which will have a significant impact on human health in this and the next century. The identification of mutations associated with a vast number of heritable disease syndromes has considerable therapeutic value for affected individuals and allows more accurate genetic counseling for affected families.

The applicants have discovered the gene responsible for both X-linked adrenal hypoplasia congenita (AHC) and hypogonadotropic hypogonadism (HH). This gene is termed DAX-1 for dosage sensitive sex reversal locus, adrenal hypoplasia congenita at chromosome X, number 1. Carriers and individuals affected with these syndromes are found to display a wide range of genetic abnormalities within the DNA sequences at the DAX-1 locus.

Applicant's discovery allows for the screening and diagnosis of the disease syndromes associated with the DAX-1 gene.

Specifically, this invention allows for a quick and efficient analysis of the nucleic acid sequences which are affected in AHC and HH. In addition, the identification of the DAX-1 protein coding region allows for the generation of reagents such as monoclonal antibodies which have further diagnostic potential.

This invention is illustrated in the Experimental Details section which follows. This section is set forth to aid in an understanding of the invention but is not intended to, and should not be construed to, limit in any way the invention as set forth in the claims which follow.

EXPERIMENTAL DETAILS

Example 1

Diagnosis of X-linked AHC by Mutation Analysis of the DAX-1 Gene
Methods
Isolation of the Gene Responsible for AHC The DAX-1 cDNA was cloned by the method of cDNA amplification for identification of genomic expressed sequences as summarized below.

JK2 genomic DNA was used to screen the a human X chromosome cosmid library (LLOXNCO1"U", Lawrence Livermore National Laboratory, Livermore, Calif.) and identified two positive clones. The ends of these two cosmids were used as starting points to produce a complete cosmid contig between the markers YHX133R and JK2 (FIG. 1).

The ends of the cosmids were hybridized against the library described above, in order to walk in the telomeric and centromeric directions. The additional markers, QST59, 332F10R, A107E5R, YHX133L and K23-b2, were used to characterize the 15 cosmids in the contig.

To identify sequences in this region that were expressed in the human fetal adrenal gland, the cosmids in the contig were digested with EcoRI, Southern blotted and hybridized with a human fetal adrenal cDNA library in lambda gt11 (HL1118b Clontech, Palo Alto, CA) that had been amplified with primers to the vector ends and labeled as previously described.

Two bands (3.4-kb and 4.0-kb) were identified in four cosmids, three cosmids with both bands (designated in the LLOXNCO1 library: 8E10, about 38-kb; 38A2, about 30-kb; and 230H3, about 34-kb) and one cosmid with only the 3.4-kb band (17G12, about 35-kb).

Both fragments were subcloned into PTZ19R from one of the cosmids, cos 8E10, and subjected to automated sequencing (ABI 373A, Applied Biosystems, Foster City, Calif.). An open reading frame was identified in each of the two fragments after analysis with the Codon Preference, Pattern Recognition and Test Code programs (GCG, Madison, Wis.).

Two human adrenal gland cDNA libraries (HL1118b and HL1109n, Clontech, Palo Alto, Calif.) were screened with the 3.4-kb genomic fragment and eight positive clones were identified. After automated sequencing of the eight cDNA clones, the cDNA sequence was identical to the sequence of the two exons identified in the genomic fragments and accounted for the entire coding sequence (FIG. 1).

Two of the cDNA clones encompassed the 3' end of the transcript and the remaining six covered the majority of the transcript. None of the cDNAs included the 5' end of the transcript and that sequence was obtained from the genomic exon. Cosmid 8E10, which was used for FISH analysis (see below), contained both exons of DAX-1 and the approximately 3-kb intron (FIG. 1). Cosmid 8E10 mapped between A107E5R and YHX133L, and included the three EcoRI fragments containing the DAX-1 gene, ordered 3.4-kb, 1.4-kb and 4.0-kb, centromeric to telomeric, the direction of transcription. Exon 1 was contained in the 3.4-kb fragment and Exon 2 was contained in the 4.0-kb fragment.

FIG. 1 shows the position of the DAX-1 gene in Xp21. The figure is oriented with the telomere (Xp-ter) to the left and the centromere (Xp-cen) to the right. Yeast artificial chromosomes that have been previously mapped are shown as horizontal bars along the top, and markers in this region are shown at their approximate positions on the chromosome (hatched horizontal bar). The cosmid contig is shown below the chromosome with cosmid 8E10 indicated and vertical bars representing the DAX-1 exons. The region containing DAX-1 is shown at higher resolution below the cosmids, with its two exons and single intron, and the EcoRI restriction sites. The DAX-1 gene is transcribed in the direction from centromere to telomere (right to left).

Detection of Mutations Involving the DAX-1 Gene among Patients with AHC

All investigations involving human subjects were performed after informed consent, including the prenatal diagnosis, using a protocol and consent form approved by the Baylor College of Medicine institutional review board (IRB).

In all situations, the individuals and/or their families were told that the molecular genetic testing was of a research nature, and clinical decisions should not be based solely on that information.

DNA from white blood cells or transformed lymphoblastoid cell lines of patients with a diagnosis of AHC were analyzed by amplification using the PCR primers of Zanaria et al. (January 1994).

DNAs that were successfully amplified by all primer pairs were assumed to have a point mutation or small deletion or insertion, and the amplified products were digested with a series of restriction enzymes and subjected to automated sequencing. If amplification of a patient's DNA was unsuccessful with the DAX-1 primers, then the cell line from that patient was examined by FISH with cosmid 8E10 using standard methods.

Simultaneous DAPI banding was performed for chromosome band assignment and digital images were collected with a computer controlled Zeiss Axioplan epifluorescence microscope equipped with a cooled charge-coupled device (CCD) camera (Photometrics, Tucson, Ariz.). The separately recorded FITC and DAPI fluorescence gray scale images were pseudo-colored and merged using the GeneJoin software package (Yale University).

Images were obtained in registration from different fluores using a filter system (Chroma Technology, Inc., Brattleboro, Vt.) composed of a multi-band pass emission-beam splitter combination with individual exciters mounted on a computer-driven filter wheel close to the arc lamp.

Clinical Descriptions of Patients with AHC

RE is a 4 y.o. male who was born at term to a 37 y.o. G5 P4 Ab0 LC4 (three female full sibs and one male maternal half sib) mother after normal pregnancy and delivery, and weighed 8 lb. 10 oz. There were no perinatal complications and he was breast fed. He began to vomit during the first week of life and continued to vomit despite reflux precautions and formula changes.

He was admitted to the hospital at 3.5 weeks of age, where he was listless, weighed 8 lb., and had the following serum electrolytes: Na+ 104 mmol/L, K+ 8.2 mmol/L, Cl− 75 mmol/L and CO2 12 mmol/L. He was initially hydrated intravenously with normal saline containing glucose. Additional laboratory values included borderline low serum cortisol (170 mmol/L) and testosterone (2.67 mmol/L), elevated plasma ACTH (233 pmol/L) and renin activity (153 ng $L^{-1}s^{-1}$), and low urinary 17-hydroxysteroids (0.55 mmol/d) and aldosterone (1.39 mmol/d)

Family history was negative for endocrine disorders or neonatal deaths. He was started on i.v. hydrocortisone, and within one day his electrolytes improved and he tolerated oral feedings. He was diagnosed with AHC, was discharged on oral glucocorticoid and mineralocorticoid replacement, and continued to gain weight and feed well. At 4 years of age he is developmentally normal.

TP is a 6 y.o. male who was born at 42 weeks gestation to a G4 P3 Ab1 (SAB at 8 wks) LC2 (two female sibs) mother, who had a normal pregnancy, labor and delivery. His birth weight was 8 lb. 3 oz. and nursery discharge weight was 8 lb. 6 oz. At 3 weeks of age he was hospitalized because of failure to thrive (weight 8 lb. 3 oz.) and had a poor suck, fatigue, hyponatremia (Na+ 117 meq/L) and hyperkalemia (K+ 6.4 meq/L). He was started on glucocorticoid and mineralocorticoid replacement therapy and was treated with supplemental NaCl. In a later evaluation with an ACTH stimulation test (0.15 mg Cortrisin in 250 ml normal saline), his cortisol levels were unresponsive at 3 mmol/L.

His plasma ACTH rose from 249 pg/ml to 1490 pg/ml after withdrawal of his replacement steroids. He had an LRF stimulation test that showed maximum changes in his LH of 12.7 IU/L and FSH of 1.3 IU/L. The interpretation of these data was that he had an unresponsive adrenal gland, but a normal gonadotropic axis for his age. Therefore, at 17 months of age he was diagnosed with isolated AHC; his developmental evaluation was normal. Family history was positive for a subsequent male sibling with AHC, and for an adult maternal uncle who presented at 2½ years of age with weakness, dizziness and increased skin pigmentation, hypoglycemia (32 mg.dl, fasting), hyponatremia (124 meq/L) and hyperkalemia (6.8 meq/L).

He was unresponsive after ACTH stimulation (15 units every 12 hrs intramuscularly for 3 days) and he was diagnosed with Addison disease. The uncle had delayed puberty and was treated with testosterone at 20 years of age.

LC, 11 years of age, and NC, 8½ years of age, are full male siblings. LC first came to medical attention because of recurrent vomiting, failure to thrive in infancy and hyperpigmentation. Diagnostic testing suggested AHC, and he was placed on glucocorticoids and mineralocorticoids at approximately 6 months of age.

His younger brother, NC, developed adrenal crisis shortly after birth, and was started on glucocorticoid and mineralocorticoid replacement therapy at 2 weeks of age. Over the next several years, NC developed numerous episodes of adrenal crisis requiring hospitalization, whereas, LC has never had episodes of adrenal crisis.

NC had cryptorchidism, necessitating orchiopexy at 4 years of age and both boys have mild to moderate developmental disabilities. Family history is negative for other individuals affected with disorders of adrenal function. OM, the consultand in the fourth family, and VB are adult sisters, and FMB and DMB are the sons of VB. OM, a 36 y.o. female, was initially seen for prenatal genetic counseling because of advanced maternal age. The family history indicated numerous males dying in the neonatal period in a pattern consistent with X-linked inheritance. FMB, the first son of VB died at 3 weeks of age after becoming weak and lethargic. Post mortem examination of FMB was reported to be unremarkable, including normal genitalia and adrenals with cortical layers of the usual thickness.

DMB, was born to VB, who was then G2 P1 Ab0 LC1, after a normal term pregnancy and delivery. At two weeks of age, DMB became weak and lethargic, had slightly increased pigmentation of the nipples, oral mucosa and genitalia, and had a metabolic acidemia with Na+ 128 meq/L and K+ 9.0 meq/L. Laboratory studies at admission included low serum cortisol, low serum pregnanetriol, low serum aldosterone, elevated plasma ACTH, low urine ketosteroids with normal hydroxysteroids, abnormally high renin production and inadequate response to a 3 day ACTH stimulation test. He was diagnosed with AHC and was treated orally with glucocorticoids, mineralocorticoids and a sodium chloride solution.

On this regimen, his growth and development were normal. One day prior to his death, DMB had the onset of vomiting and diarrhea, was hospitalized, and had an acute hypertensive episode, following which he became unresponsive with pupils fixed and dilated, and had a seizure. Electrolytes at the time of the seizure included Na+ 125 meq/L and K+ 4.9 meq/L. He remained unresponsive, his EEG was isoelectric and he had gradual cardiorespiratory decompensation. At autopsy no adrenal tissue could be identified grossly nor upon microscopic examination of the perirenal fat and soft tissues. Death was thought to be due to severe cerebral edema.

High resolution chromosome analysis of OM and VB showed normal female karyotypes, 46,XX, with no evidence of an Xp21 deletion in either woman. Amniocentesis on OM indicated a male fetus with a normal, 46,XY, karyotype.
RESULTS Identical Single Base Pair Deletion Observed in Two Apparently Independent Pedigrees. When DNA specimens from patients RE and TP were amplified with the primer pair 2F and 2R, products of approximately the correct size were observed after agarose gel electrophoresis.

However, when the PCR products from the patients were digested with RsaI, an abnormal restriction pattern was identified in both patients, with apparent loss of a restriction site (FIG. 2). Amplification of a portion of the DAX-1 cDNA, followed by digestion with RsaI, showed loss of a restriction site in RE (P1) and TP (P2), resulting in an uncut 205-bp fragment instead of the normal 108-bp and 98-bp fragments (2a). The father of RE shows a restriction pattern identical to the control female (C), and the mother of RE is clearly a carrier, with the mutant and normal digestion products. Automated sequencing showed the deletion of a single base pair in both patients, nucleotide 1292 of the DAX-1 coding sequence, resulting in a frameshift and premature transcriptional termination (FIG. 2b).

The sequence indicates the precise size of the undigested RsaI fragments in the male probands: the normal 206-bp band would be cut into fragments of 108-bp and 98-bp, but the mutant 205-bp band could not be digested. The carrier mother of RE showed the 205-bp, 108-bp and 98-bp bands (FIG. 2). In order to rule out cross contamination or mix up of the RE and TP cell lines, they were characterized by two different polymorphic markers, DXS52 and the 3' end of the apoB gene. Different polymorphic patterns were observed with each cell line and with both markers, showing that the two cell lines were distinct.

Deletion of the DAX-1 Locus in Two Brothers with Isolated AHC

Figure 3A:
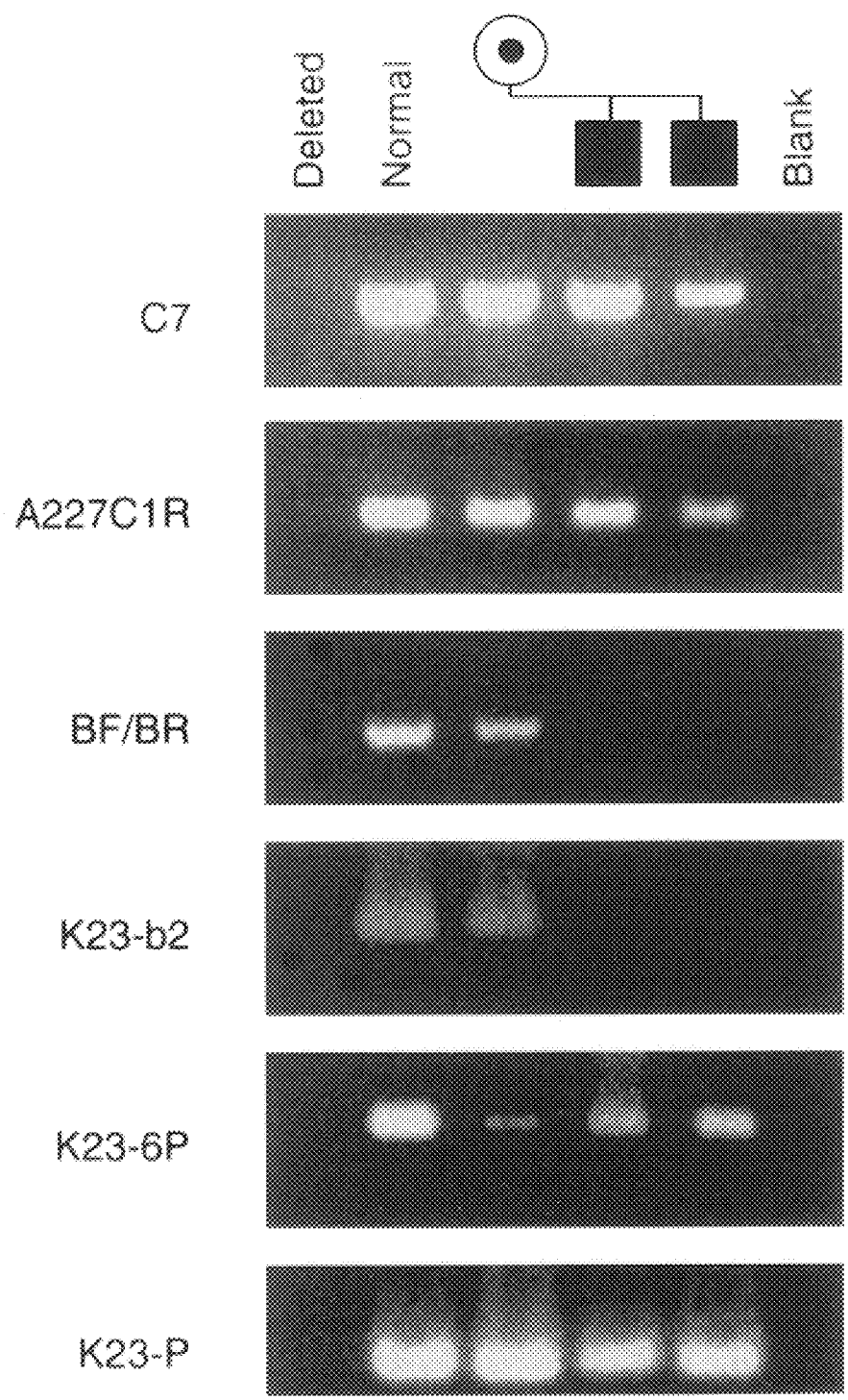
FIG. 3a shows deletion of the DAX-1 locus in two brothers with isolated AHC and reduced gene dosage in their mother.
Figure 3B:
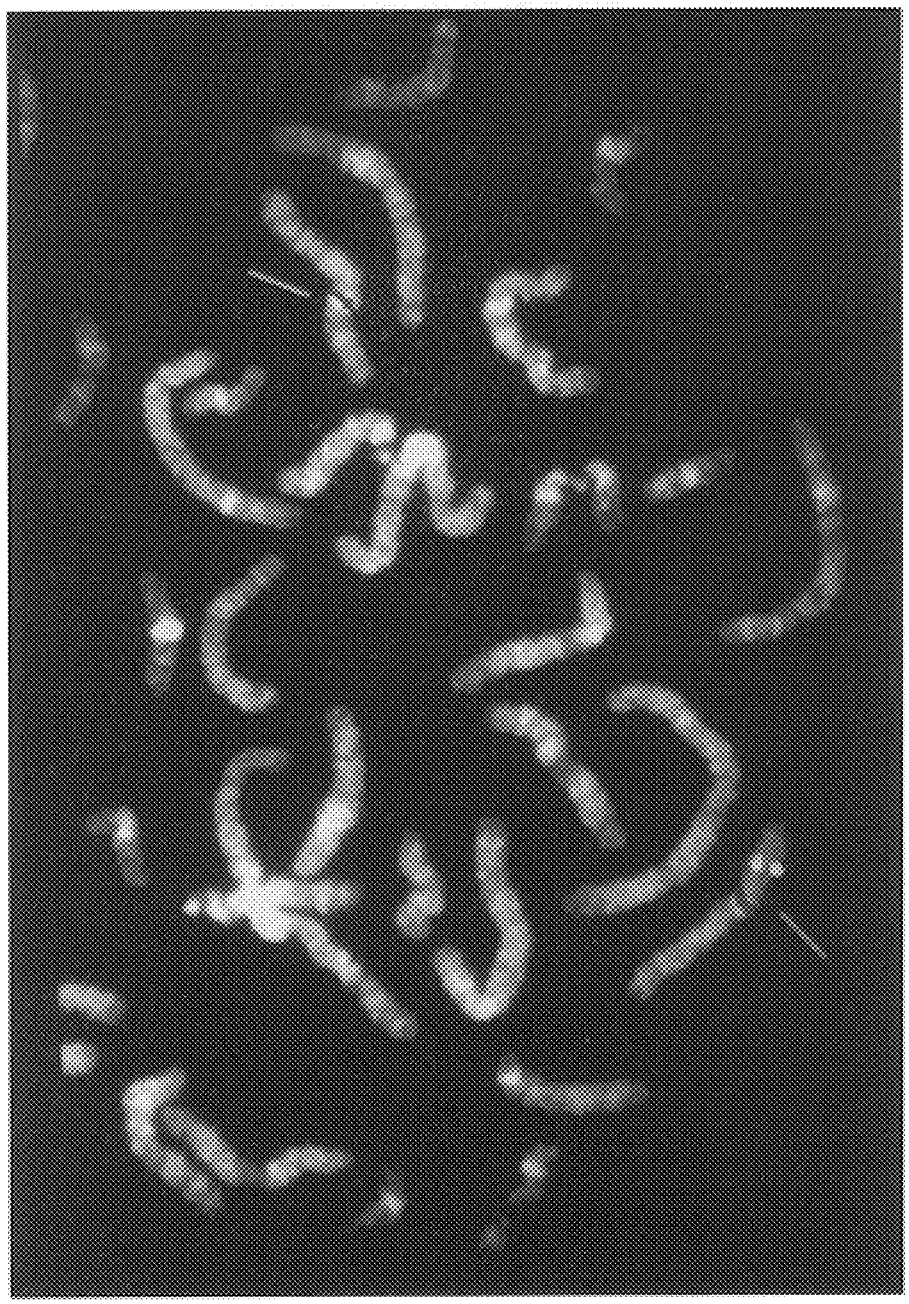
FIG. 3b shows confirmation of the mother's carrier status by fluorescence in situ hybridization (FISH) of the DAX-1 cosmid.

Amplification with the BF and BR primer pair for the DAX-1 gene showed deletion of this marker in both NC and LC, confirming that both brothers were affected with AHC (FIG. 3).

FIG. 3a shows previously mapped PCR markers, ordered from telomere (top) to centromere (bottom). These additional markers indicated that the telomeric breakpoint was between A227ClR, DAX-1 (BF-BR) and the centromeric breakpoint was between K23-b2 and K23-6P (FIG. 3). The affected boys were deleted for DAX-1 (BF BR) and K23-b2, and the amplifications of these markers in their mother appeared to be diminished compared to the normal control, suggesting a deletion in one of her X chromosomes. Analysis of PCR amplification products in the mother suggested the presence of reduced gene dosage (FIG. 3), consistent with carrier status, although the difference was not conclusive. The carrier status of the mother was confirmed by FISH with cosmid 8E10 (FIG. 3), which showed the presence of the centromeric control probe on both X chromosomes, but the presence of the DAX-1 cosmid, cosmid 8E10, signal on only one X chromosome (3b).

Prenatal Diagnosis for AHC by FISH with a Cosmid Containing the DAX-1 Gene

The pregnancy of OM presented the initial opportunity for the use of a cosmid containing the DAX-1 gene in prenatal diagnosis. No samples with intact DNA were available from her nephews and the nature of the mutation in this family was unknown.

Figure 4A:
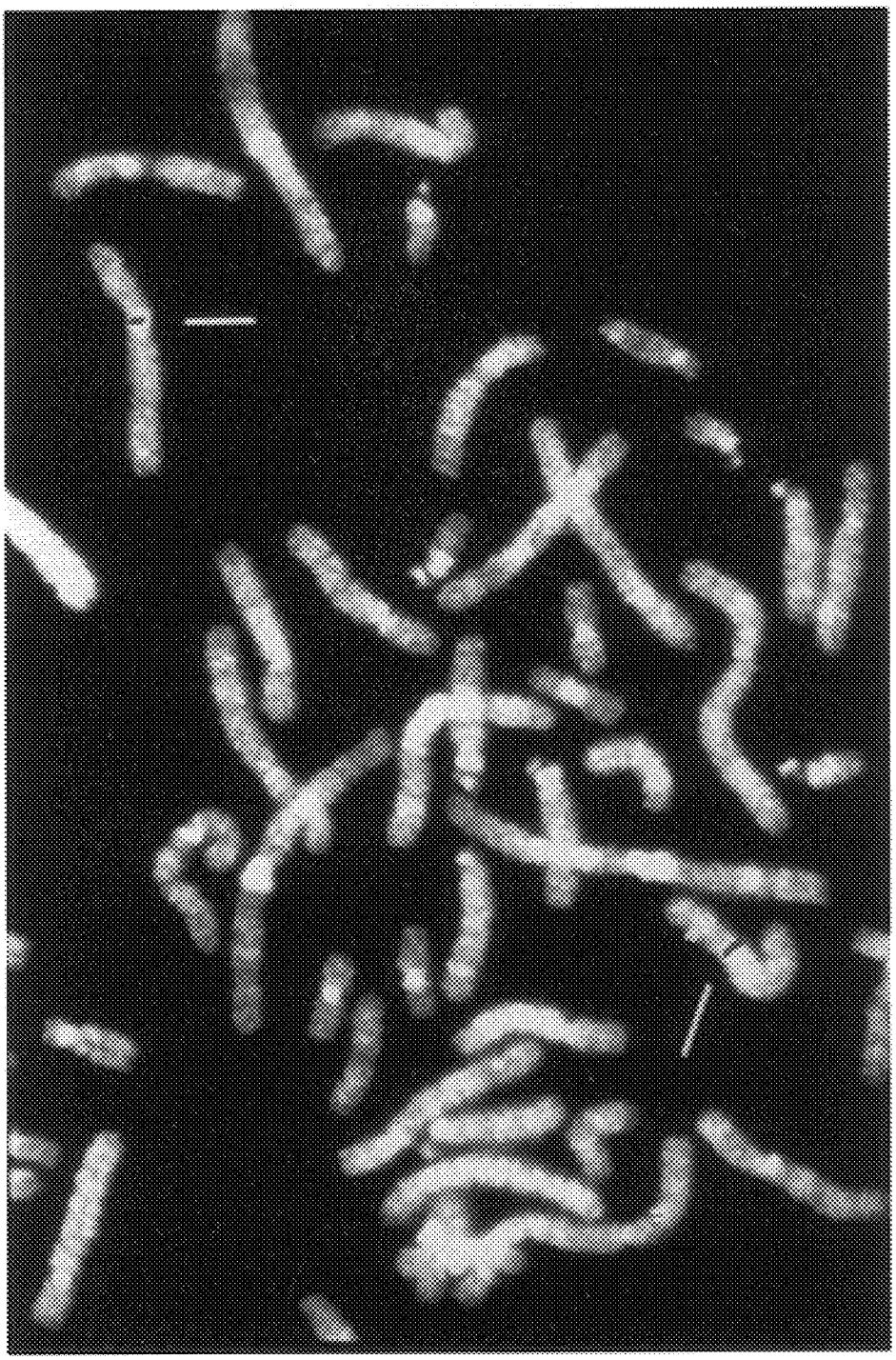
FIG. 4a shows deletion of DAX-1 in the obligate carrier sister of the consultant.

The mutation in this family was established by analysis of cells from VB, who was the sister of the consultand, OM, and an obligate heterozygote by pedigree analysis. FISH analysis of whole blood from VB with a cosmid containing the DAX-1 gene, cosmid 8E10, and an X centromere control probe, PDMX-1, showed deletion of the DAX-1 locus from one of her X chromosomes (FIG. 4a), indicating the loss of the DAX-1 gene as the cause of AHC in this family.

Figure 4B:
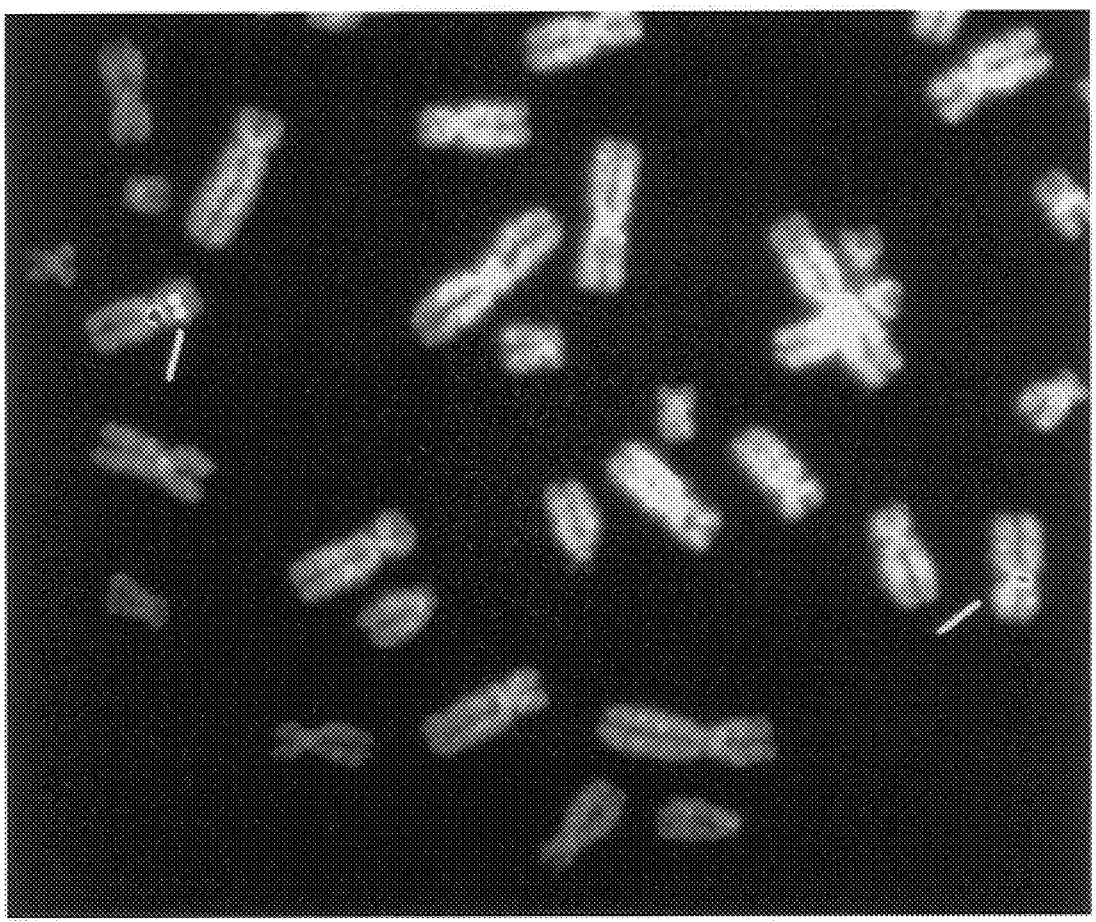
FIGS. 4b and 4c show normal hybridization in cells from the pregnant consultand (4b) and her male fetus (4c).
Figure 4C:
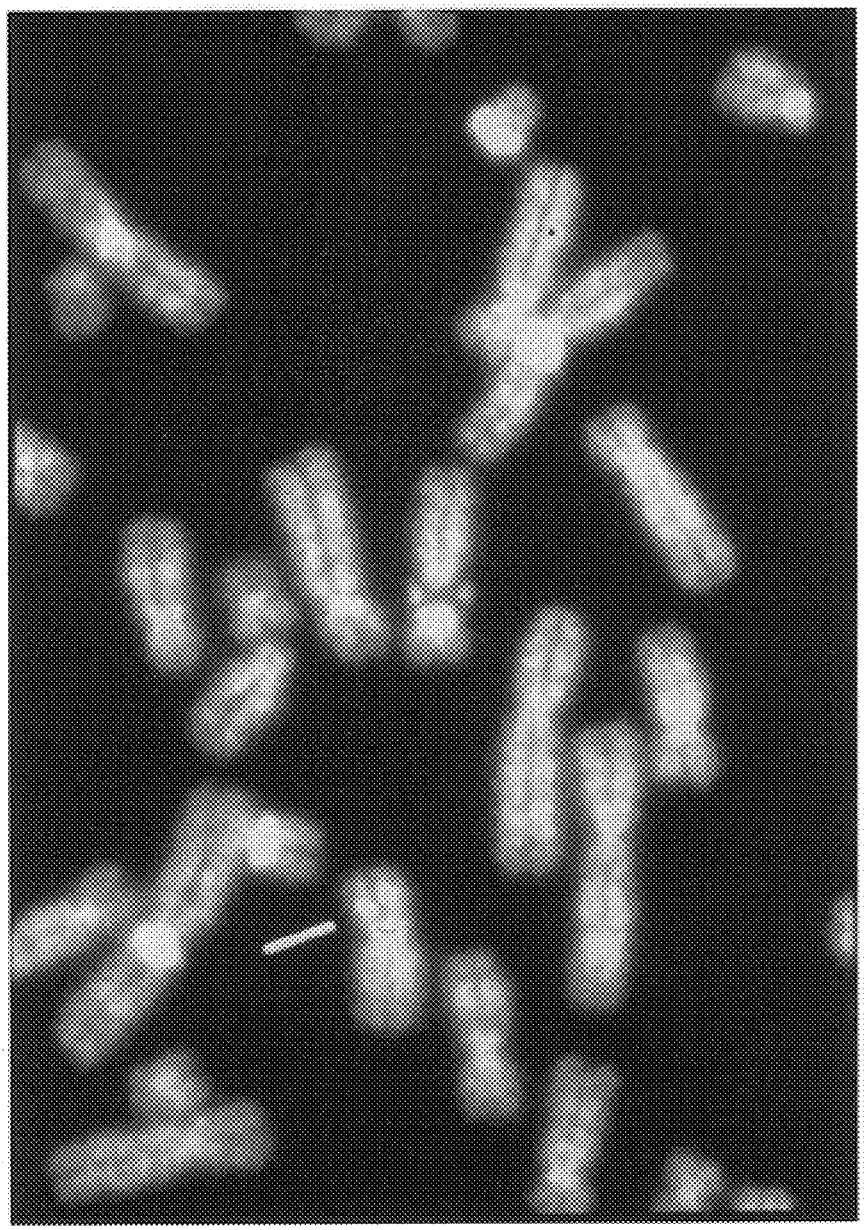

Blood was drawn from OM for FISH, and because of the gestational age of her fetus, amniocytes were analyzed at the same time for molecular cytogenetic determination of the DAX-1 genotype of her male fetus. Lymphocytes from the pregnant consultand (FIG. 4b) and amniocytes from her male fetus (FIG. 4c) showed normal hybridization with cosmid 8E10. These studies indicated that OM was not a carrier for the Xp21 microdeletion (FIG. 4), and, as would be expected, the male fetus had an intact DAX-1 gene (FIG. 4).

Subsequent FISH analysis with cos35, a cosmid containing a portion of the GK gene, showed that the deletion carried by VB extended in a centromeric direction to include the GK locus contiguous gene syndrome involving the centromeric loci in Xp21, GK and DMD. We observed a variety of mutations in our investigation of four families with AHC. The detection of their mutations required several different molecular genetic diagnostic techniques.

Two males with isolated AHC in apparently unrelated pedigrees exhibited single base pair deletions involving the identical nucleotide in each. Nucleotide 1292 of the coding sequence, representing the guanine in the second position of the serine codon (AGT) at residue 431 in the deduced amino acid sequence (S431), was deleted, resulting in a frameshift and premature termination of transcription.

We are unable to ascertain at this time whether these two pedigrees are distantly related and the mutations in both boys may have derived from the same genetic event, or whether these are identical mutations that occurred independently. The deletion of G1292 results in the loss of an RsaI restriction site, and affected males as well as carrier females can be readily identified.

A third family, containing two brothers diagnosed with AHC associated with mental retardation, showed a larger deletion, extending in a telomeric direction from a centromeric breakpoint between the AHC and GK genes. Larger deletions extending telomerically from presumed centromeric breakpoints within the AHC locus or between the AHC and GK loci have been observed in two boys with isolated AHC and mental retardation.

An affected male with a deletion of this type is readily diagnosed by PCR, but identification of a carrier female is more difficult. Evaluation of cells from a female relative requires analysis of total genomic DNA for dosage or isolation of the X chromosomes in a somatic cell hybrid. Both of these approaches are unsatisfactory for diagnostic testing: dosage analysis because it may be unreliable, and generation and evaluation of somatic cell hybrids because the process is time consuming and labor intensive. In contrast, FISH is an appropriate and effective technique for identification of submicroscopic deletions, because it is both efficient and reliable.

The fourth family afforded the first opportunity for prenatal diagnosis of AHC by FISH, using a cosmid containing the DAX-1 gene. The pregnant consultand gave a family history consistent with X-linked AHC, but DNA analysis had not been performed on any of the affected males, nor were any samples available from these males that contained intact DNA. FISH analysis of cells from the obligate carrier sister of the consultand indicated that the AHC in this family was due to deletion of the DAX-1 gene. FISH on cells from the consultand and her male fetus indicated that neither harbored the deletion. Therefore, the availability of molecular cytogenetic diagnosis of AHC reassured the mother that her fetus was unaffected, and prevented the possible termination of the male fetus.

Mutation detection within the DAX-1 gene is far superior to sex selection or measurement of maternal estriol levels for prenatal diagnosis of AHC.

Diagnosis of adrenal insufficiency, in order to initiate glucocorticoid and mineralocorticoid replacement therapy, is possible with standard endocrinologic testing, and does not require molecular genetic methods. However, appropriate management of the associated problems requires a specific diagnosis of the cause of the adrenal insufficiency.

Hypogonadotropic hypogonadism (HH) is associated with X-linked AHC, and treatment with testosterone, or possibly pulsatile GnRH, can enhance pubertal growth and development of secondary male sexual characteristics in affected patients. The DAX-1 cDNA and genomic reagents facilitate the specific diagnosis of AHC, and, therefore, predicts HH in the prepubertal period. A specific molecular genetic diagnosis also will allow more accurate genetic counseling of families with X-linked AHC.

The ligand for the DAX-1 nuclear receptor protein remains to be defined, but it is clear that mutations in this new X-linked orphan receptor have significant consequences for adrenal and gonadal development.

Example 2

DAX-1 shows sequence similarity with the nuclear hormone receptor superfamily, the highest similarities being observed with the RXR and orphan (COUP, ARP-1 and EAR-2) subfamilies. In addition, the DAX-1 protein binds DNA and is localized to the nucleus. Although the DAX-1 protein does not contain a recognized canonical zinc finger DNA binding domain, the protein contains cysteine residues that ar e s ituated appropriately for interaction with a zinc ion. The refore we would propose that the DAX-1 gene encodes a new, putative zinc finger protein that is involved in the transcriptional regulation of genes involved in the normal development of adrenal function and secondary sex characteristics.

Figure 5:
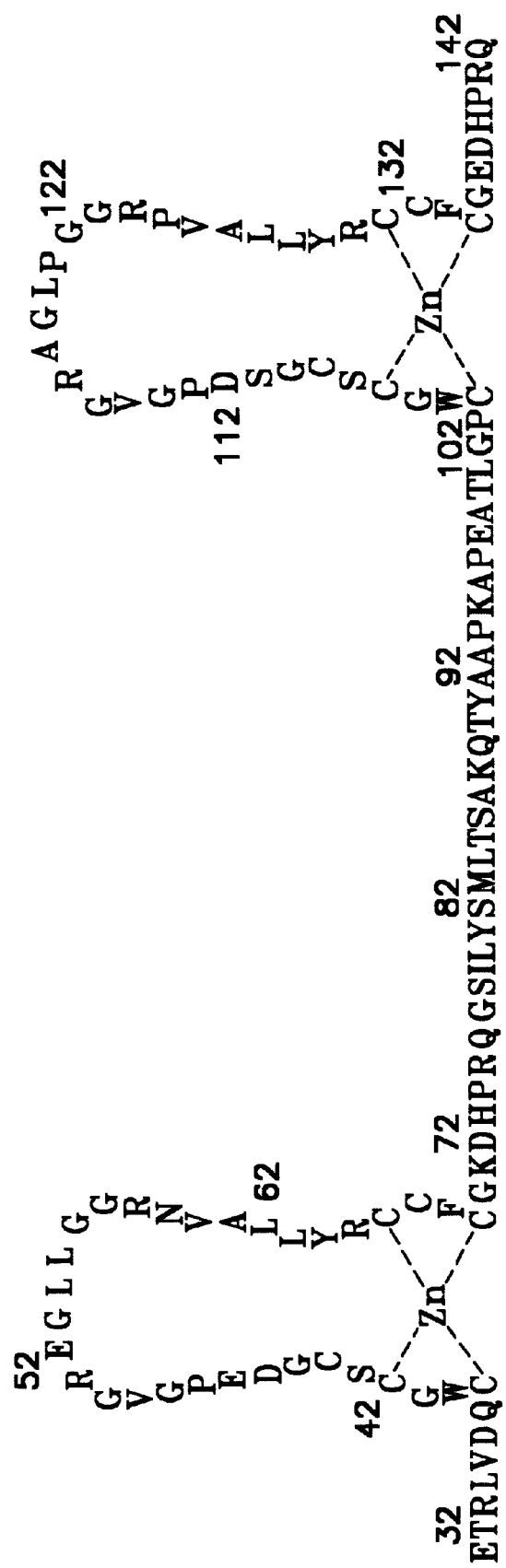
FIG. 5 shows the amino acid sequence (SEQ ID NO.: 4) in the putative zinc finger domain of the DAX-1 protein.

FIG. 5 shows the amino acid sequence in the putative zinc finger domain of the DAX-1 protein. The regions of DAX-1 that contain the putative zinc fingers are shown. We have drawn the interaction of the zinc ion with cysteines 41 and 107, but cannot rule out the alternative possibility of an interaction with cysteines 43 and 109.

Methods

DNA Sequencing and Sequence Analysis

An ABI 373 automated DNA sequencer was utilized with cycle sequencing and dye terminator chemistry for genomic sequencing. PCR amplified material was sequenced directly and subcloned material in pTZ19R was sequenced beginning with the universal and reverse primers, followed by walking primers. The sequence was repeated four to six times from both directions. The Gel programs were used for sequence assembly.

Nucleotide sequence analysis of the cloned genomic sequence utilized the BLAST E-Mail Server at National Center of Biotechnology Information. Computerized assessment of intron-exon boundaries employed the CodonPreference and Testcode programs, and evaluation of the nucleotide and deduced amino acid sequences relied on the GCG package.

For identification of mutations, manual sequencing of PCR amplified DNA fragment from the AHC patients was performed by the Sanger dideoxy chain termination sequencing method using the Sequenase Version 2.0 DNA Sequencing Kit (USB, Cleveland Ohio). Sequencing reactions were fractionated by electrophoresis on 8% urea-denatured polyacrylamide gels in 1×TBE buffer. The 35S-dATP labeled DNA samples were denatured at 75° C. for three min. prior to loading on the gel. After electrophoresis, the gel was soaked in 10% acetic acid, 12% methanol for 10 min. to remove the urea, then dried in a gel dryer (Model 583, BioRad, Richmond, Calif.) at 8° C. for 30 to 45 min., and exposed with direct contact to Kodak XAR-5 film for periods ranging from overnight to three days.

Single-strand conformational polymorphism (SSCP) analysis. SSCP analysis was performed according to the method of Orita et al. The entire DAX-1 gene, including the intron-exon boundaries, was divided into ten overlapping regions. The primer sequences and locations in the gene are listed at Table 1 and shown in FIG. 6. The 50 $\mu$l PCR reaction contained 200 ng genomic DNA, the appropriate primers (20 pM each), 20 nM dNTP, 0.1 ml a-32P-dCTF (3000 Ci/mMol and 10 mCi/ml; Amersham, Arlington Heights Ill.) and the PCR buffer contained 10mM Tris-HCl (pH8.8), 50 mM KCl, 1.5 mM MgCl2, and 0.1% gelatin. Two units of Taq DNA polymerase (Perkin Elmer) were added at 80° C. after a 5 min. hot start at 94° C.

The PCR amplification conditions were 0.5 min denaturation at 94° C., 0.5 min annealing at 55° C. and 1.0 min extension at 72° C. for 30 cycles. A 3 $\mu$l aliquot of the PCR reaction was mixed with 9 $\mu$l of the stop solution (95% formamide, 10 mM EDTA pH8.0, 0.01% xylene cyanole) and denatured for 5 min at 94° C. Then 4 $\mu$l aliquots of the mixtures were loaded on 0.5×MEDTM gel (AT Biochem, Malvern Pa.) (20×40×0.4 cm) with 90 mM Tris-borate pH8.3, 4 mM EDTA. Electrophoresis was performed at 700 volts for 12 hours. The gels were dried before being exposed to autoradiography film for 6 hours at −80° C. with an intensifying screen (VWR Sugar Land Tex.).

Figure 6:
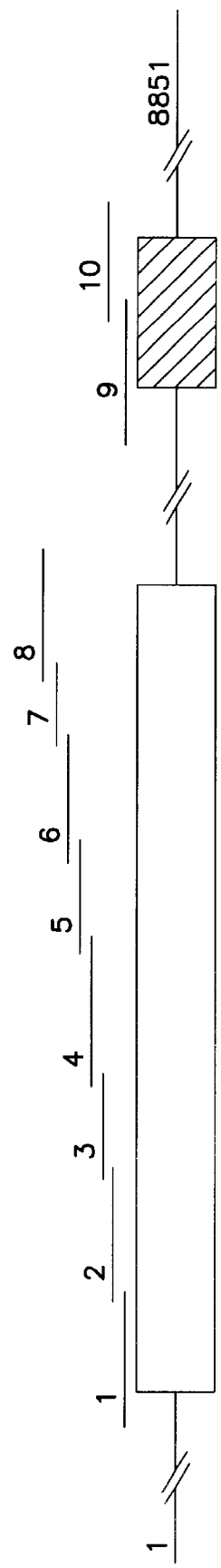
FIG. 6 shows the locations of the SSCP fragments in the DAX-1 gene.

FIG. 6 shows the locations of the SSCP fragments in the DAX-1 gene. The bold numbers indicate the orientation of the 8851 bp genomic sequence from nt 1 (on the left) to nt 8851 (on the right). The numbers for the 10 SSCP fragments are keyed to those in Table 1.

PCR amplification of DNA. The 258 bp fragment containing the tetra-nucleotide tandem repeat was amplified from the cosmid 8E10 13 clone which contain the entire DAX-1 gene, using primers 15 (5'-ACCAGCTGATACAGAATCAT-3') (complement of SEQ ID NO.: 1, positions 239–258) and 3140 (5'-CAATTCCAGGTCCTGGAGAA-3') (SEQ ID NO.: 1, positions 1–20). The PCR conditions for amplification of this repeats fragment were 1.0 min. denaturation at 94° C., 1.0 min. annealing at 57° C., and 1.0 min. extension at 72° C. for 32 cycles. The sequence (FIG. 6) from the second exon of the gene which detected the 2 bp insertion was amplified from genomic DNA of an AHC patient using primers 3107 (5'-GCTAGCAAAGGACTCTGTGGTG-3') (SEQ ID NO.: 5) and 2851 (5'-TCCATGCTGACTGTGCCGAT-3') (complement of SEQ ID NO.: 3, positions 1591–1610).

The 201 bp fragment (FIG. 6) from the first exon of the gene which showed a nucleotide substitution was amplified from the genomic DNA from two AHC patients and one carrier from two generations of the same family and also showed a 2 bp deletion in one AHC patient from a different family using primers 3557 (5'-GTCGCCTCGGGCGCCTTCGG-3') (complement of SEQ ID NO.: 3, positions 514–533) and 3603 (5'-CTGGTGGATCAGTGTTGGGGCT-3') (SEQ ID NO.: 3, positions 334–355).

The 225 bp fragment (FIG. 6) amplification product, from the first exon of the DNA from an AHC patient showed a nucleotide substitution polymorphism in many individuals including AHC patients and normal controls using primers 3544 (5'-GCTTGCTCACTAGCTCAAAGC-3') (SEQ ID NO.: 3, positions 677–697) and 3600 (5'-CTCTTGATTTGTGCTCGTGG-3') (complement of SEQ ID NO.: 3, positions 884–903). The PCR conditions for amplification of these three fragments were 1.0 min. denaturation at 94° C., 1.0 min. annealing at 55° C., and 1.0 min. extension at 72° C. for 32 cycles. Interspecies zoo blot. An interspecies zoo blot (cat. no. 7753-1 lot. no. 52556; Clontech, Palo Alto Calif.) was prehybridized in 5×SSPE, 10×Denhardts, 2% SDS, and 8–10 mg/ml sheared human placental DNA for 3 hours. The membrane was hybridized with a 1.6 kb SacI genomic fragment which contains the first exon of the AHC gene. The probe was labeled with a-32P dCTP using the random hexamer primer labeling method, and was preassociated with 8–10 mg/ml sheared human placental DNA in 5×SSPE, 10×Denhardts, and 2% SDS for 3 hours.

The hybridization was carried out at 65° C. for 18–20 hours. Following hybridization, the blot was washed in 2×SSC, and 0.05% SDS at room temperature for up to 20 min. A second wash in 2×SSC, and 0.1% SDS was performed for up to 15 min. at 65° C. 18.

Complete Sequencing of the DAX-1 Gene

The DAX-1 genomic region that was completely sequenced was contained within three EcoRI fragments (3.4, 1.4 and 4 Kb ordered from centromere to telomere). Two open reading frames were identified, and, when compared with the cDNA sequence, represented 1168 bp of coding sequence for first exon, a 3385 bp intron and a 245 bp coding sequence for the second exon. The complete sequence for the three EcoRI restriction fragments was 8851 bp in length and was deposited in GenBank (accession no. U31929).

FIG. 12 shows the nucleotide and predicted amino-acid sequence of DAX-1. The position of the intron and the sequence of the splice sites is shown above the sequence. Three potential polyadenylation signals were identified in the 3' noncoding sequence of the DAX-1 gene (underlined). The second of these signals (shown in bold) is used in the only polyadenylated cDNA we isolated. The arrow corresponds to the site of polyadenylation. The horizontal arrows correspond to the oligonucleotide primers used to analyse AHC patients.

Exon/intron organization of the gene. The first nucleotide of the presumptive initiation codon for the first exon was at position 1580 in the 3.4 kb EcoRI fragment, and the exon ended at position 2747. The rest of this fragment and the 1.4 kb EcoRI fragment contained intronic sequence. The remainder of the intron and second exon were located in the 4 kb EcoRI fragment. The coding region of the second exon consisted of a total of 245 base pairs starting at position 6133 with the third nucleotide of the stop codon at position 6377. The intron of the DAX-1 gene was 3385 bp in size and showed a highly conserved splice site at the exon-intron boundary with a GT at the donor site and an AG at the acceptor site (FIG. 7A).

Figure 7A:
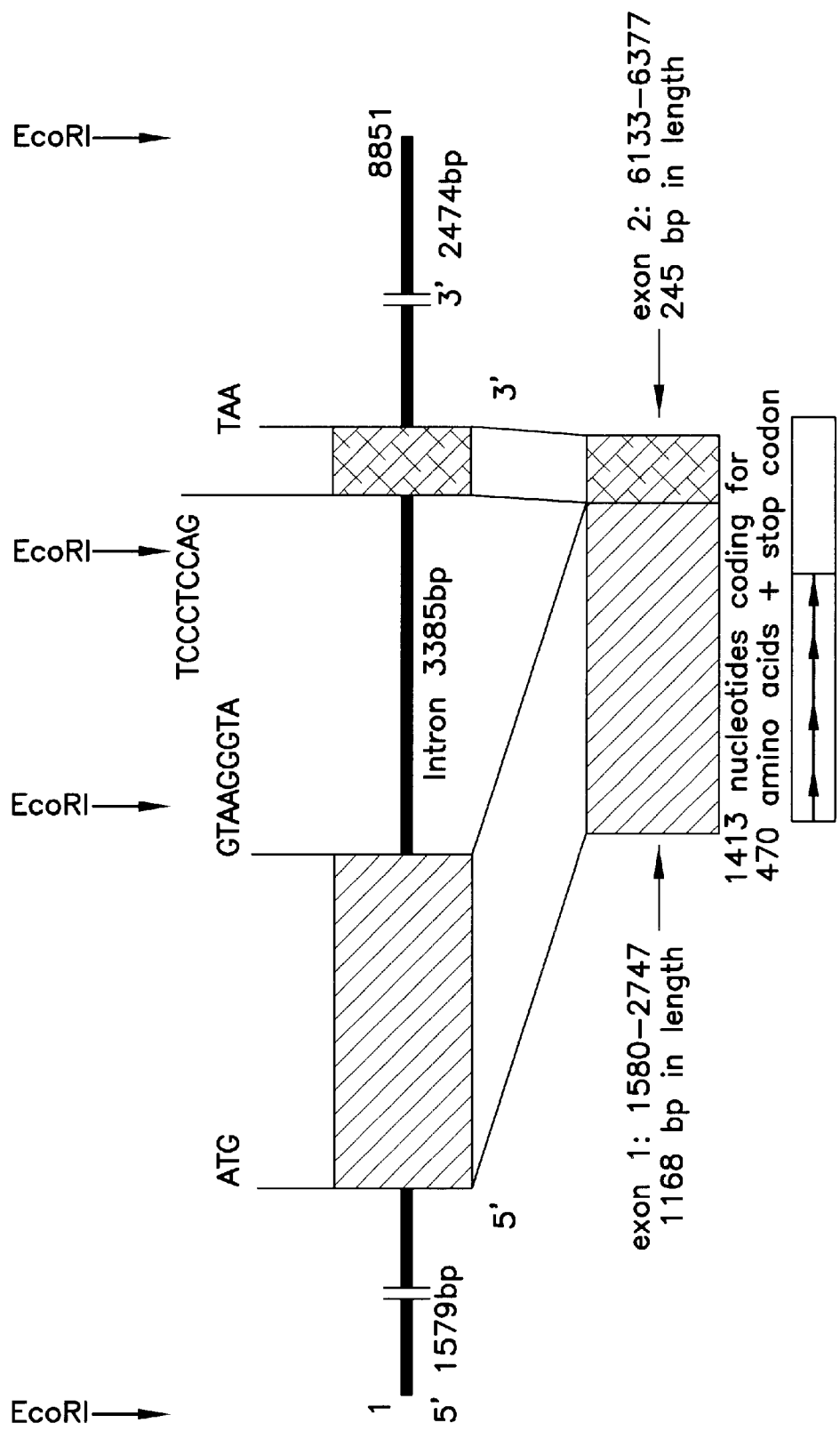
FIG. 7a shows the genomic organization of the DAX-1 gene.

FIG. 7a shows the genomic organization of the DAX-1 gene. The two exons of the DAX-1 gene are shown as boxed regions with numbers on the sides indicating the size of each exon. The 5' and $_3$' untranslated region and the intron are represented by the solid line and the numbers underneath the lines indicate the size of each region. The numbers at the beginning and the end of the solid line indicate the total size of genomic region which has been sequenced, 8851 bp. The conserved splice sites are indicated as bolded letters and a short portion of the intronic sequence is represented by the splice junction regions. The box at the bottom, with the three and the half repeats of 65–67 amino acids each, shows the putative DNA binding domain indicated by the arrows in the box, and the ligand binding domain indicated by the open box.

FIG. 7b shows the nucleotide sequence of a portion of exon 1 and the 5'-flanking region. The putative TATA box, GC boxes and the SF-1 response element are underlined and the GGAA tetra-nucleotide tandem repeat [(GGAA) 6GGAAA(GGAA)6GGAAA (GGAA)10] (SEQ ID NO.: 1, positions 88–185) is boxed. The numbering of the nucleotide sequence on the right is relative to the transcription start site.

Putative promoter and 3' untranslated region of DAX-1. The 1579 bp of sequence upstream of the transcription initiation site was examined for distinguishing promoter elements (FIG. 7B, position –1579 to –1; and SEQ ID NO.: 1, position 1 to 1579). A putative TATA box was identified at bases –58 to –53 upstream of first nucleotide of the initiation codon and a putative steroidogenic factor 1 (SF-1) response element (CCGAGGTCA) was present between bases –172 to –164, relative to the translation start site as shown in FIG. 7B (SEQ ID NO.: 1, position 1408–1416). The promoter region of the DAX-1 gene was found to be abundant in G+C content. Another prominent feature was the existence of several GC boxes, GGGCGG (CCGCCC), the recognition site of the Sp1 transcription factor. These GC elements are located at positions –188 to –183, –120 to –115 and +165 to +170 (FIG. 7B). Two AATAAA potential polyadenylation recognition sites were identified at positions 6427 and 6466. The second one was the one used as the polyadenylation site in the cDNA clone that we identified previously.

Figure 8A:
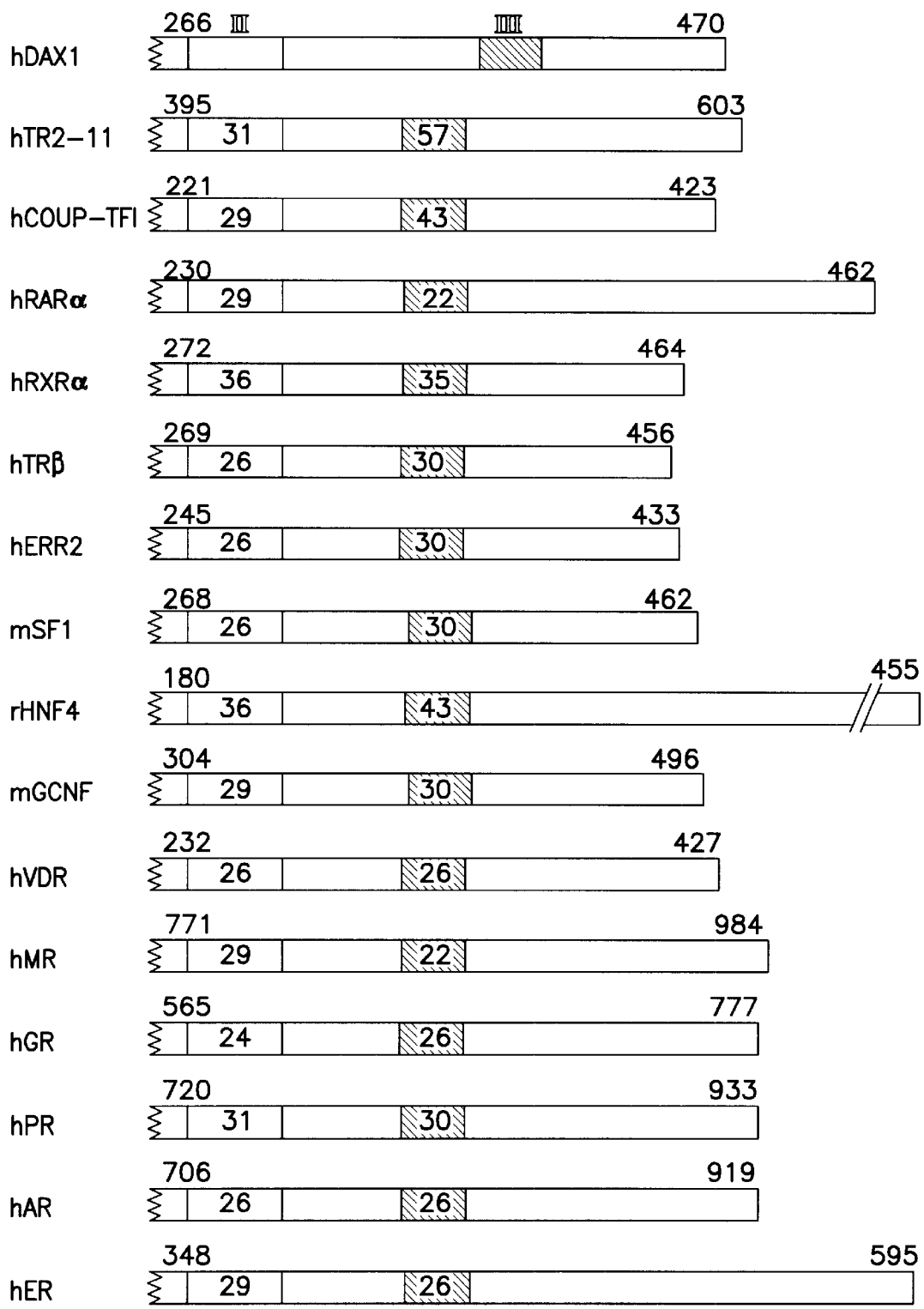
FIG. 8a shows alignment of the C-terminal ligand binding domain of several members of the nuclear hormone receptors, using DAX-1 as the basis for comparison.

FIG. 8a shows alignment of the C-terminal ligand binding domain of several members of the nuclear hormone receptors, using DAX-1 as the basis for comparison. The lower case prefixed letters refer to the species from which the gene was obtained: m, mouse; r, rat; and h, human. TR, thyroid hormone receptor; COUP-TF1, chicken ovalbumin upstream promoter transcription factor; RAR, retinoic acid receptor; RXR, retinoic X receptor; ERR, estrogen related receptor; SF-1, steroidogenesis factor-1; HNF, hepatocyte nuclear factor; GCNF, germ cell nuclear factor; VDR, vitamin D3 receptor; MR, mineralocorticoid receptor; GR, glucocoticoid receptor; PR, progesterone receptor; AR, androgen receptor; ER, estrogen receptor. The numbers on each side of the bars represent the beginning and end of the amino acid positions used in the comparison to DAX-1 for each member. The gray and hatched boxes represent conserved regions II and III in the nuclear hormone receptors, respectively. The numbers in the boxes indicate the percentage of amino acids in this region identical to the DAX-1 gene.

Comparison of DAX-1 Protein with the Other Members of the Nuclear Hormone Receptor Superfamily Comparison of DAX-1 deduced amino acid sequence with members of the nuclear hormone receptor superfamily showed a high degree of similarity with other sequences for regions II and III within the ligand binding domain (FIG. 8A). No obvious sequence similarity was found between the putative DAX-1 DNA binding domain and the DNA binding domain of any of these nuclear receptors. Detailed amino acid alignment of the conserved regions II and III of these receptors showed 24–36% identity and 43–60% similarity in region II and 22–57% identity and 23–61% similarity in region III 19 (FIGS. 8B and C).

FIGS. 8b and 8c show amino acid alignment of the conserved regions II and III of same group of the nuclear hormone receptors. Amino acids identical to DAX-1 are represented with a dash. Similar amino acids are bolded. The numbers on the right represent the positions of amino acid residues in the individual receptors. In region II the identity ranges from 24 to 36% and the similarity ranges from 43 to 60%, and in region III the identity ranges from 22 to 57% and similarity ranges from 23 to 61%.

Polymorphisms and Mutations in the DAX-1 Gene

Figure 9A:
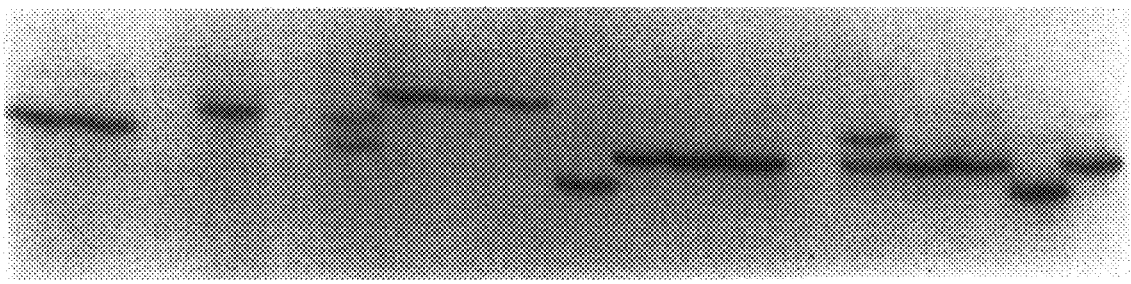
FIG. 9a shows nineteen DNA samples from different individuals.
Figure 9B:
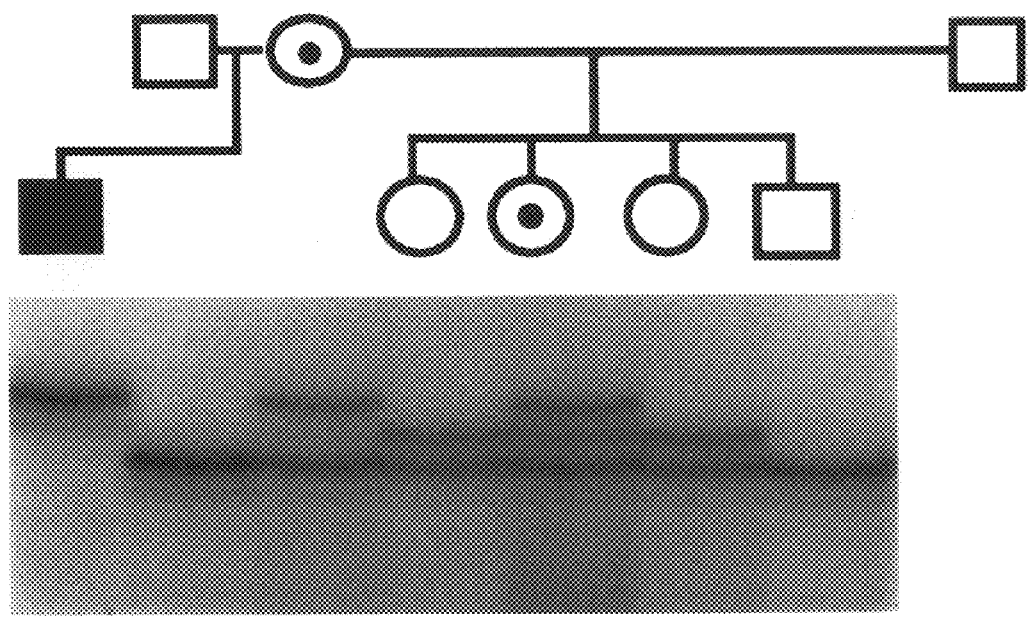
FIG. 9b shows GGAA tetra-nucleotide tandem repeat in an AHC affected family showing Mendelian inheritance of the polymorphism.
Figure 9C:
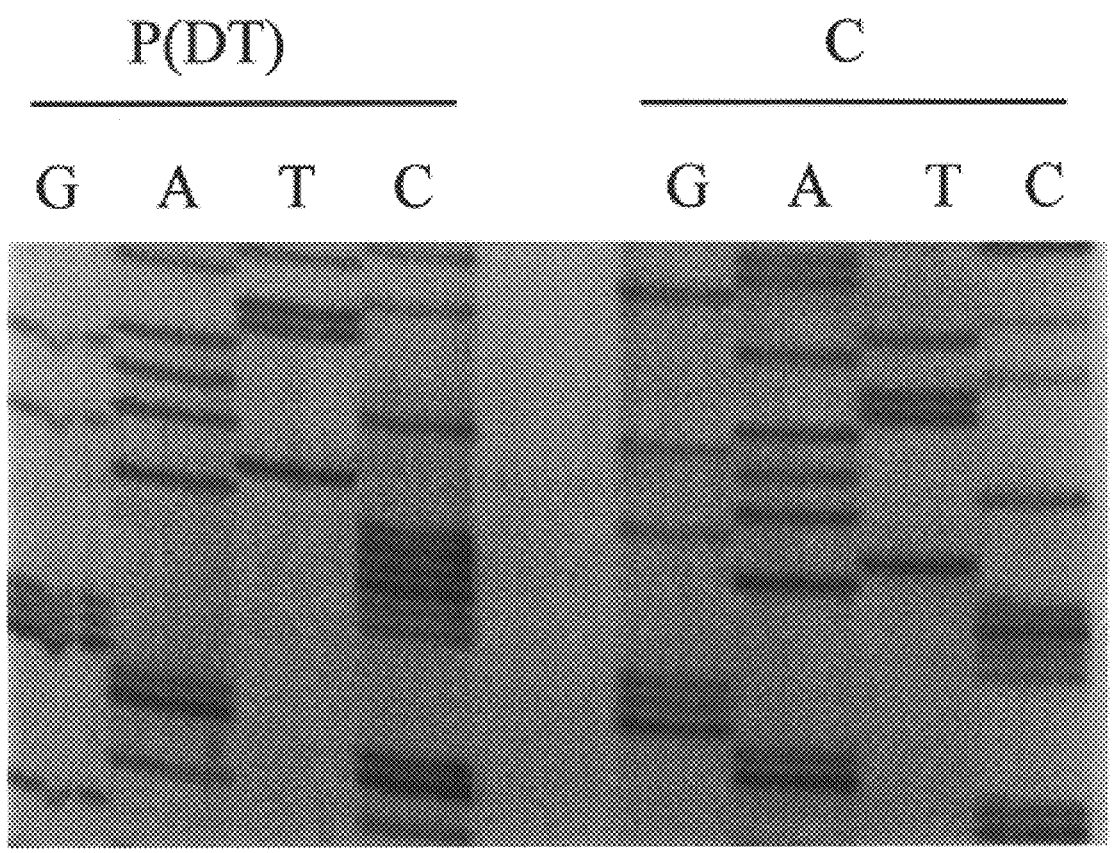
FIG. 9c shows the results of amplication and sequencing of the 266 bp fragment of DNA for patient DT.
Figure 9D:
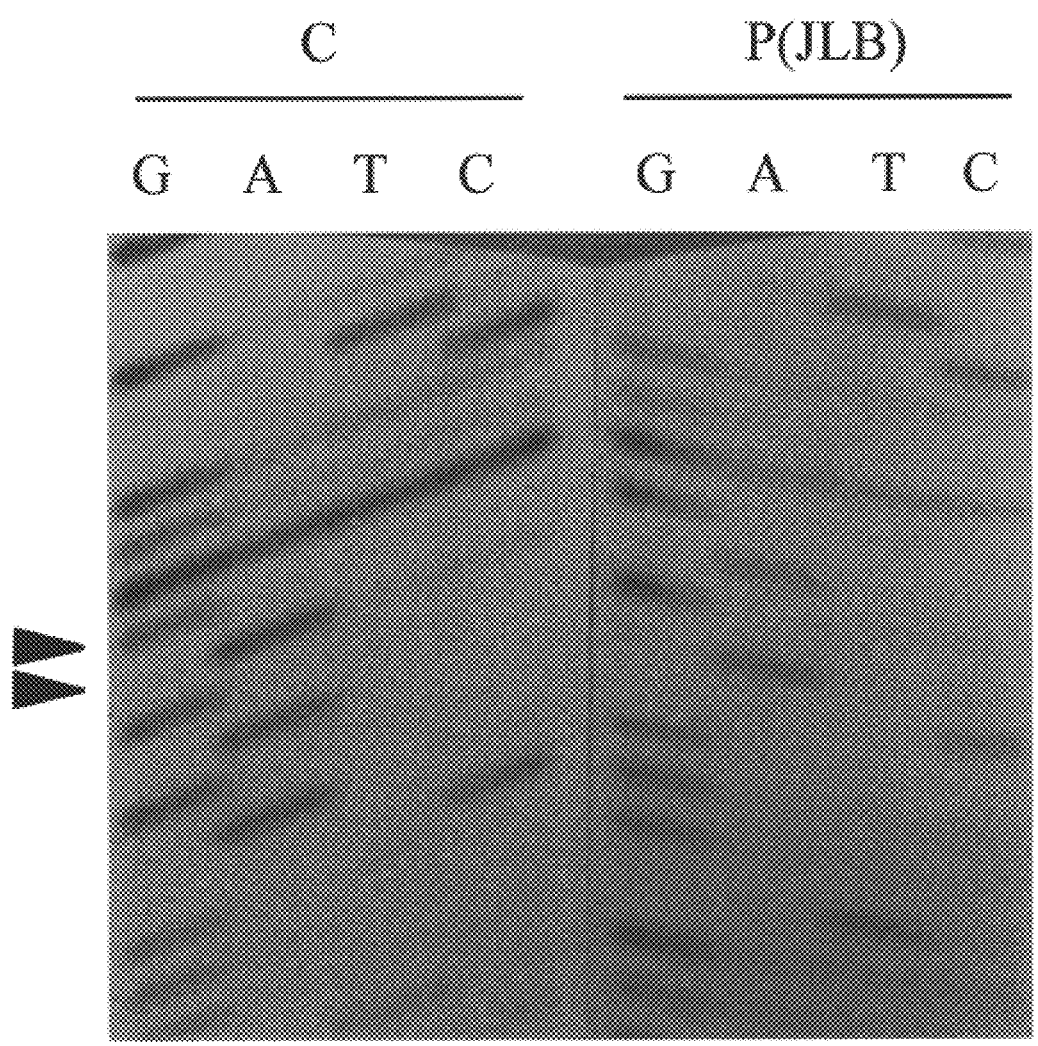
FIG. 9d shows the results of amplication and sequencing of the 201 bp fragment of DNA for patient JLB.

Two potentially polymorphic short tandem repeats were identified from the genomic sequence: a GGAA tetra-nucleotide tandem repeat was found between positions −1494 and −1398 of the 3.4 kb fragment (FIG. 7A) and a CA dinucleatide repeat was found in the intron between positions 4334 and 4372. The GGAA tetra-nucleotide tandem repeats is polymorphic in the population (FIG. 9A) and segregates in a Mendelian fashion (FIG. 9B).

FIG. 9 shows polymorphisms and mutations in DAX-1 gene. Nineteen DNA samples from different individuals show GGAA tetra-nucleotide tandem repeat polymorphisms (FIG. 9a). Samples 6 and 15 are from female individuals and the rest are from males. GGAA tetra-nucleotide tandem repeat in an AHC affected family shows Mendelian inheritance of the polymorphism (FIG. 9b). The 266 bp fragment of DNA was amplified with primers 3107 and 2851 and sequenced (FIG. 9c). Patient DT shows an additional two cytosine residues compared with control. The arrow points to the normal control without these two additional cytosines. The 201 bp fragment of DNA was amplified with primers 3557 and 3603 and sequenced (FIG. 9d). The arrow points to the two nucleotides (AG) which are deleted in patient JLB. The 201 bp fragment of DNA was amplified with primers 3557 and 3603 and sequenced (FIG. 9e). The arrow points to the mutation in the patient's DNA sequence, resulting in TAA instead of normal control sequence of TAC.

Figure 9E:
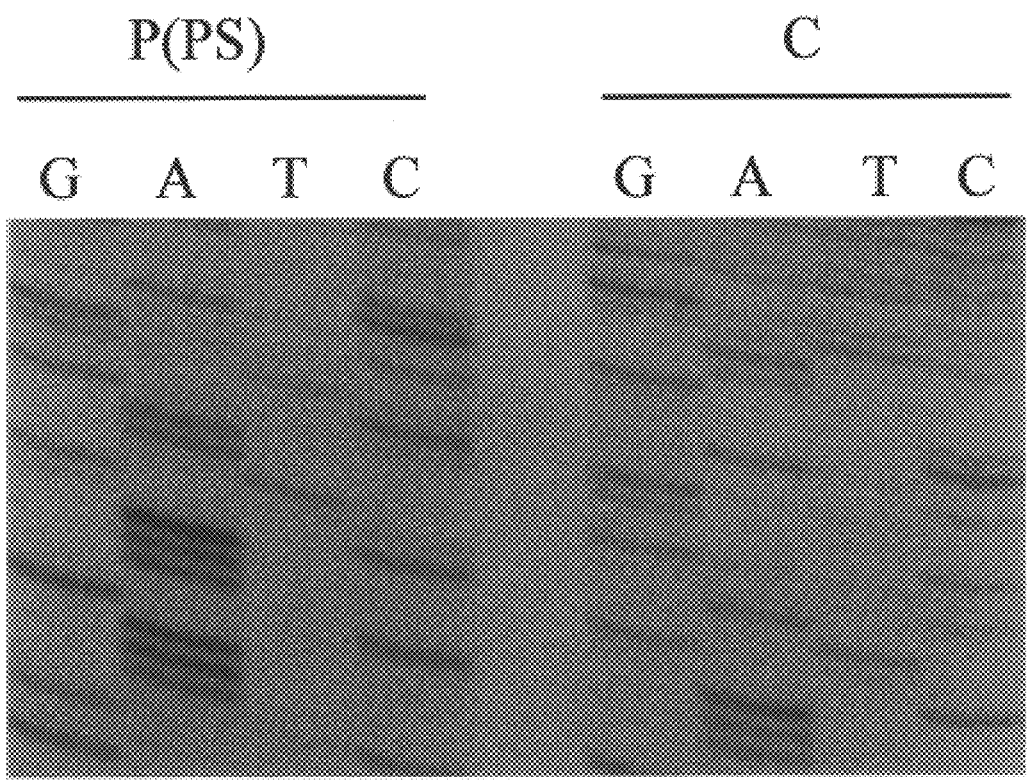
FIG. 9e shows the results of amplication and sequencing of the 201 bp fragment of DNA for patient PS.

DNA samples from male patients with isolated AHC were screened by SSCP and regions with altered SSCP patterns were sequenced. In DNA from patient DT a 2 bp insertion of cytosine nucleotides was noted between nt. positions 6231 and 6232 in the normal sequence of the second exon (FIG. 9C) and in DNA from patient JLB a 2 bp deletion (AG) was identified between nt. 1733 to 1734 of the normal sequence for the first exon (FIG. 9D), both mutations causing the frame shift and pre-mature termination. A transversion at position 1852, which changed codon from TAC (Tyr) to TAA (stop) (Y9lX) in the first exon of the gene was detected in two AHC patients, PS and RH, who were from different generations of the same family (FIG. 9E). A nucleotide transition at position 2077 changed codon 166 from CGG to CGA in the first exon, and was found in several isolated AHC patients and in normal controls. Since CGG and CGA encode the same amino acid, arginine, this nucleotide change represented a polymorphism.

Figure 10:
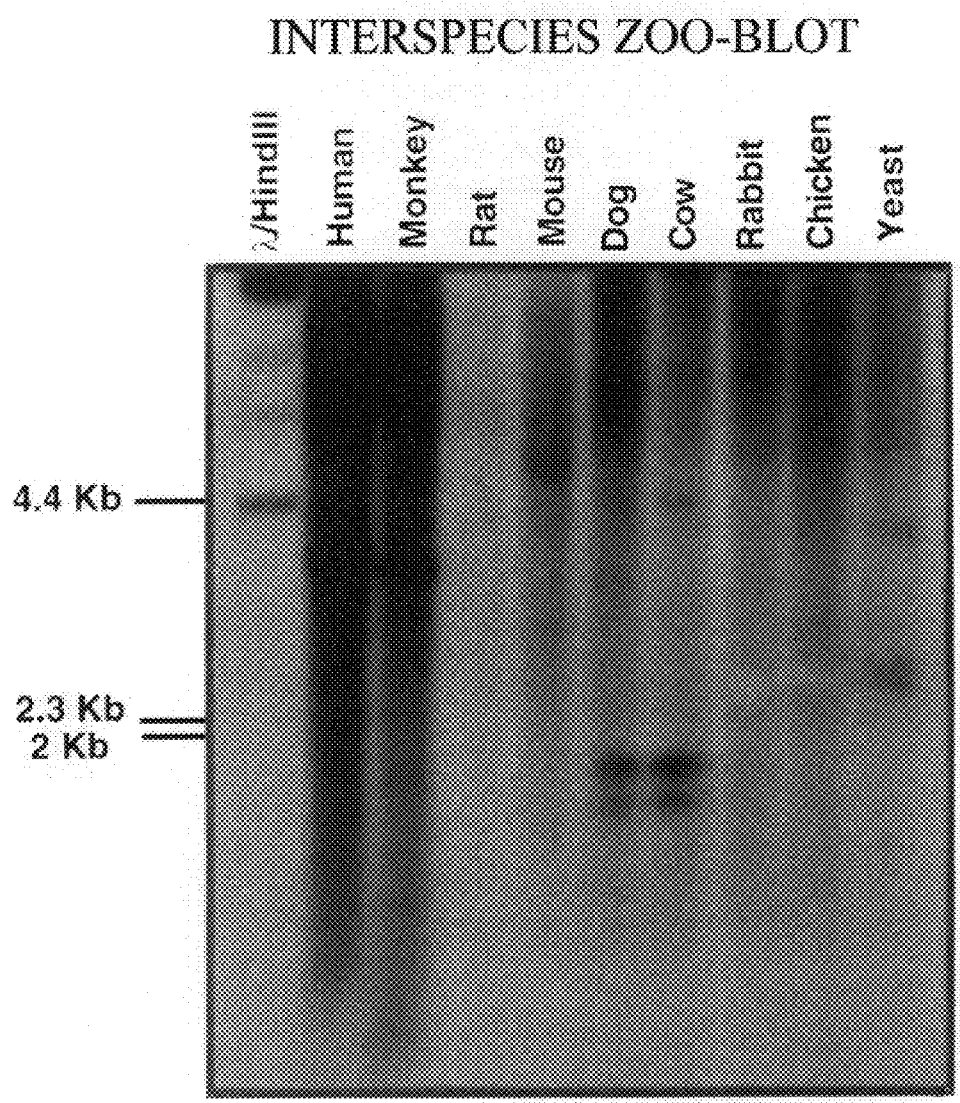
FIG. 10 is a multiple interspecies zoo blot.

Interspecies zoo blot analysis. An interspecies zoo blot of EcoRI digested genomic DNA from several species was analyzed. Results demonstrated that the human DAX-1 cDNA probe hybridized to all the species represented on the membrane (FIG. 10). The genomic DNA samples from human, monkey, rat, mouse, dog, cow, rabbit, chicken and yeast were digested by EcoRI and hybridized with a DAX-1 cDNA probe from the 1.6 kb SacI fragment which contains entire first exon of the DAX-1 gene. The numbers on the left side of the blot represent the sizes of the markers (FIG. 10).

The human and monkey DNAs revealed bands of similar sizes and signal intensity. DAX-1 appeared to be less well conserved between primates and the other species. The most striking feature of this blot was the hybridization of the human DAX-1 probe with yeast genomic DNA, showing five bands in the yeast. Another Southern blot containing yeast genomic DNA isolated in our lab showed the same result (data not shown).

We determined the genomic structure of the DAX-1 gene by sequencing three EcoRI restriction fragments totaling more than 8.8 kb. These fragments had been previously shown to be contained in a cosmid used to clone the DAX-1 cDNA by a genomic scanning strategy. Sequencing of these DNA fragments showed that the DAX-1 gene consists of two exons separated by a 3.4 kb intron. The promoter region of the gene contains a putative SF-1 response element, as well as a putative TATA box and several Spl sites. Knowledge of the genomic sequence permitted us to develop an SSCP strategy for rapid mutation detection, and three new mutations were identified. Polymorphisms, including sequence tandem repeats, that may be useful for linkage analysis in families with an affected individual, but no known mutations, have also been identified in the DAX-1 gene. An interspecies zoo blot indicates that there may be a DAX-1 related gene in the yeast genome.

The CCGAGGTCA sequence, which is located 175 bases upstream of the initiation codon, is a putative SF-1 response element. SF-1 is a member of the nuclear hormone receptor superfamily that regulates the expression of many steroidogenic enzymes, such as cholesterol side chain cleavage enzyme (SCC), steroid 21-hydroxylase, and the aldosterone synthase isozyme of the steroid beta-hydroxylase. SCC is expressed in all steroidogenic tissues and catalyzes the initial and rate-limiting step in the biosynthesis of steroid hormones. In contrast, the other two hydroxylases are only expressed in the adrenal cortex where they largely determine the unique ability of this tissue to produce corticosteroids.

All of these steroidogenic hydroxylases have SF-1 responsive elements in the promoter region of the genes, with AGGTCA as core sequence. Disruption of the Ftz-F1 gene encoding SF-1 in the mouse precludes adrenal and gonadal development. In mice homozygous for a null mutation in the SF-1 locus, the adrenal glands and gonads fail to develop and the mice die of adrenal insufficiency. AHC patients who have deletions involving the DAX-1 gene or a mutation within this gene also show a phenotype with failure of the adrenal cortex to develop normally and adrenal insufficiency. Interestingly, both SF-1 and DAX-1 are expressed in many of the same tissues such as the adrenal cortex, testis and ovaries. This raises the possibility that SF-1 may directly regulate DAX-1 gene expression.

Investigation of the Ftz-F1 knock-out mice showed that they lacked transcripts for three gonadotrope-specific markers: LHb, FSHb and the receptor for gonadotrophin releasing hormone. The knockout mice also exhibited grossly abnormal ventromedial hypothalamic nucleus structure.

Many of the patients with AHC also exhibit hypogonadotropic hypogonadism, and recently we have shown that DAX-1 is expressed in the hypothalamus and pituitary. These observations provide additional evidence consistent with the hypothesis that SF-1 may be involved in the regulation of DAX-1 gene expression.

Figure 11:
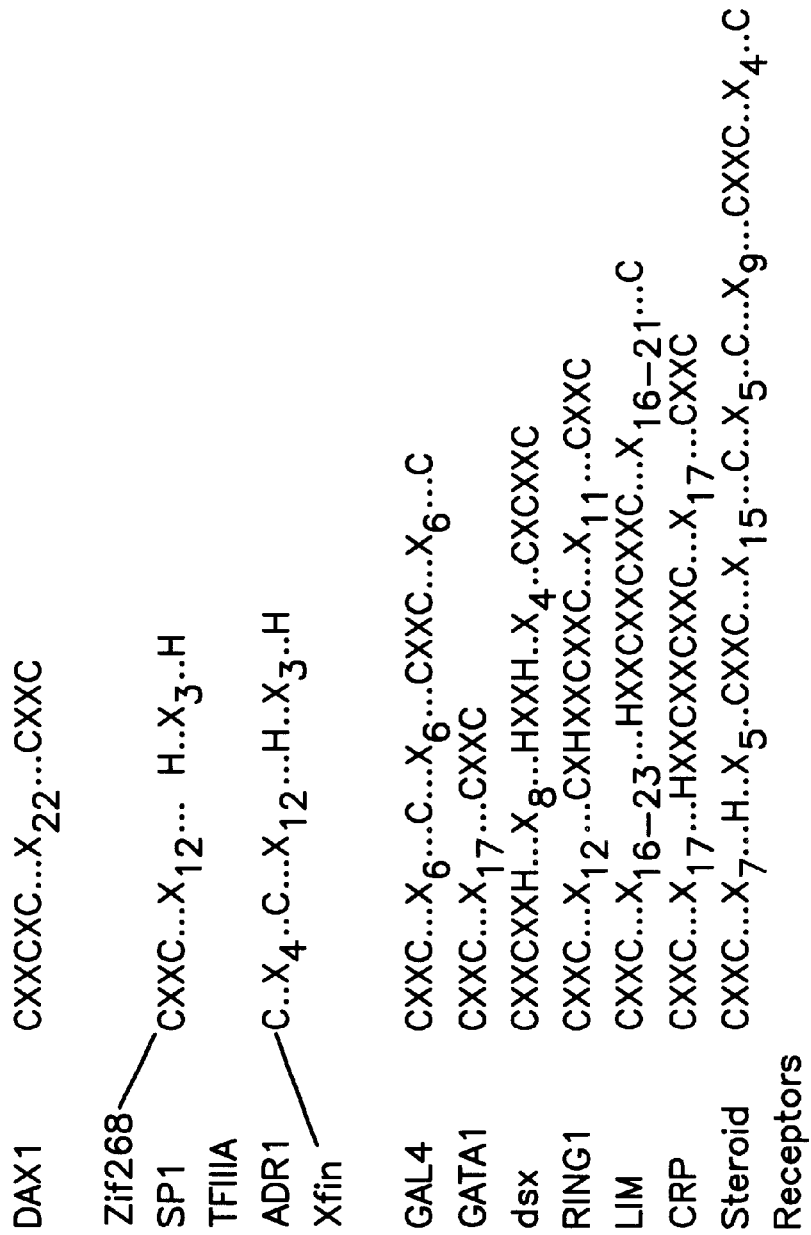
FIG. 11 is a comparison of zinc coordinating domains of DNA binding proteins.

The DNA binding domain of the nuclear hormone receptor superfamily usually contains 66 amino acids and is rich in lysine, arginine and cysteine residues. This domain is highly conserved among superfamily members and a number of residues are invariantly conserved throughout evolution. The positions of the key cysteine residues are absolutely conserved yielding a motif of two C2C2 domains: CXXC . . . X7 . . . H . . . X5 . . . CXXC . . . X15 . . . C . . . X5 . . . C . . . X9 . . . CXXC . . . X4 . . . C. The DNA binding domains of several nuclear receptors have been crystallized demonstrating that each C2C2 structure chelates a single Zn2+ ion forming a structure termed a zinc finger. Within the putative DNA binding domain in the N-terminus of DAX-1, an unusual zinc finger motif has been identified, containing two C2C2 zinc fingers (CXXCXC . . . X22 . . . CXXC) within three and half tandem repeats of a 65 to 67 amino acid motif. Although the DAX-1 zinc finger appears to be unique, it is consistent with the other DNA binding domain structural motifs in other superfamily members. FIG. 11 is a comparison of zinc coordinating domains of DNA binding proteins. The single letter designations are: C, Cys; H, His; and X is any amino acid. Subscripted letters represent the numbers of the amino acids in the segment.

The DNA binding domain of all nuclear hormone receptors cloned to date are encoded by genes containing several introns except for COUP-TF. The DNA binding domain of COUP-TF is encoded by a gene with a single intron and it has been suggested that COUP-TF is an ancestral receptor based on the simple genomic organization. DAX-1 also shows this simple organizational pattern.

The members of the nuclear receptor gene superfamily are identified by the three conserved structural features that separate these proteins from other transcription factor families. The conserved DNA binding domain is designated region I and regions II and III are located in the ligand binding domain. The functions of regions II and III are still unknown, but may involve dimerization, transactivation or transrepression along with ligand binding. Of the many mutations identified to date in the DAX-1 coding sequence only two mutations have been observed that alter single amino acids. One is a missense mutation that results in an Arg to Pro change at position 267 and the other is a deletion of three base pairs of DNA causing the loss of the Val at position 269. Interestingly, both of these mutations are within the conserved region II in the ligand binding domain. Thus, the ligand binding domain of DAX-1 appears indispensable for the function of the protein.

It has been demonstrated that many if not all nuclear hormone receptors are functional in yeast. This suggests that the machinery required for nuclear receptor transcriptional function is conserved from yeast to mammals. This has been surprising since no nuclear receptor-like proteins have been identified in yeast. However, our data suggest the existence of a DAX-1-like gene in yeast. Thus, the components of the transcriptional machinery required to interact with the ligand binding domain of DAX-1 or a DAX-1-like protein may be normally expressed in yeast, and these same components may be utilized by heterologously expressed mammalian nuclear receptors.

The nuclear receptors have been grouped into three subfamilies depending upon the relative conservation of the DNA binding domain. The putative DNA binding domain of the DAX-1 gene is composed of three and half repeats of a 65–67 amino acid motif, which contains two potential novel zinc finger structures. This domain shows no similarity to any other nuclear receptor indicating that it defines a new class within the superfamily. The simplicity of genomic structure of the DAX-1 gene and possible existence of a DAX-1 related gene in the yeast, the most primitive eukaryotic organism, suggests that the DAX-1 gene may be the most primordial receptor which has been identified to date.

The complete sequencing of 8.8 kb of the DAX-1 gene has given us insight into the structure and function of the encoded protein. In addition, it has provided improved methods for mutation and linkage analyses that will be of value to patients with X-linked AHC and their families.

Example 3

This experiment was to determine if DAX-1 was expressed in the nervous system, particularly in the hypothalamus and pituitary, in order to better understand the pathogenesis of the HH that is frequently associated with X-linked AHC.

Materials and Methods

Northern Blotting

A human multiple tissue northern blot was purchased from Clontech (cat. 7759-1, lot 52715; Clontech, Palo Alto, Calif.). The northern blot contained 2 µg of poly A+ RNA per lane from various human tissues. The 1.6 kb SacI genomic DNA fragment, which included the first exon of the DAX-1gene, was used as the hybridization probe. The northern blot was prehybridized in 5×SSPE, 10×Denhardts, 2% SDS, and 8–10 µg/ml sheared human placental DNA, for 3 hours. The probe was labeled with a32P-dCTP using the random hexamer primer labeling method, and was preassociated with 8–10 µg/ml sheared human placental DNA in 5×SSPE, 10×Denhardts, and 2% SDS for 3 hours. The hybridization was carried out at 65° C. for 18–20 hours. Following hybridization, the blot was washed in 2×SSC, and 0.05% SDS at room temperature for up to 20 min. If required because of excess residual radioactivity, a second wash in 2×SSC, and 0.1% SDS was performed for up to 15 min. at 65° C.

Cell Lines and cDNA Libraries

A human adrenocortical carcinoma cell line, NCI-H295 was obtained from the American Type Culture Collection (ATCC; Rockville, Md.). The following human cDNA libraries were purchased from Clontech (Palo Alto, Calif.): fetal adrenal (dgtllHL1118b); hypothalamus (lgt11 HL1172B); kidney (lgt11 HL1071b); liver (lgt11 HL1115b); and testis (lgt11 HL1161a). Human poly A+ RNA, prepared from total adult brain (6516-1), fetal brain (6525-1), pituitary (6584-1) and placenta (6518-1), was purchased from Clontech and was used for RT-PCR preparation of cDNA.

RNA Isolation

Total RNA was isolated from 1×108 NCI-H295 cells by the guanidinium thiocyanate method using Promega RNA AgentsO RNA Isolation Kit (Promega, Madison, Wis.).

Reverse Transcription—Polymerase Chain Reaction (RT-PCR)

The DAX-1 transcript was detected by reverse transcription of mRNA from tissues and from cultured cells, with amplification of the resultant cDNA by PCR (RT-PCR) amplification. For reverse transcription of the RNA (100 ng each), the reaction mixtures contained 2 µl of random hexamer (300 ng/µl), 2 µl of oligo (dT) (300 ng/µl), 2 µl of 20 mM DTT, 1.6 µl of 25 mM dNTP, 4 µl of 10×buffer (750 mM KCL, 30 mM MgCl2 and 500 mM TrisHCl pH 8.3, 0.5 µl of RNAsin (Promega, Madison, Wis.), 1 µl of M-MLV (GIBCO BRL, Gaithersburg, Md.), and water to bring the total volume to 40 µl. The reaction was carried out at 70° C. for 5 min. then 37° C. for 90 min. For amplification of a 251 bp fragment of the DAX-1 cDNA after RT, the primer pair was selected, such that primer 2937 (5'-AAGGAGTACGCCTACCTCAA-3') (SEQ ID NO.: 3, positions 1360–1379) was located in the first exon of the DAX-1 gene and 2851 (5'-TCCATGCTGACTGTGCCGAT-3') (complement of SEQ ID NO.: 3, positions 1591–1610) was located in the second exon; therefore, any contamination from genomic DNA or unprocessed RNA would have been detectable by its larger size. Amplification conditions were as follows: 5 min at 95° C. without Taq polymerase, then 0.5 min. denaturation at 94° C., 0.5 min. annealing at 57° C. and 0.5 min. extension at 72° C. for 32 cycles using Taq polymerase (Boehringer Mannheim) and amplification buffer (Perkin Elmer).

Southern Blotting of cDNA Gel

The RT-PCR products were separated electrophoretically on a 2% agarose gel containing ethidium bromide (10 µg/100 ml) in 1×TBE. The gel was transferred to Biodyne B membrane (GIBCO BRL) and was prehybridized in 5×SSPE, 10×Denhardt's, 2% SDS, and 8–10 mg/ml sheared human placental DNA for 3 hours. The membrane was hybridized with a probe consisting of the full length cDNA of DAX-1. The probe was labeled with 32P-dCTP, using the random hexamer primer labeling method, and was preassociated with 8–10 mg/ml sheared human placental DNA in 5×SSPE, 10×Denhardt's, and 2% SDS for 3 hours. The hybridization was carried out at 65° C. for 18–20 hours. Following hybridization, the blot was washed in 2×SSC and 0.05 % SDS at room temperature for up to 20 min. A second wash in 2×SSC and 0.1% SDS was performed for up to 15 min. at 65° C.

Expression of DAX-1 in Human Tissues

A Northern blot containing RNA from a variety of human tissues was hybridized with the SacI restriction fragment containing the first exon of the DAX-1 gene. The results show that the gene is strongly expressed in testis and weakly expressed in ovary. Two different RNA species were observed, one approximately 1.9 kb in length and the other about 6 kb in size. The 1.9 kb band was consistent with the size of the cDNA. The 6kb band, but not the 1.9 kb band, hybridized with a probe containing only intronic sequence from the DAX-1 gene, indicating that the 6 kb band represented unprocessed RNA.

Expression of DAX-1 in Human Hypothalamus, Pituitary Gland and an Adrenocortical Carcinomal Cell Line RT- PCR amplified a 251 bp DAX-1 sequence from mRNA and cDNA libraries. Despite the observation of unprocessed RNA in the Northern blot, only the smaller amplification product from processed mRNA was observed, presumably due to reduced efficiency of amplification of the longer sequence containing the intron. RT-PCR amplified the 251 bp DAX-1 product from mRNA extracted from total adult brain, total fetal brain, pituitary gland, and the human adrenocortical carcinoma cell line, NCI-H295, as well as from cDNA libraries of the hypothalamus, fetal adrenal gland, and testis. The DAX-1 product was negative in mRNA from placental tissue and cDNA libraries from liver and kidney. In order to increase the sensitivity of this analysis a Southern blot was prepared from the gel. Placenta, liver and kidney remained negative for DAX-1.

DISCUSSION

We provide evidence that DAX-1 is not only expressed in mRNA from adrenal and gonadal tissues, but also from adult and fetal brain. More specifically, DAX-1 is expressed in the hypothalamic-pituitary axis. These experiments, together with the clinical features of patients with DAX-1 mutations, directly link DAX-1 to the normal development of the adrenal cortex and gonadal tissue.

We also demonstrated that DAX-1 is expressed in a human adrenocortical carcinoma cell line, NCI- H295, that is a steroidogenic model for the human fetal cortex , and expresses most of the enzymes associated with adrenal steroidogenesis. The genes encoding the steroidogenic enzymes in this cell line respond to stimulation by second messenger pathways in a manner similar to the human adrenal cortex. Investigation of this cell line will help us to understand the regulation of DAX-1 expression, and the role of DAX-1 in the fetal adrenal. In addition, DAX-1 may be a useful marker for tumor cell transformation in the specific tissues of the hypothalamic pituitary-adrenal/gonadal axis.

The development of the mammalian reproductive system requires elaborate interactions within the hypothalamic-pituitary-adrenal/gonadal axis. The gonadal steroids, essential reproductive hormones, are produced by testes and ovaries under the regulation of the tropic hormones LH and FSH. The release of LH and FSH by the gonadotropes of the anterior pituitary gland is stimulated by GnRH, which is secreted by specific neurons located within the hypothalamus. A number of neuronal centers deliver the modulatory inputs to GnRH neurons that transduce the elaborate effects of behavioral and environmental stimuli on the reproductive axis. All of these complex interactions are modulated at both the hypothalamic and pituitary levels through negative and positive feedback regulation. The association of HH with AHC, along with our data showing that DAX-1 is expressed in hypothalamus and pituitary gland, suggest that DAX-1 may be involved with the normal development of GnRH neurons and gonadotropes or the regulation of GnRH and gonadotropin expression. Since pulsatile administration of GnRH to males with HH associated with AHC can result in testosterone secretion, the action of DAX-1 would appear to be proximal to GnRH in the hypothalamus and/or pituitary.

Interestingly, the expression pattern of DAX-1 is very similar to that for steroidogenic factor-1 (SF-1). SF-1 is an orphan nuclear receptor that is an essential regulator of steroid hydroxylase gene expression, and is expressed at multiple levels of the reproductive system from hypothalamus and pituitary to the adrenal cortex and gonads. SF-1 has been demonstrated to be essential for development of the adrenal cortex, gonads and the ventromedial nucleus of the hypothalamus. We have shown previously that the promoter region of the DAX-1 gene contains a putative SF-1 response element and now we show that DAX-1 is expressed in hypothalamic-pituitary-adrenal/gonadal axis. Collectively, these results strongly suggest that DAX-1 may be regulated by SF-I or may act in concert with SF-1 as a co-regulator at various levels in gonadal and adrenal development.

Example 4

In our laboratory, the JK2 genomic DNA fragment, which is a genetic marker telomeric to the GK locus and most centromeric to the AHC locus, was used to screen a human chromosome X cosmid library (Guo et al., 1995). Two positive clones were identified from this library and the end fragments of these two positive clones were used for chromosome walking in the telomeric portion of this region within Xp2l. The same strategy was repeated until a cosmid contig covered the region between the marker YHX133R and K23-b2, a total of approximately 160 kb. The markers, JK2, YHX133L, A107E5R, QST59 and YHX133R, were used to characterize the 15 cosmid clones in the contig. The genomic scanning strategy, termed cDNA amplification for identification of genomic expressed sequences (CAIGES), developed in our laboratory (Guo et al, 1993), was used to identify expressed sequences in these cosmid clones.

Figure 14:
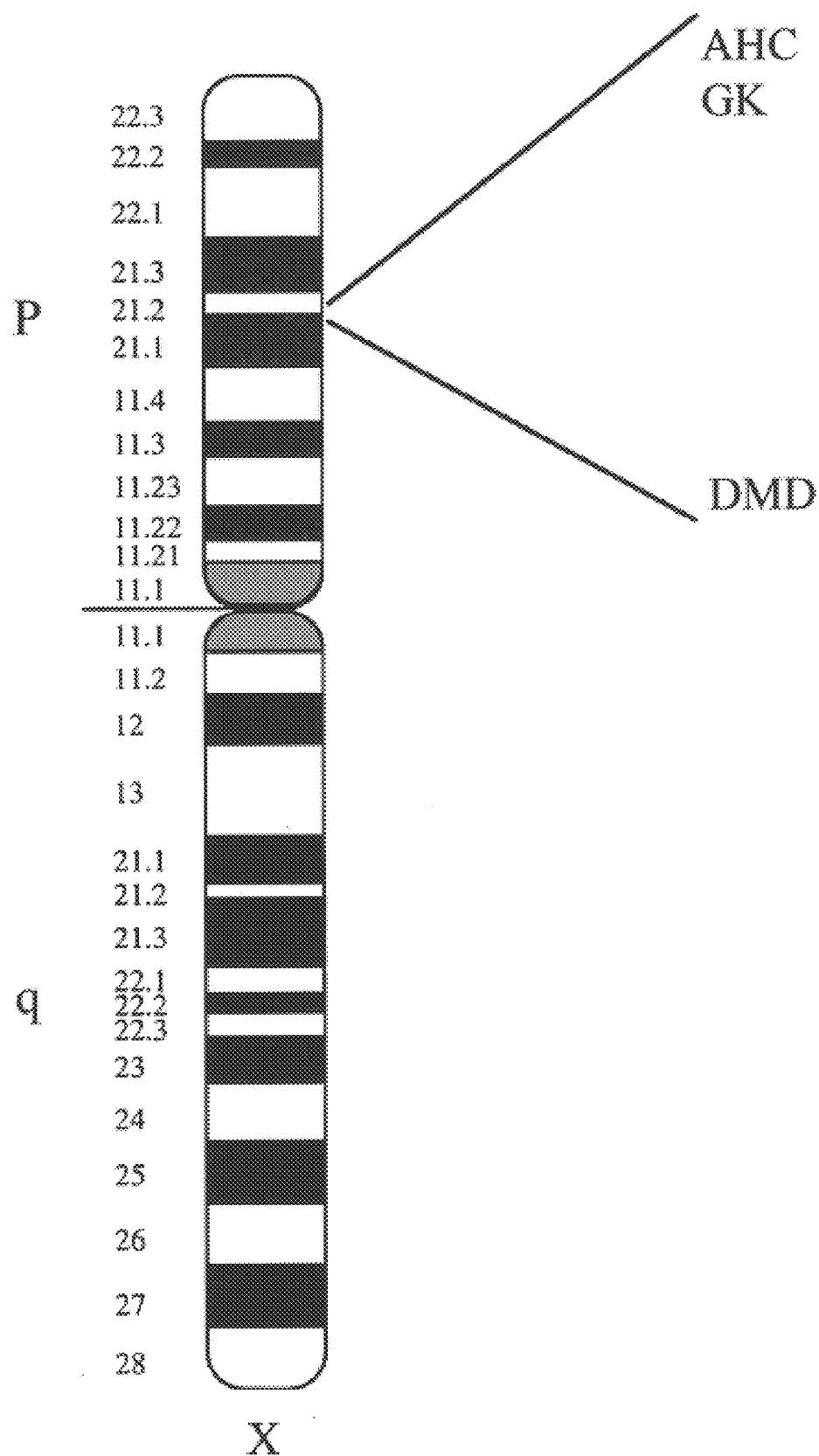
FIG. 14 shows relative locations of the genes responsible for cytomegalic adrenal hypoplasia congenita (AHC), glycerol kinase deficiency (GK), and Duchenne's muscular dystrophy (DMD) within the X chromosome.

FIG. 14 shows relative locations of the genes responsible for cytomegalic adrenal hypoplasia congenita (AHC), glycerol kinase deficiency (GK), and Duchenne's muscular dystrophy (DMD) within the X chromosome.

Figure 15:
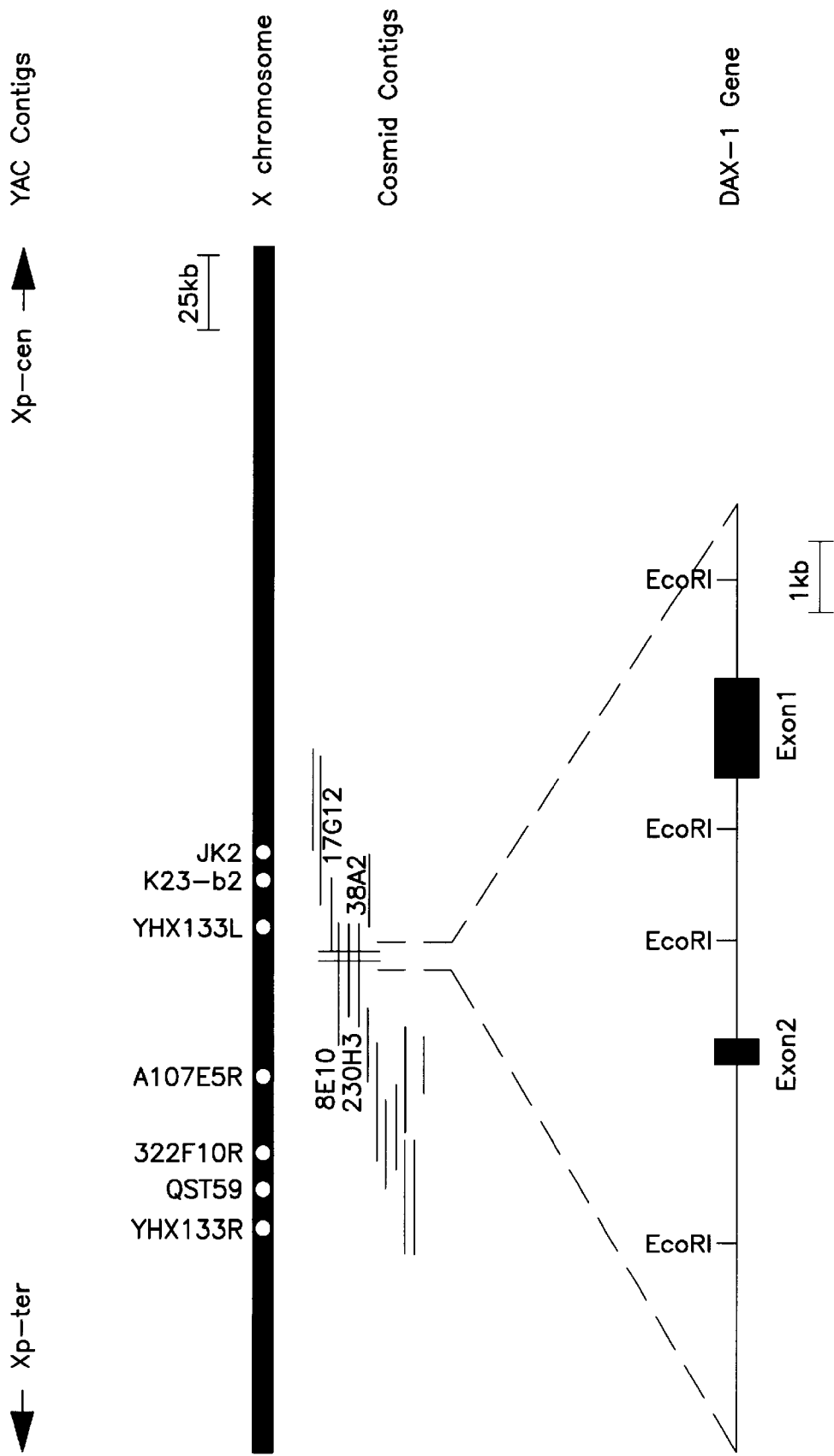
FIG. 15 shows positional cloning of the DAX-1 gene in Xp21.

FIG. 15 shows positional cloning of the DAX-1 gene in Xp21. The end of the short arm of the X chromosome is to the left of the figure (Xp-ter) and the centromere is to the right (Xp-cen). The markers within the region are indicated along the X chromosome. The cosmid contig is illustrated below the X-chromosome and the cosmids containing at least a fragment of the DAX-1 gene are named. The genomic structure of the DAX-1 gene is illustrated at the bottom of the figure. (Adapted from Guo et al., 1995)

Figure 16:
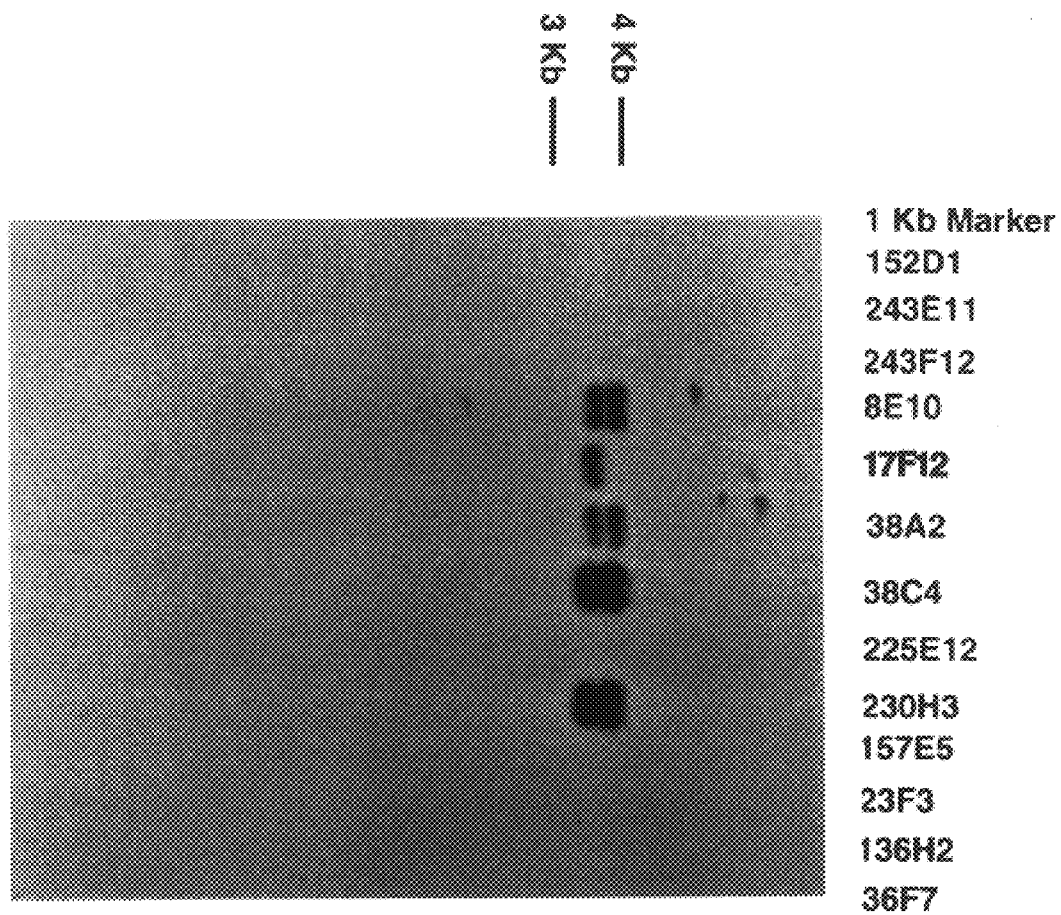
FIG. 16 shows results of a Southern blot of a restriction digest from contig cosmids hybridized with the PCR amplified, labeled human fetal adrenal cDNA library.

The cosmid clones in the contig were digested with EcoRI and hybridized with a polymerase chain reaction (PCR) amplified radiolabeled human fetal adrenal cDNA library. Two bands (4 kb and 3.4 kb) were positive in four of these clones (8E10, 38A2, 38C4, 230H3) and one band (3.4 kb) was positive in one of these clones (17G12) (FIG. 16). Both fragments were subcloned and sequenced. An open reading frame was identified in each of these two fragments.

FIG. 16 shows results of a Southern blot of a restriction digest from contig cosmids hybridized with the PCR amplified, labeled human fetal adrenal cDNA library. The hybridizing bands in cosmid 8E10, 38C4 and 230H3 were 3.4 kb and 4 kb and the hybridizing band in cosmid 17G12 was 3.4 kb.

The 3.4 kb fragment was used to screen two human fetal adrenal cDNA libraries and eight positive clones were identified. After sequencing the eight cDNA clones, it was determined that their sequences were identical to the open reading frame of the genomic fragment.

Figure 17:
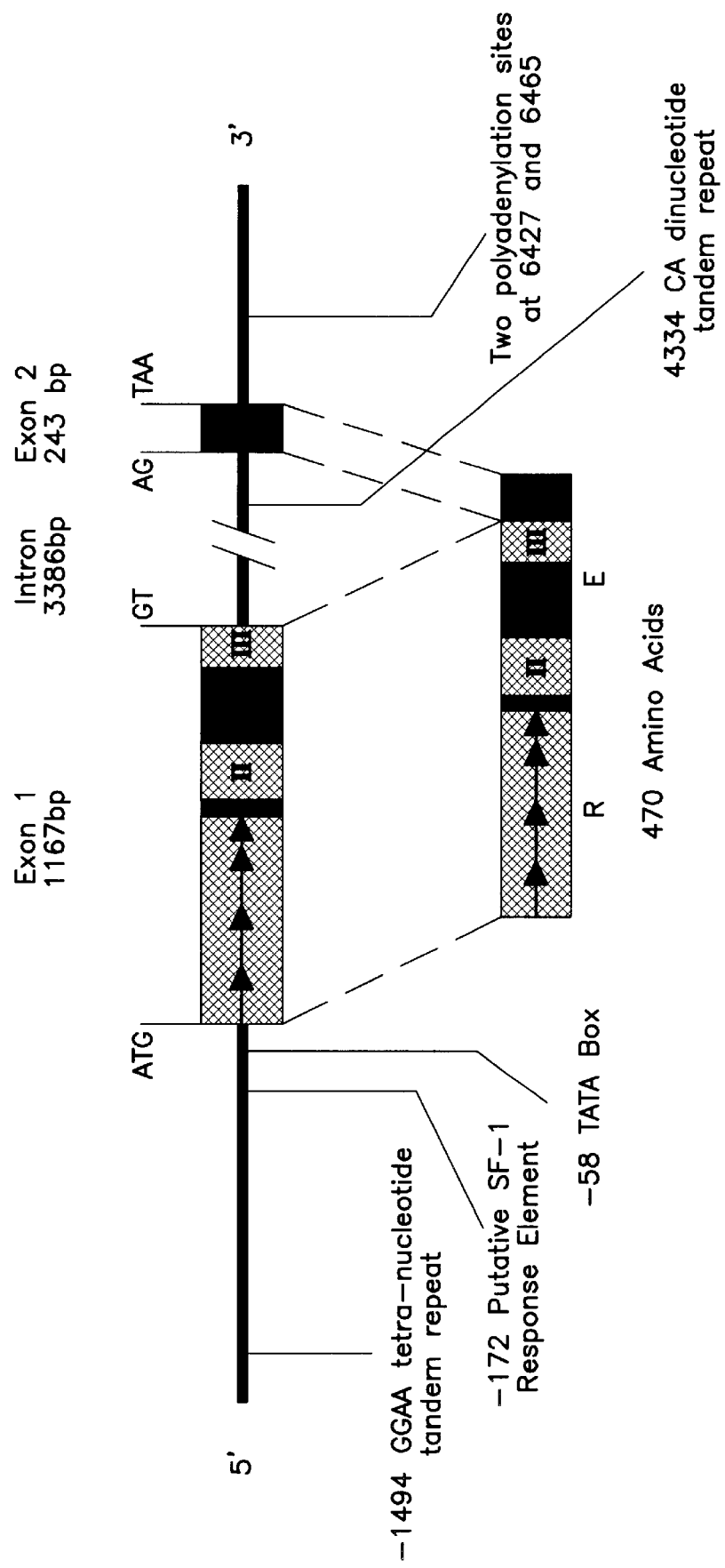
FIG. 17 shows the genomic structure of the DAX-1 gene.

The candidate gene responsible for AHC consists of two exons separated by a 3.4 kb intron (FIG. 17). It was determined that both the 4.0 kb and 3.4 kb fragments identified with the CAIGES method were fragments of the same gene with exon 1 contained in the 4.0 kb fragment and exon 2 in the 3.4 kb fragment. This gene was named DAX-1 based on its localization within the dosage sensitive sex reversal (DSS) locus and the AHC locus on the X chromosome (Zanaria et al, 1994).

FIG. 17 shows the genomic structure of the DAX-1 gene. Boxed structures represent the exons and include the relative positions of domains within the DAX-1 protein. The R domain is the unique amino-terminal domain which contains the repeated motifs and the two putative zinc fingers. The E domain is the ligand binding domain. Regions II and III are highly conserved regions defined within the ligand binding domain of all nuclear hormone receptors (Wang et al., 1989). The initiation codon, splice junctions, and termination codon are indicated. Other sequences of interest including the TATA box, putative steroidogenic factor 1 response element, polyadenylation sites, and polymorphic sequences are indicated.

The cDNA sequence of this gene contains an open reading frame of 1410 bp, predicting a protein of 470 amino acids. We found highly significant similarities between the carboxy-terminal region of DAX-1 and the ligand binding domain (LBD) of members of the nuclear hormone receptor superfamily.

Southern blot analysis of patients with AHC deletions provides strong indication for the involvement of the DAX-1 gene in X-linked AHC (Zanaria et al, 1994; Muscatelli et al, 1994; Guo et al, 1995). The cDNA clone was hybridized to genomic DNA isolated from AHC patients with deletions. In normal patient controls two bands were identified (4.0 kb and 3.4 kb); however, in AHC deleted patients this normal pattern was not present indicating that patients with AHC lack this gene.

To further prove that the DAX-1 gene was responsible for AHC we focused on patients with isolated AHC. Presumably, AHC in these patients is caused by point mutations or small DNA rearrangements. Several primer pairs designed from the coding sequence were used to amplify different portions of the coding region.

A deletion of eleven base pairs, resulting in a frame shift and premature termination, was identified in two brothers affected with AHC and HH (Zanaria et al., 1994). A single base pair deletion in the second exon was observed in two patients who came from different families. This deletion was detected by RsaI restriction pattern change after digestion of the PCR product (Guo et al., 1995).

Sequencing of the PCR product confirmed a single base pair deletion, resulting in a frame shift and premature termination. Recently, several other intragenic mutations in the DAX-1 coding region have been identified in patients with isolated AHC (Muscatelli et al, 1994) (see below).

Structural Features of the DAX-1 Gene Product. The DAX-1 gene encodes a member of the nuclear hormone receptor superfamily based on the presence of a conserved ligand binding domain present in its carboxy-terminus. Members of the nuclear hormone receptor superfamily are transcription factors that regulate a myriad of essential cellular processes. Many members of this superfamily, such as the steroid receptors (i.e. progesterone and glucocorticoid receptors), thyroid hormone receptors, and the receptors for lipophilic vitamins (i.e. retinoic acid and vitamin D3), regulate transcription in a ligand dependent manner (Evans, 1988; O'Malley, 1990; Beato, 1991; Green and Chambon, 1988, Baniahmad and Tsai, 1993; Truss and Beato, 1993; Baniahmad et al, 1994). Also included in the superfamily are the orphan receptors which have a not yet identified ligand or act in a ligand independent manner (O'Malley, 1990; O'Malley and Conneely, 1992; Power et al, 1992; Lydon et al., 1992; Conneely and O'Malley, 1994).

Sequence comparison of these proteins reveals a highly conserved domain structure which has been divided into regions A through F (Krust et al., 1986). The A/B region is the most amino terminal region and is least conserved between the receptors. Some receptors, such as the progesterone or glucocorticoid receptors, have A/B regions that are several hundred amino acids in length, while in some orphan receptors this region consists of only a few amino acids.

In terms of functionality, several laboratories have described transactivation domains within the A/B region (Hollenberg and Evans, 1988; Bocquel et al., 1989; Tora et al., 1989; Tasset et al, 1990).

Region C is the most highly conserved region and contains the DNA binding domain (DBD) which contains two zinc fingers (Cooney and Tsai, 1994; Glass, 1994). This highly conserved domain has also been termed region I (Wang et al., 1989). Region D, known as the hinge region, links the DBD to the ligand binding domain (LBD). This area is not well characterized, but it may contain a transactivation domain and regions required for transcriptional silencing in the thyroid hormone and retinoic acid receptors (Baniahmad et al., 1992; Baniahmad et al., 1993; Baniahmad et al. 1995).

Region E consists of the LBD, is contained in the carboxy-terminus, and is the second most conserved domain between family members. This region also contains many overlapping functional domains, including those required for nuclear localization, dimerization, and transactivation (Webster et al., 1988; Kumar et al., 1986; Picard et al., 1988; Guiochon-Mantel et al., 1989; Kumar and Chambon, 1988; Fawell et al., 1990; Lee et al., 1992). Two areas within the LBD have been identified which have a very high level of conservation and these have been termed regions II and III (Wang et al., 1989).

Although the functions of regions II and III are not yet clear, the strong conservation within these regions suggests that they may be important for ligand binding, dimerization, and/or transactivation. Based on the recently described crystal structure of the LBD of RXR, region III consists of helix 8 and the "loop" of amino acids just amino-terminal to this helix (Bourguet et al., 1995). The "loop" of amino acids between helices 7 and 8 has been shown to be a component of the interface between a RXR ligand binding domain homodimer (Bourguet et al., 1995). Thus, region III, or some fragment thereof, seems to play an important role in dimerization by serving as a component of the dimerization interface. The most carboxy-terminal region within nuclear hormone receptors is region F and is present in only a few family members such as RAR and ER. The function of this region is unclear. DAX-1 is a very unusual member of the nuclear hormone receptor superfamily in that it does not have the typical A-F region structure. Rather, it has what appears to be a novel domain containing two unique zinc finger structures in the amino terminus followed by a well conserved LBD in the carboxy terminal portion which is indistinguishable from the LBD of other superfamily members (FIG. 18).

Figure 18:
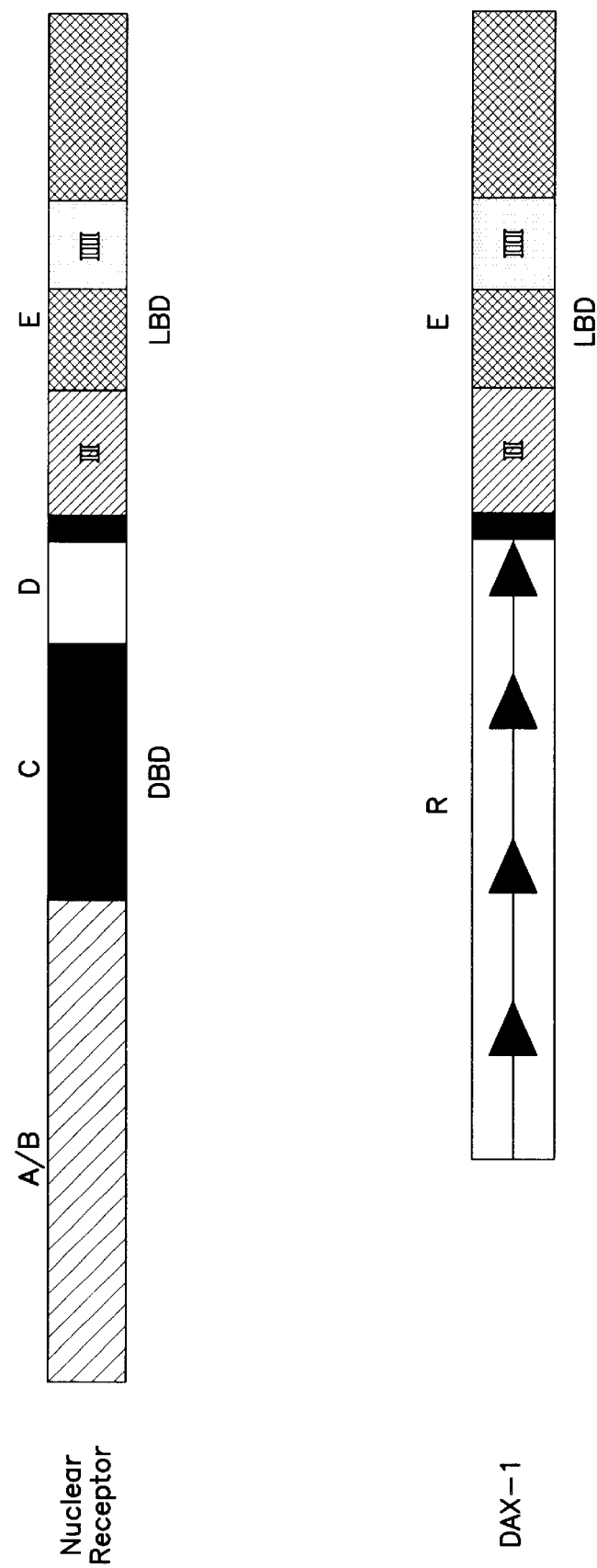
FIG. 18 shows a comparison of the domain structure of DAX-1 to a prototypic member of the nuclear hormone receptor superfamily.

FIG. 18 shows a comparison of the domain structure of DAX-1 to a prototypic member of the nuclear hormone receptor superfamily. The A through E domain structure of a nuclear receptor (Krust et al., 1986) is illustrated along with the R-E domain structure of DAX-1. The R domain is the unique amino-terminal domain which contains the repeated motifs and the two putative zinc fingers. The ligand binding domains (LBD) are aligned with the relative locations of regions II and III (Wang et al., 1989). The relative location of the DNA binding domain (DBD) of the nuclear receptor is also illustrated.

Figure 19:
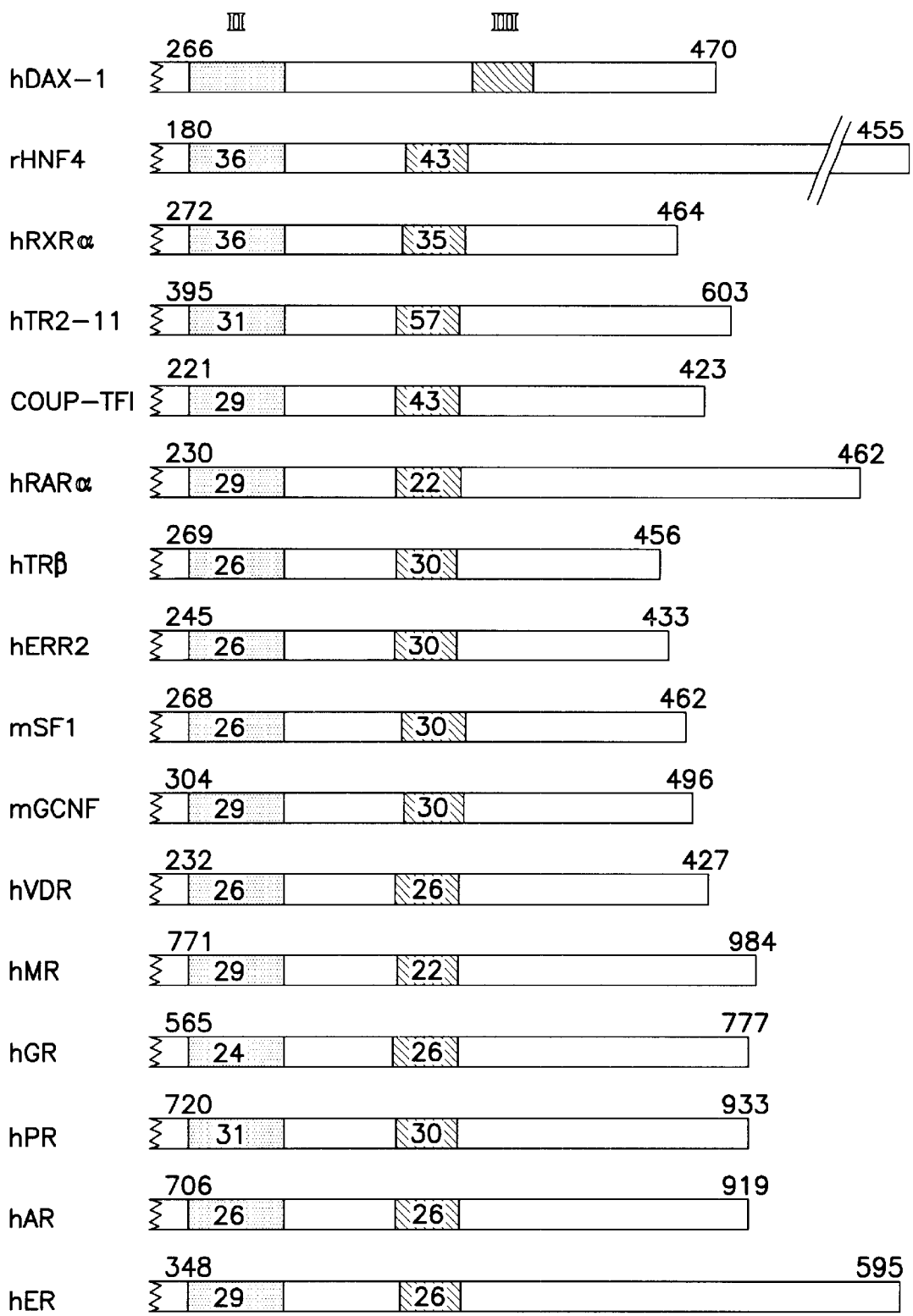
FIG. 19 shows a comparison of the ligand binding domain of DAX-1 to other members of the nuclear hormone receptor superfamily.

We have termed the amino-terminal domain, containing the repeated motif and the two putative zinc fingers, the "R" region. DAX-1 does not contain regions A through D, but has been classified as a member of the nuclear hormone receptor superfamily based on the presence of a highly conserved region E. Within the DAX-1 region E are the two well conserved regions II and III defined for classical members of the superfamily (FIG. 18). The highest similarities in amino acid sequence were observed with RAR, RXR, COUP, and TR2-11 and the similarities ranged from 42 to 52%. Analysis of the DAX-1 carboxy-terminus revealed that it contains an entire LBD with highly conserved regions II and III. Alignments of regions II and III within the LBD between DAX-1 and several other members of the nuclear hormone receptor superfamily are shown in FIGS. 19 and 20. The percentage of identical amino acids in region II ranges from 24 to 36% and in region III from 22 to 57%. The ranges of identical amino acids within the LBD regions is common for superfamily members containing the classical A-F domain structure. DAX-1 also contains the heptad repeats which are conserved in the nuclear hormone receptor superfamily (Zanaria et al., 1994). The heptad repeats have been proposed to play a role in the interface between receptor dimers (Forman and Samuels, 1990).

FIG. 19 shows a comparison of the ligand binding domain of DAX-1 to other members of the nuclear hormone receptor superfamily. The numbers within the boxed regions II and III indicate the percentage of identical amino acids within these regions.

FIG. 20 shows alignment of the amino acids within regions II and III. Several nuclear receptors are compared to DAX-1. Bold letters represent amino acids which are similar and dashed lines indicate identical amino acids.

Recently, with the solution of the 3-dimensional structure of the LBD of RXR it was shown that these heptads are not involved in dimerization (Bourget et al., 1995). However, the conserved nature of these repeats throughout the superfamily suggests that they have an important functional role. The AF-2 or t4 transactivation domain contained in the carboxy-terminus of nuclear hormone receptors is also present in DAX-1 (FIG. 21). This transactivation domain has been identified and characterized in many receptors including RXR, RAR, ER, and TR (Durand et al., 1994; Tate et al., 1994; Danielian et al., 1992; Baniahmad et al., 1995; Leng et al., 1995). Although the carboxy-terminal region of DAX-1 contains a conserved LBD, its amino-terminus is very unusual and we have proposed that this structure may be a novel DNA binding domain (Zanaria et al., 1994; Guo et al., 1995). The amino-terminal region is very rich in small amino acids such as glycine and alanine and is arranged in 3.5 tandem repeats of a 65–67 amino acid motif with cysteines in conserved positions (FIG. 22).

FIG. 21 shows a comparison of the AF-2 or t4 transactivation domain of DAX-1 to other nuclear hormone receptors. The conserved hydrophobic regions are boxed and the invariant glutamate residue is outlined. Asterisks represent the carboxy-terminus of the receptor. Numbers to the right of the alignment indicate the amino acid position within the receptor.

FIG. 22 shows that the putative DNA binding domain of DAX-1 is composed of 3.5 repeats of a 65–67 amino acid motif containing two zinc finger like structures. FIG. 22a shows alignment of the 3.5 repeats within the amino-terminus of DAX-1. Dashed lines indicate identical amino acids. Shaded boxes indicate the position of the conserved cysteines. Numbers to the right reflect the amino acid number within the DAX-1 coding sequence. Dots represent gaps inserted into the sequence during the alignment. FIG. 22b shows a comparison of the putative DAX-1 zinc finger to zinc fingers found in other double stranded DNA binding proteins.

No protein sequences with homology to the amino terminus of DAX-1 were identified in protein sequence database searches. The conserved positions of the cysteines within these repeats are consistent with a zinc finger structure which is novel, but has some similarities to other zinc coordination motifs contained in other double stranded DNA binding domains (FIG. 23)(Klug and Rhodes, 1987; O'Halloran, 1993).

FIG. 23 is a schematic of the DAX-1 protein illustrating the approximate location of various types of mutations causing AHC. Below the schematic is a Table containing all of the known mutations in the DAX-1 gene. The nature of each mutation is indicated. The numbers shown on the schematic correspond to the numbered mutations in the Table.

The high level of conservation in the DBD of classical members of the nuclear hormone receptor superfamily has allowed for the identification of many new receptors using low stringency hybridization with the relatively small region. However, since DAX-1 does not contain the typical nuclear receptor DBD, it would not be identified using these methods.

It appears that DAX-1 is the first identified member of a novel subfamily of the nuclear hormone receptor superfamily which contains this relatively unusual domain organization; whether this is the sole member of this subfamily or other members will be defined remains to be determined.

Patterns of Expression of DAX-1. As expected for a transcription factor required for adrenal gland development, DAX-1 is expressed in the fetal adrenal gland (Zanaria et al., 1994; Guo et al., 1995).

DAX-1 is also expressed in the adult adrenal glands, although at a much lower level than in the fetal gland (Guo et al., in press). Interestingly, DAX-1 is also expressed in the ovaries and testes, suggesting that DAX-1 may play a role in the regulation of steroidogenesis (Zanaria et al.). As a putative transcription factor expressed in steroidogenic tissues, DAX-1 is a candidate gene for the sex reversal locus, since DAX-1 is contained in the DSS region (Bardoni et al., 1994). We demonstrated that DAX-1 is also expressed in both the hypothalamus and pituitary gland; thus, DAX-1 is expressed at each level of the hypothalamic-pituitary-adrenal/gonadal axis. The expression of DAX-1 in the hypothalamus and pituitary gland suggests that interruption of the neuroendocrine expression of DAX-1 may be the cause of the HH that is often associated with AHC (Guo et al., 1995).

The pattern of expression of DAX-1 is very similar to steroidogenic factor-1 (SF-1), another member of the nuclear hormone receptor superfamily, that is essential for the development of the adrenal cortex, gonads, and ventromedial nucleus of the hypothalamus (Ikeda et al., 1993; Ikeda et al., 1994; Ingraham et al., 1994; Luo et al., 1994).

The many similarities between these two transcription factors in terms of their patterns of expression and functions suggest that they may act as coregulators and/or be components of a regulatory cascade required for adrenal and gonadal development. Consistent with this hypothesis, we have recently identified a putative SF-1 response element upstream of the TATA box in the 5' flanking region of the human DAX-1 gene.

Although we have determined that SF-1 is able to bind to this element in vitro, we have not yet characterized its significance in terms of the regulation of DAX-1 expression in vivo. When we searched for the existence of DAX-1 homologues in lower species we found that the human DAX-1 probe hybridized with genomic DNA from all species examined. The most striking feature of this analysis was the hybridization of the human DAX-1 probe with yeast genomic DNA, suggesting the existence of a yeast homologue of DAX-1. Many if not all nuclear hormone receptors are functional when heterologously expressed in yeast (Schena and Yamamoto, 1988; Metzger et al., 1988; McDonnell et al., 1989; Privalsky et al., 1990; Wilson et al., 1991; Nawaz et al., 1992; Hall et al., 1993; Heery et al., 1993). Thus, the transcriptional apparatus required for nuclear hormone receptor function is conserved from yeast to mammals.

This had been unexpected since no nuclear hormone receptor superfamily members had been identified in yeast. Therefore, the factors of the transcriptional machinery required to interact with the ligand binding domain of DAX-1 or a DAX-1-like protein may be normally expressed in yeast and these same factors may be utilized by heterologously expressed mammalian nuclear hormone receptors.

Mutations in DAX-1 that Cause AHC. Many genetic diseases associated with defects in or deletions of nuclear hormone receptor genes have been previously identified (Hughes and O'Malley, 1992; McPhaul, 1994). Mutations in the receptors for androgens, glucocorticoids, vitamin D, and thyroid hormones have been shown to be responsible for hormone resistance sydromes (Hughes and O'Malley, 1992; McPhaul, 1994).

Androgen insensitivity syndrome (AIS) is an X-linked disorder which results in abnormal development of the sexual development of the male. Multiple classes of mutations have been identified in the gene for the androgen receptor in patients with AIS. Both nonsense and missense mutations have been characterized along with mutations that alter the mRNA splicing of the receptor (McPhaul et al., 1991; Marcelli et al., 1990B; Marcelli et al., 1990A; Marcelli et al., 1991; Brown et al, 1990; Lubahn et al., 1989).

Mutations that alter only single amino acids in the DBD and LBD have been shown to result in AIS (Marcelli et al., 1990B; Brown et al., 1990). Similar types of mutations have been identified in the glucocorticoid receptor, thyroid hormone receptor, and vitamin D receptor which have been demonstrated to result in glucocorticoid resistance, generalized resistance to thyroid hormone, and hypocalcaemic vitamin D-resistant rickets, respectively (Karl et al., 1993; Malloy et al., 1990; Richie et al., 1989; Sakurai et al., 1990; Chatterjee et al., 1991; Usala et al., 1991; Hughes et al., 1988).

As discussed above, the DAX-1 gene is frequently deleted in patients with the contiguous gene syndrome, complex glycerol kinase deficiency, involving the loss of the GK locus along with the loci for AHC and/or DMD (McCabe, 1994). Patients with isolated AHC, without clinical features of GK deficiency or DMD, and no detectable deletions have also been described. Intragenic mutations, including microdeletions, insertions, and point mutations have been identified in patients with isolated AHC (Zanaria et al., 1994; Muscatelli et al., 1994; Guo et al., 1995).

A summary of the intragenic mutations identified to date is shown in FIG. 23. Most of the mutations result in frameshifts or are nonsense mutations and thus severely disrupt the sequence of the protein. Only two mutations identified to date alter single amino acids (Muscatelli et al., 1994) and most interestingly these two mutations occur in the highly conserved region II within the LBD. Thus, the ligand binding domain of DAX-1 appears indispensable for normal physiological function.

REFERENCES

1. McKusick V A. Mendelian Inheritance in Man—Catalogs of Atuosomal Dominant, Autosomal Recessive, and X-Linked Phenotypes, ed 10. Baltimore:The Johns Hopkins University Press; 1992.
2. Laverty C R A, Fortune D W, Beischer N A. Congenital idiopathic adrenal hypoplasia. Obstet Gynecol. 1973;41:655–664.
3. McCabe E R B. Disorders of glycerol metabolism. In: Scriver C R, Beaudet A L, Sly W S, Valle D, eds. The Metabolic Basis of Inherited Disease. ed. 7 New York:McGraw-Hill Book Co.; 1994:1631–1652.
4. Worley K C, Towbin J A, Zhu X M, et al. Identification of three new markers in Xp21 between DXS28 (C7) and DMD. Genomics. 1992;13:957–961.
5. Yates J R W, Gillard E F, Cooke A, Colgan J M, Evans T J, Ferguson-Smith M A. A deletion of Xp21 maps congenital adrenal hypoplasia distal to glycerol kinase deficiency. Cytogenet Cell Genet. 1987;46:723.
6. Worley K C, Ellison K A, Zhang Y-H, et al. Yeast artificial chromosome cloning in the glycerol kinase and adrenal hypoplasia congenita region of Xp21. Genomics. 1993;16:407–416.
7. Bardoni B, Zanaria E, Guioli S, et al. A dosage sensitive locus at chromosome Xp21 is involved in male to female sex reversal. Nat Genet. 1994;7:497–501.
8. Golden M P, Lippe B M, Kaplan S A. Congenital adrenal hypoplasia and hypogonadotropic hypogonadism. Am J Dis Child. 1977;131:1117–1118.

9. Zachmann M, Illig R, Prader A. Gonadotropin deficiency and cryptorchidism in three prepubertal brothers with congenital adrenal hypoplasia. J Pediatr. 1980;97:255–257.
10. Hay I D, Smail P J, Forsyth C C. Familial cytomegalic adrenocortical hypoplasia: an X-linked syndrome of pubertal failure. Arch Dis Child. 1981;56:715–721.
11. Martin M M, Martin A L A. The syndrome of congenital hereditary adrenal hypoplasia and hypogonadotropic hypogonadism. Int J Adol Med Hlth. 1985;1:119–137.
12. Matsumoto T, Kondoh T, Yoshimoto M, et al. Complex glycerol kinase deficiency: Molecular genetic, cytogenetic, and clinical studies of five Japanese patients. Am J Med Genet. 1988;31:603–616.
13. Goonewardena P, Dahl N, Ritzen M, van Ommen G J, Pettersson U. Molecular Xp deletion in a male: suggestion of a locus for hypogonadotropic hypogonadism distal to the glycerol kinase and adrenal hypoplasia loci. Clin Genet. 1989;35:5–12.
14. Batch J A, Montalto J, Yong A B W, Gold H, Goss P, Warne G L. Three cases of congenital adrenal hypoplasia: A cause of salt-wasting and mortality in the neonatal period. J Paediatr Child Health. 1991;27:108–112.
15. Zanaria E, Muscatelli F, Bardoni B, et al. An unusual member of the nuclear hormone receptor superfamily responsible for x-linked adrenal hypoplasia congentia. Nature. 1994;372:635–641.
16. Muscatelli F, Strom T M, Walker A P, et al. Mutations in the DAX-1 gene give rise to both x-linked adrenal hypoplasia congentia and hypogonadotropic hypogonadism. Nature. 1994;372:672–676.
17. Partsch C-J, Sippell W G. Hypothalamic hypogonadism in congenital adrenal hypoplasia. Horm Metabol Res. 1989;21:623–625.
18. Guo W, Worley K, Adams V, et al. Genomic scanning for expressed sequences in Xp21 identifies the glycerol kinase gene. Nature Genet. 1993;4:367–372.
19. Southern E M. Detection of specific sequences among DNA fragments separated by gel electrophoresis. J Mol Biol. 1975;98:503–517.
20. Lichter P, Chang Tang C-J, Call K, et al. High-resolution mapping of human chromosome 11 by in situ hybridization with cosmid clones. Science. 1990;247:64–69.
21. Richards R, Heilig R, Oberle I, Storjohann L, Horn G T. Rapid PCR analysis of the St14 (DXS52) VNTR. Nucl Acids Res. 1991;19:1944.
22. Boerwinkle E, Xiong W, Fourest E, Chan L. Rapid typing of tandemly repeated hypervariable loci by the polymerase chain reaction: Application to the apolipoprotein B 3' hypervariable region. Proc Natl Acad Sci, USA. 1989;86:212–216.
23. Ellison K A, Roth E J, McCabe E R B, Chinault A C, Zoghbi H Y. Isolation of a yeast artificial chromosome contig spanning the X chromosomal breakpoint in a patient with Rett syndrome. Am J Med Genet. 1993;47:1124–1134.
24. Worley K C, Lindsay E A, Bailey J, Wise J, McCabe E R B, Baldini A. Rapid molecular cytogenetic analysis of X-chromosomal microdeletions: Fluorescence in situ hybridization (FISH) for complex glycerol kinase deficiency. Am J Med Genet.; 1995:In press.
25. Laudet V, Hanni C, Coll J, Catzeflis F, Stehelin D. Evolution of the nuclear receptor gene superfamily. EMBO J. 1992;11:1003–1013.
26. Glass C K. Differential recognition of target genes by nuclear receptor monomers, dimers, and heterodimers. Endocr Rev. 1994;15:391–407.
27. McKusick V A Mendelian Inheritance in Man. 1992 The Johns Hopkins University Press. 10th ed., pp. 1841–1843.
28. Kelch R P, Virdis R, Rapaport R, Greig F, Levine L S and New M I 1984 Congential adrenal hypoplasia. Pediatr Adolesc Endocrinol 13: 156–161.
29. Seltzer W K, Firminger H, Klein L, Pike A, Fennessey P, McCabe E R B 1985 Adrenal dysfunction in glycerol kinase deficiency. Biochem Med 33: 189–199.
30. Kletter G B, Gorski J L and Kelch, R. P. 1991 Congenital adrenal hypoplasia and isolated gonadotropin deficiency. Trends Endoc. Metab. 2, 123–128.
31. McCabe E R B 1994 Disorders of glycerol metabolism. in "The Metabolic Basis of Inherited Disease," 7th ed. pp. 945–961, New York, McGraw-Hill, New York.
32. Worley K C, Towbin J A, Zhu X M, Barker D F, Ballabio A, Chamberlain J, Biesecker G, Blethen S L, Brosnan P, Fox J E, Rizzo W B, Romeo G, Sakuragawa N, Seltzer W K, Yamaguchi S and McCabe E R B 1992 Identification of the three new markers in Xp21 between DXS28 (C7) and DMD. Genomics 13: 957–961.
33. Worley K C, Ellison K A, Zhang Y.-H., Wang D.-F., Mason J, Roth E J, Adams V, Fogt D D, Zhu X M, Tobin J A, Chinault A C, Zoghbi H and McCabe E R B 1993 Yeast artifical chromosome cloning in the glycerol kinase and adrenal hypoplasia congenita region of Xp21. Genomics 16: 407–416.
34. Yates J R W, Gillard E F, Cooke A, Colgan J M, Evans T J and Ferguson-Smith M A 1987 A deletion of Xp21 maps congenital adrenal hypoplasia distal to glycerol kinase deficiency. Cytogenet. Cell. Genet. 46: 723.
35. Arn P, Chen H, Tuck-Muller C M, Mankinen C, Wachtel G, Li S, Shen C C, and Wachtel S S 1994 SRYX, a sex reversing locus in Xp21.2 to p22.11. Hum. Genet. 93:389–393.
36. Bardoni B, Zanaria E, Guioli S, Floridia G, Worley K, Tonini G, Ferrante E, Chiumello G, McCabe E R B, Fraccaro M, Zuffardi O, and Camerino G 1994 X-linked sex reversal due to a dosage sensitive gene which interferes with testis formation. Nature Genet. 7: 497–501.
37. Zanaria E, Muscatelli F, Bardoni B, Strom T M, Guioli S, Guo W, Lalli E, Moser C, Walker A P, McCabe E R B, Meitinger T, Monaco A P, Sassone-Corsi P, Camerino G 1994 An unusual member of the nuclear hormone receptor superfamily responsible for X-linked adrenal hypoplasia congenita. Nature 372: 635–641.
38. Muscatelli F, Strom T M, Walker A P, Zanaria E, Recan D, Meindl A, Bardoni B, Guioli S, Zehetner G, Rabl W, Schwarz H P, Kaplan J-C, Camerino G, Meitinger T and Monaco AP 1994 Mutation in the DAX-1 gene gives rise to both X-linked adrenal hypoplasia congenita and hypogonadotropic hypogonadism. Nature 372: 672–676.
39. Guo W, Mason J, Stone C G, Morgan S A, Madu S, Baldini A, Lindsay E A, Biesecker L G, Copeland K C, Horlick M N B, Pettigrew A, Zanaria E, McCabe E R B 1995 Diagnosis of X-linked adrenal hypoplasia congenita by mutation analysis of the DAX-1 gene. JAMA 274: 324–330.
40. Genetics Computer Group (GCG), Sequence Analysis Software Package, version 8.0 (University Research park, Madison, Wis., 1994).
41. Sanger F, Micklen S, and Coulson A P 1977 DNA sequencing with chain-terminating inhibitors. Proc. Natl. Acad. Sci. USA 74: 5463–5466.
42. Orita. M., Iwahana, H., Kanazawa, H., Hayashi, K., and Sekiya, T. 1989 Detection of polymorphisms of human DNA by gel electrophoresis as single-strand conformation polymorphisms. Proc. Natl. Acad. Sci. USA 86: 2766–2770.

43. Feinberg A P and Vogelstein B (1983) A technique for radiolabeling DNA restriction endonuclease fragments to high specific activity. Anal. Biochem. 132:6–13.
44. Sambrook J, Fritsch E F and Maniatis T 1989 Molecular Cloning-A Laboratory Manual, 2nd Ed. Cold Spring Harbor, Cold Spring Harbor Laboratory Press.
45. Wang L H, Tsai S Y, Cook G R, Beattie W G, Tsai M J and O'Malley 1989 COUP transcription factor is a member of the steroid receptor superfamily. Nature 340: 163–166.
46. Rice D A, Mouw A R, Bogerd A M and Parker K L. 1991 A shared promoter element regulates the expression of three steroidogenic enzymes. Mol. Endocrinol. 10: 1552–1561.
47. Lala D S, Rice D A, and Parker K L 1992 Steroidogenic factor I, a key regulator of steroidogenic enzyme expression, is the mouse homolog of fushi tarazu-factor I. Mol. Endocri. 6: 1249–1258.
48. White P C, New M I, and Dupont B 1987 Congenital adrenal hyperplasia. N. Engl. J. Med. 316: 1519–1524.
49. John M E, John M C, Boggaram V, Simpson E R, and Waterman M R 1986 Transcriptional regulation of steroid hydroxylase genes by corticotropin. Proc. Natl. Acad. Sci. USA 83: 4715–4719.
50. Luo X, Ikeda Y and Parker K L 1994 A cell-specific nuclear receptor is essential for adrenal and gonadal development and sexual differentiation. Cell 77: 481–490.
51. Ikeda Y, Shen W.-H., Ingraham H A and Parker K L 1994 Development expression of mouse steroidogenic factor 1, an essential regulator of the steroid hydroxylases. Mol. Endocrinol. 8: 654–662.
52. Ingraham H A, Lala D S, Ikeda Y, Lou X, Shen W.-H., Nachtigal M W, Abbud R, Nilson J H and Parker K L 1994 The nuclear receptor steroidogenic factor 1 acts at multiple levels of the reproductive axis. Genes & Dev. 8: 2302–2312.
53. Ikeda Y., Luo X., Abbud R., Hilson J. H., and Parker K. L. 1995 The nuclear receptor steroidogenic factor 1 is essential for the formation of the ventromedial hypothalamic nucleus. Mol. Endocrinol. 9: 478–486.
54. Guo W, Burris T P, McCabe E R B 1995 Expression of DAX-1, the Gene Responsible for X-Linked Adrenal Hypoplasia Congenita and Hypogonadotropic Hypogonadism, in the Hypothalamic-Pituitary-Gonadal Axis and human adrenocortical carcinoma cell line. Biochem. Molecul. Medic. in press.
55. Evans R M 1988 The steroid and thyroid hormone receptor superfamily. Science 240: 889–895.
56. Laudet V, Hanni C, Coll J, Catzeflis F and Stehelin D 1992 Evolution of the nuclear receptor gene superfamily. EMBO J. 11: 1003–1013.
57. Luisi B F, Xu W X, Otwinowski Z, Freesman L P, Yamamoto K R, and Sigler P B 1991 Crystallographic analysis of the interaction of the glucocorticoid receptor with DNA. Nature 352: 497–505.
58. Ponglikimongkol M, Green S and Chambon P 1988 Genomic organization of the human estrogen receptor gene. EMBO J 7: 3385–3388.
59. Huchaby C S, Conneely O M, Beattie W G, Dobson A D W, Tsai M J and O'Malley BW 1987 Structure of the chromosomal chicken progesterone receptor gene. Proc. Natl. Acad. Sci. USA 84: 8380–8384.
60. Arriza J L, Weinberger C, Cerelli G, Glaser T M, Handelin B L, Housman D E and Evans R N 1987 Cloning of human mineralocorticoid receptor complementary DNA: structural and functional relationship with the glucocorticoid receptor. Science 237: 268–275.
61. Ritchie H H, Wang L H, Tsai S Y and O'Malley B W 1990 COUP-TF gene: a structure unique for the steroid/thyroid receptor superfamily. Nucleic Acids Res. 18: 6857–6862.
62. Ignacio J E and Sevilla D D 1991 The genomic structure of the human glucocorticoid receptor. J. Bio. Chem. 266(11): 7182–7188.
63. Helena R H, Wang L.-H., Tsai S, O'Malley B W, and Tsai M.-J. 1990 COUP-TF gene: a structure unique for the steroid/thyroid receptor superfamily. Nucl. Acid. Res. 18: 6857–6862.
64. Baniahmad A, Burris T P, and Tsai M J 1995 The nuclear hormone receptor superfamily in "Mechanism of steroid hormone regulation of the transcription". R.G. Landes Co. Austin Ch1. pp. 1–24.
65. Schena M and Yamamoto KR 1988 Mammalian glucocorticoid receptor derivatives enhance transcription in yeast. Science 241: 965–967.
66. Metzger D, White J H and Chambon P 1988 The human estrogen receptor functions in yeast. Nature 334: 31–36.
67. McDonnell D P, Pick J W, Drutz D J, Butt T R, and O'Malley 1989 Reconstitution of the vitamin D-responsive osteocalcin transcription unit in Saccharomyces cerevisiae. Mol. Cell. Bio. 9: 3517–3523.
68. Privalsky M L, Sharif M and Yamamoto K R 1990 The viral erbA oncogene protein, a constitutive repressor in animal cells, is a hormone-regulated activator in yeast. Cell 63: 1277–1286.
69. Wilson T E, Fahrner T J, Johnston M, and Milbrandt J 1991 Identification of the DNA binding site for NGFI-B by genetic selection in yeast. Science 252: 1296–1300.
70. Nawaz Z, Tsai M J, McDonnell D P, and O'Malley B W 1992 Identification of novel steroid response elements. Gene Expression 2: 39–47.
71. Hall B L, Smit-McBride Z, and Privalsky M L 1993 Reconstitution of retinoid X receptor function and combinatorial regulation of other nuclear hormone receptors in the yeast *Saccharomyces cerevisiae*. Proc. Natl. Acad. Sci. USA 90: 6929–6933.
72. Heery D M, Zacharewski T, Pierrat B, Gronemeyer H, Chambon P and Losson R 1993 Efficient transactivation by retinoic acid receptor in yeast requires retinoid X receptors. Proc. Natl. Acad. Sci. USA 90: 4281–4285.
73. Kelch R P, Virdis R, Rapaport R, Greig F, Levine L S, New M I. Congenital adrenal hypoplasia. Pediatr Adolesc Endocrinol 13:156–161, 1984.
74. Sikl H. Addison's disease due to congenital hypoplasia of the adrenals in an infant aged 33 days. J Pathol Bacter 60:323–324, 1948.
75. Laverty C R A, Fortune D W, Beischer N A. Congenital idiopathic adrenal hypoplasia. Obstet Gynec N.Y. 41:655–664, 1973.
76. Favara B E, Franciosi R A, Miles V. Idopathic adrenal hypoplasia in children. Amer J Clin Pathol 57:287–296, 1972.
77. Ohlbaum P, Hehunstre P P, Bouchet J L, Deminiere C. Insuffisance surrenale chronique et hyalinose segmentaire et focale familiale: unenouvelle association. Pediatrie 41:86, 1986.
78. McKusick V A. Mendelian inheritance in man. 10th Edition. The Johns Hopkins University Press, 1992, pp. 1841–1843.
79. Seltzer W K, Firminger H, Klein J, Pike A, Fennessey P, McCabe E R B. Adrenal dysfunction in glycerol kinase deficiency. Biochem Med 33:189-199, 1985.
80. Marsden H B, Zakkhour H D. Cytomegalic adrenal hypoplasia with pituitary cytomegaly. Virchows Arch Abt A Path Anat Histol 378:105–110, 1978.

81. Martin M M, Martin A L A. The syndrome of congenital hereditary adrenal hypoplasia and hypogonadotropic hypogonadism. Int J Adol Med Hlth 1:119–137, 1985.
82. Prader A, Zachman M, Illig R. Luteinizing hormone deficiency in hereditary congenital adrenal hypoplasia. J Pediatr 86:421–422, 1975.
83. Dunkel L, Perheentupa J, Virtanen M, Maenpaa J. GnRH and hCG tests are both necessary in differential diagnosis of male delayed puberty. Am J Dis Child 139:494–498, 1985).
84. Partsch C-J, Sippel W G. Hypothalamic hypogonadism in congenital adrenal hypoplasia. Horm Metabol Res 21:623–625, 1989.
85. Virdis R, Levine L S, Levy D, Pang S. Congenital adrenal hypoplasis: two new cases. J. Endocrinol Invest 6:51–54, 1983.
86. Kletter G B, Gorski J L, Kelch R P. Congenital adrenal hypoplasia a nd isolated gonadotropin deficiency. Trends Endoc Metab 2:123–128, 1991.
87. Hensleigh P A, Moore W V, Wilson K, Tulchinsky D. Congenital X-linked adrenal hypoplasia. Obstet Gynec 52:228–232, 1978.
88. Zachmann M, Illig R, Prader A. Gonadotropin deficiency and crytorchidism in three prepubertal brothers with congenital adrenal hypoplasia. J Pediatr 92:255–256, 1980.
89. Wise J E, Matalon R, Morgan A M, McCabe E R B. Phenotypic features of patients with congenital adrenal hypoplasia and glycerol kinase deficiency. Am J Dis Child 141:744–747, 1987 .
90. Schwanzel-Fukuda M, Jorgensen K L, Bergen H T, Weesner G D, Pfaff D W. Biology of normal luteinizing hormone-releasing hormone neurons during and after their migration from olfactory placode. Endocr Rev 13:623–634, 1992.
91. Franco B, Guiol S, Pragliola A, Incerti B, Bardoni B, Tonlorenzi R, Carrozzo R, Maestrini E, Pieretti M, Taillon-Miller P, Brown C J, Willard H F, Lawrence C, Persico M G, Camerion G, Ballabio A. A gene deleted in Kallmann's syndrome shares homology with neural cell adhesion and axonal path-finding molecules. Nature 353:529–536, 1991.
92. Legouis R, Hardelin J-P, Levillers J, Claverie J-M, Compain S, Wunderlw V, Millassear P, Le Paslier D, Cohen D, Caterina D, Bougueleret L, Delemarre-Van de Wall H, Luttalla G, Weissenbach J, Petit C. The candidate gene for the X-linked Kallmann syndrome encodes a protein related to adhesion molecules. Cell 67:423–435, 1991.
93. Worley K C, Ellison K A, Zhang Y-H, Wang D-F, Mason J, Roth E J, Adams V, Fogt D D, Zhu X M, Tobin J A, Chinault A C, Zoghbi H, McCabe E R B. Yeast artificial chromosome cloning in the glycerol kinase and adrenal hypoplasia congenita region of Xp21. Genomics 16:407–416, 1993.
94. Walker A P, Muscatelli F, Monaco A P. Isolation of the human Xp21 glycerol kinase gene by positional cloning. Hum Mol Genet 2:107–114, 1993.
95. Arn P, Chen H, Tuck Muller C M, Mankinen C, Wachtel G, Li S, Shen C C, Wachtel S S. A sex reversing locus in Cp21.2 to p22.11. Hum Genet 93:389–393, 1994.
96. Bardoni B, Zanaria E, Guioli S, Floridia G, Worley K, Tonini G, Ferrante E, Chiumello G, McCabe E R B, Fraccaro M, Zuffardi O, Camerino G. X-linked sex reversal due to a dosage sensitive gene which interferes testis formation. Nature Genet 7:497–501, 1994.
97. Zanaria E, Muscatelli F, Bardoni B, Strom T M, Guioli S, Guo W, Lalli E, Moser C, Walker A P, McCabe E R B, Meitinger T, Monaco A P, Sassone-Corsi P, Camerino G. An unusual member of the nuclear hormone receptor superfamily responsible for X-linked adrenal hypoplasia congenita. Nature 372:635–641, 1994.
98. Muscatelli F, Strom T M, Walker A P, Zanaria E, Recan D, Meindl A, Bardoni B, Guioli S, Zehetner G, Rabl W, Schwarz H P, Kaplan J C, Camerino G, Meitinger T, Monaco A P. Mutation in the DAX-1 gene gives rise to both X-linked adrenal hypoplasia congenita and hypogonadotropic hypogonadism. Nature 372:672–676, 1994.
99. Guo W, Mason J, Stone C G, Morgan S A, Muda S, Baldini A, Lindsay E A, Biesecker L G, Copelland K, Horlick M N B, Pettigrew A, Zanaria E, McCabe E R B. Diagnosis of X-linked adrenal hypoplasia congenita by mutation analysis of the DAX-1 gene. JAMA, in press.
100. Guo W, Mason J, Burris T P, McCabe E R B. X-linked adrenal hypoplasia congenita: characterization of the genomic region. Pediatr Res 37:90A, 1995.
101. Lala D S, Rice D A, Parker K L. Steroidogenic factor I, a key regulator of steroidogenic enzyme expression, is the mouse homolog of fushi tarazu-factor I. Mol Endocrinol 6:1249–1258, 1992.
102. Ikeda Y, Shen W-H, Ingraham H A, Parker K L. Development expression of mouse steroidogenic factor 1, an essential regulator of the steroid hydroxylases. Mol Endocrinol 8:652–654, 1994.
103. Luo X, Ikeda Y, Parker K L. A cell-specific nuclear receptor is essential for adrenal and gonadal development and sexual differentiation. Cell 77:481–490, 1994.
104. Ikeda Y, Luo X, Abbud R, Hilson J H, Parker K L. The nuclear receptor steroidogenic factor 1 is essential for the formation of the ventromedial hypothalamic nucleus. Mol Endocrinol 9:478–486, 1995.
105. Feinberg AP, Vogelstein B. A technique for radiolabeling DNA restriction endonuclease fragments to high specific activity. Anal Biochem 132:6–13, 1993.
106. Gazder A F, Oie H K, Shackleton C H, Chen T R, Triche T J, Myers C E, Chrousos G P, Brennan M F, Stein C A, La-Rocca R V. Establishment and characterization of a human adrenocortical carcinoma cell line that expresses multiple pathways of steroid biosynthesis. Cancer Res 50:5488–5496, 1990.
107. Chomczynski P, Sacchi N. Single step method of RNA isolation by acid guanidinium thiocyanate-phenol-chloroform extraction. Anal Biochem 162:156–159, 1987.
108. Sambrook J, Fritsch E F, Maniatis T. Molecular Cloning—A Laboratory Manual. 2nd Ed. Cold Spring Harbor: Cold Spring Harbor Laboratory Press, 1989.
109. Staels B S, Hum D W, Miller W L. Regulation of steroidogenesis in NCI-H295 cells: a cellular model of the human fetal adrenal. Mol Endocrinol 7:423–433, 1993.
110. Pierce J D, Parsons R F. Glycoprotein hormones: structure and function. Annu Rev Biochem 50:465–495, 1981.
111. Waldhauser F, Weissenbacher G, Frisch H. Pulsatile secretion of gonadotropins in early infancy. Eur J Pediatr 137:71–74, 1981.
112. Fink G. Gonadotropin secretion and its control. In The Physiology of Reproduction. Knobil E, Neill J D. (Eds.) New York: Raven Press, pp. 1349–1377, 1988.
113. Schwanzel-Fukuda M, Pfaff D W. Origin of luteining hormone-releasing hormone neurons. Nature 338:161, 1989.
114. Gharib S D, Wierman M E, Shupnik M A, Chin W W. Molecular biology of the pituitary gonadotropins. Endocrinol Rev 11:177–199, 1990.

115. Ingraham H A, Lala DS, Ikeda Y, Lou X, Shen W-H, Nachtigal M W, Abbud R, Nilson J H, Parker K L. The nuclear receptor steroidogenic factor 1 acts at multiple levels of the reproductive axis. Genes & Dev 8:2302–2312, 1994.

116. Baniahmad, A., Kohne, A. C., and Renkawitz, R. (1992) EMBO J 11, 1015–1023. Baniahmad, A., Ha, I., Reinberg, D., Tsai, S. Y., Tsai, M. J., and O'Malley, B. W. (1993) Proc Natl Acad Sci USA 90, 8832–8836.

117. Baniahmad, A., and Tsai, M.-J. (1993) J Cell Biochem 51, 151–156.

118. Baniahmad, A., Burris, T. P., and Tsai, M. J. (1994) In "Mechanism of Steroid Hormone Regulation of Gene Transcription" (M. J. Tsai, and B. W. O'Malley, eds.) pp. 1–24, RG Landes Co, Austin, Tex.

119. Baniahmad, A., Leng, X., Burris, T. P., Tsai, S. Y., Tsai, M. J., and O'Malley, B. W. (1995) Mol Cell Biol 15, 76–86.

120. Bardoni, B., Zanaria, E., Guioli, S., Floridia, G., Worley, K., Tonini, G., Ferrante, E., Chiumello, G., McCabe, E. R. B., Fraccaro, M., Zuffardi, O., and Camerino G. (1994) Nature Genet 7, 497–501.

121. Barettino, D., Vivanco Ruiz, M. M., and Stunnenberg, H. G. (1994) EMBO J 13, 3039–3049. Beato, M. (1991) FASEB J 5, 2044–2051.

122. Bocquel, M. T., Kumar, V., Stricker, C., Chambon, P., and Gronemeyer, H. (1989) Nucleic Acids Res 17, 2581–2594.

123. Bourguet, W., Ruff, M., Chambon, P., Gronemeyer, H., and Moras, D. (1995) Nature 375,377–382.

124. Brown, T. R., Lubahn, D. B., Wilson, E. M., French, F. S., Mieron, C. J, and Corden, J. L. (1990) Mol Endocrinol 4, 1749–1772.

125. Burris, T. P., Guo, W., and McCabe, Chatterjee, W. K. K., Nagaya, T., Madison, L. D., Datta, S., Tentoumis, A., and Jameson, J. L. (1991) J Clin Invest 87, 1977–1984.

126. Cooney, A. J., and Tsai, S. Y. (1994)In "Mechanism of Steroid Hormone Regulation of Gene Transcription" (M. J. Tsai, and B. W. O'Malley, eds.) pp. 25–48, RG Landes Co, Austin, Tex.

127. Conneely, O. M., and O'Malley, B. W. (1994)In "Mechanism of Steroid Hormone Regulation of Gene Transcription" (M. J. Tsai, and B. W. O'Malley, eds.) pp. 111–123, RG Landes Co, Austin, Tex.

128. Danielian, P. S., White, R., Lees, J. A., and Parker, M. G. (1992) EMBO J 11, 1025–1033.

129. Durand, B., Saunders, M., Gaudon, C., Roy, B., Losson, R., and Chambon, P. (1994) EMBO J 13, 5370–5382.

130. Evans, R. M. (1988) Science 240, 889–895.

131. Favara, B. E., Franciosi, R. A., and Miles, V. (1972) Amer J Clin Pathol 57, 287–296.

132. Forman, B. M., and Samuels, H. H. (1990) Mol Endocrinol 4, 1293–1301.

133. Glass, C. K. (1994) Endocr Rev 15, 391–407.

134. Green, S., and Chambon, P. (1988) Trends Genet 4, 309–314.

135. Guiochon-Mantel, A., Loosfelt, H., Lescop, P., Sar, S., Atger, M., Perrot-Applunat, M., and Milgrom, E. (1989) Cell 57, 1147–1154.

136. Guo, W., Worley, K., Adams, V., Mason, J., Sylvester-Jackson, D., Zhang, Y. H., Towbin, J. A., Fogt, D. D., Madu, S., Wheeler, D. A., and McCabe, E. R. B. (1993) Nature Genet 4, 367–372.

137. Guo, W., Mason, J., Stone, C. G., Morgan, S. A., Muda, S., Baldini, A., Lindsay, E. A., Biesecker, L. G., Copelland, K., Horlick, M. N. B., Pettigrew, A., Zanaria, E., and McCabe, E. R. B. (1995) JAMA 274, 324–330.

138. Guo, W., Burris, T. P., and McCabe, E. R. B. (1995) Biochem Mol Med 56, 8–13.

139. Guo, W., Burris, T. P., Zhang, Y. H., Huang, B. L., Mason, J., Copeland, K. C., Kupfer, S. R., Pagon, R. A., and McCabe, E. R. B. (in press) J Clinical Endocrinology and Metabolism.

140. Hall, B. L., Smit-McBride, Z., and Privalsky, M. L. (1993) Proc Natl Acad Sci USA 90, 6929–6933.

141. Heery, D. M., Zacharewski, T., Pierrat, B., Gronemeyer, H., Chambon, P., and Losson, R. (1993) Proc Natl Acad Sci USA 90, 4281–4285.

142. Hensleigh, P. A., Moore, W. V., Wilson, K., and Tulchinsky, D. (1978) Obster Gynec 52, 228–232.

143. Herskowitz, I (1987) Nature 329, 219–222.

144. Hollenberg, S. M., and Evans, R. M. (1988) Cell 55, 899–906.

145. Hughes, M. R., Malloy, P. J., Kieback, D. G., Kesterson, R. A., Pike, J. W., Feldman, D., and O'Malley, B. W. (1988) Science 242, 1702–1705.

146. Hughes, M. R., and O'Malley, B. W. (1992) In "Nuclear Hormone Receptors", (M. Parker, ed.), pp. 321–353, Academic Press, New York.

147. Ikeda, Y., Lala, D. S., Luo, X., Kim, E., Moisan, M. P., and Parker, K. L. (1993) Mol Endocrinol 7, 852–860.

148. Ikeda, Y., Shen, W. H., Ingraham, H. A., and Parker, K. L. (1994) Mol Endocrinol 8, 652–654.

149. Ingraham, H. A., Lala, D. S., Ikeda, Y., Lou, X., Shen, W. H., Nachtigal, M. W., Abbud, R., Nilson, J. H., and Parker, K. L. (1994) Genes & Dev 8, 2302–2312.

150. Fawell, S. E., Lees, J. A., White, R., and Parker, M. G. (1990) Cell 60, 953–962.

151. Karl, M., Lamberts, S. W. J., Detera-Wadleigh, S. D., Encio, I. J., Stratakis, C. A., Hurley, D. M., Accili, D., and Chrousos, G. P. (1993) J Clin Endocrinol Metab 76, 683–689.

152. Kelch, R. P., Virdis, R., Rapaport, R., Greig, F., Levine, L. S., and New, M. I. (1984) Pediatr Adolesc Endocrinol 13, 156–161.

153. Kletter, G. B., Gorski, J. L., and Kelch, R. P. (1991) Trends Endocrinol Metab 2, 123–128.

154. Klug, A., and Rhodes, D. (1987) Trends Biochem Sci 12, 464–469.

155. Krust, A., Green, S., Argos, P., Kumar, V., Walter, P., Bornett, J. M., and Chambon, P. (1986) EMBO J 5, 891–897.

156. Kumar, V., Green, S., Staub, A., and Chambon, P. (1986) EMBO J 5, 2231–2236.

157. Kumar, V., and Chambon, P. (1988) Cell 55, 145–156.

158. Laverty, C. R. A., Fortune, D. W., and Beischer, N. A. (1973) Obstet Gynec 41, 655–664.

159. Lee, J. W., Gulick, T., and Moore, D. D. (1992) Mol Endocrinol 6, 1867–1873.

160. Leng, X., Blanco, J., Tsai, S. Y., Ozato, K., O'Malley, B. W., and Tsai, M. J. (1995) Mol Cell Biol 15, 255–263.

161. Lubahn, D. B., Brown, T. R., Simental, J. A., Higg, S. H. N., Migeora, C. J., Wilson, E. M., and French, F. S. (1989) Proc Natl Acad Sci USA 86, 9534–9538.

162. Luo, X., Ikeda, Y., and Parker, K. L. (1994) Cell 77, 481–490.

163. Lydon, J. P., Power, R. F., and Conneely, O. M. (1992) Gene Exp 2, 273–283. Malloy, P. J., Hochberg, Z., Tiosano, D., Pike, J. W., Hughes, M. R., and Feldman, D. (1990) J Clin Invest 86, 2071–2079.

164. Marsden, H. B., and Zakkhour, H. D. (1978) Virchows Arch Abt A Path Anat Histol 378, 105–110.

165. Marecelli, M., Tilley, W. D., Wilson, C. M., Wilson, J. D., Griffin, J. E., and McPhaul, M. J. (1990A) J Clin Invest 85, 1522–1528.

166. Marcelli, M., Tilley, W. D., Wilson, C. M., Griffin, J. E., Wilson, J. D., and McPhaul, M. J. (1990B) Mol Endocrinol 4, 1105–1116.
167. Marcelli, M., Zoppi, S., Grino, P. B., Griffin, J. E., Wilson, J. D., and McPhaul, M. J. (1991) J Clin Invest 87, 1123–1126.
168. Marsden, H. B., and Zakkour, H. D. (1978) Virchows Arch Abt A Path Anat Histol 378, 105–110.
169. Martin, M. M., and Martin, A. L. A. (1985) Int J Adol Med Hlth 1, 119–137.
170. McDonnell, D. P., Pick, J. W., Drutz, D. J., Butt, T. R., and O'Malley, B. W. (1989) Mol Cell Biol 9, 3517–3523.
171. Metzger, D., White, J. H., and Chambon, P. (1988) Nature 334, 31–36.
172. McCabe, E. R. B. (1994) In "The Metabolic Basis of Inherited Disease" (C. R. Scriver, A. L. Beaudet, W. S. Sly, and D. Valle, eds.), pp. 945–961, McGraw-Hill, New York.
173. McKusick, V. A. (1992) "Mendelian Inheritance in Man." The Johns Hopkins University Press, Baltimore.
174. McPhaul, M. J., Marcelli, M., Tilley, W. D., Griffin, J. E., and Wilson, J. D. (1991) FASEB J 5, 2910–2915.
175. McPhaul, M. J. (1994) In "Steroid Hormone Action" (M. Parker, ed.), pp. 186–208, IRL Press, New York.
176. Muscatelli, F., Strom, T. M., Walker, A. P., Zanaria, E., Recan, E., Meindl, A., Bardoni, B., Guioli, S., Zehetner, G., Rabl, W., Schwarz, H. P., Kaplan, J. C., Camerino, G., Meitinger, T., and Monaco, A. P. (1994) Nature 372, 672–676.
177. Nawaz, Z., Tsai, M. J., McDonnell, D. P., and O'Malley, B. W. (1992) Gene Exp 2, 39–47.
178. O'Halloran, T. V. (1993) Science 261, 715–725.
179. Ohlbaum, P., Hehunstre, P. P., Bouchet, J. L., and Deminiere, C. (1986) Pediatrie 41, 86.
180. O'Malley, B. W. (1990) Mol Endocrinol 4, 363–369.
181. O'Malley, B. W., and Conneely, O. M. (1992) Mol Endocrinol 6, 1359–1361.
182. Partsch, C.-J., and Sipple, W. G. (1989) Horm Metabol Res 21, 623–625.
183. Picard, D., Salser, S. J., and Yamamoto, K. R. (1988) Cell 54, 1073–1080.
184. Power, R. F., Conneely, O. M., and O'Malley, B. W. (1992) Trends Pharmacol Sci 13, 318–323.
185. Prader, A., Zachman, M., and Illig, R. (1975) J Pediatr 86, 421–422.
186. Privalsky, M. L., Sharif, M., and Yamamoto, K. R. (1990) Cell 63, 1277–1286.
187. Richie, H. H., Hughes, M. R., Thompson, E. T., Malloy, P. J., Hochberg, Z., Feldman, D., Pike, J. W., and O'Malley, B. W. (1989) Proc Natl Acad Sci USA 86, 9783–9787.
188. Sakurai, A., Miyamoto, T., Refetoff, S., and DeGroot, L. J. (1990) Mol Endocrinol 4, 1988–1994.
189. Seltzer, W. K., Firminger, H., Klein, J., Pike, A., Fennessey, P., and McCabe, E. R. B. (1985) Biochem Med 33, 189.
190. Schena, M., and Yamamoto, K. R. (1988) Science 241, 965–967.
191. Tasset, D., Tora, L., Fromental, C., Scheer, E., and Chambon, P. (1990) Cell 62, 1177–1187.
192. Tate, B. F., Allenby, G., Janocha, R., Kazmer, S., Speck, J., Sturzenbecker, L. J., Abarzua, P., Levin, A. A., and Grippo, J. F. (1994) Mol Cell Biol 14, 2323–2330.
193. Tora, L., White, J. H., Brou, C., Tasset, D. M., Webster, N. J. G., Scheer, E., and Chambon P. (1989) Cell 59, 477–487.
194. Truss, M., and Beato, M. (1993) Endocr Rev 14, 459–479.
195. Usala, S. J. (1991) Thyroid 1, 361–367.
196. Virdis, R., Levine, L. S., Levy, D., and Pang, S. (1983) Endocrinol Invest 6, 51–54.
197. Wang, L. H., Tsai, S. Y., Cook, G. R., Beattie, W. G., Tsai, M. J., and O'Malley, B. W. (1989) Nature 340, 163–166.
198. Webster, N. J. G., Green, S., Jin, J., and Chambon, P. (1988) Cell 54, 199–207.
199. Wilson, T. E., Fahrner, T. J., Johnston, M., and Milbrandt, J. (1991) Science 252, 1296–1300.
200. Wise, J. E., Matalon, R., Morgan, A. M., and McCabe, E. R. B. (1987) Am J Dis Child 141, 744–747.
201. Worley, K. C., Towbin, J. A., Zhu, X. M., Barker, D. F., Ballabio, A., Chamberlain, J., Biesecker, G., Blethen, S. L., Brosnan, P., Fox, J. E., Rizzo, W. B., Romeo, G., Sakuragawa, N., Seltzer, W. K., Yamaguchi, S., and McCabe, E. R. B. (1992) Genomics 13, 957–961.
202. Worley, K. C., Ellison, K. A., Zhang, Y. H., Wang, D. F., Mason, J., Roth, E. J., Adams, V., Fogt, D. D., Shu, X. M., Tobin, J. A., Chinault, A. C., Zoghbi, H., and McCabe, E. R. B. (1993) Genomics 16, 407–416.
203. Yates, J. R. W., Gillard, E. F., Cooke, A., Colgan, J. M., Evans, T. J., and Ferguson-Smith, M. A. (1987) Cytogent Cell Genet 46, 723.
204. Zachmannn, M., Illig, R., and Prader, A. (1980) J Pediatr 92, 255–256.
205. Zanaria, E., Muscatelli, F., Bardoni, B., Strom, T. M., Guioli, S., Guo, W., Lalli, E., Moser, C., Walker, A. P., McCabe, E. R. B., Meitinger, T., Monaco, A. P., Sassone-Corsi, P., and Camerino, G. (1994) Nature 372, 635–641.
206. McCabe, E R B, Guo, W, Burris, T P (in press) Mental Retardation and Developmental Disabilities Reviews.
207. Burris, T P, Guo, W, McCabe, E R B (1996) Recent Progress in Hormone Research 51, 241–260.
208. Burris, T P, Guo, W, Le, T, McCabe E R B (1995) Biochemical and Biophysical Research Communications 214, 576–581.
209. Vogiatzi, M G, Gunn, S K, Scheuerle, A E, McCabe E R B, Copeland, K C (1995) J Clinical Endocrinology and Metabolism 80, 1079–1082.

What is claimed is:

1. A nucleic acid molecule consisting of a nucleotide sequence beginning with position 1 and ending with position 1579 of SEQ ID NO.: 1.

2. A nucleic acid molecule consisting of a DAX-1 promoter sequence beginning at nucleotide position 1408 and ending at position 1416 of SEQ ID NO.: 1.

3. A vector comprising a DAX-1 promoter sequence beginning at nucleotide position 1408 and ending at position 1416 of SEQ ID NO.: 1 operatively linked to a heterologous coding sequence.

* * * * *